United States Patent
Taniguchi

(10) Patent No.: US 10,299,765 B2
(45) Date of Patent: May 28, 2019

(54) ULTRASOUND PROBE AND ULTRASOUND IMAGE DIAGNOSTIC APPARATUS

(71) Applicant: Konica Minolta, Inc., Tokyo (JP)

(72) Inventor: Tetsuya Taniguchi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/676,310

(22) Filed: Apr. 1, 2015

(65) Prior Publication Data

US 2015/0289849 A1 Oct. 15, 2015

(30) Foreign Application Priority Data

Apr. 14, 2014 (JP) .................................. 2014-082675

(51) Int. Cl.
*A61B 8/08* (2006.01)
*A61B 8/14* (2006.01)
(Continued)

(52) U.S. Cl.
CPC .............. *A61B 8/5269* (2013.01); *A61B 8/08* (2013.01); *A61B 8/4444* (2013.01);
(Continued)

(58) Field of Classification Search
CPC ......... A61B 8/14; A61B 8/4444; A61B 8/461; A61B 8/467; A61B 8/5207; A61B 8/5253;
(Continued)

(56) References Cited

U.S. PATENT DOCUMENTS

| | | | | |
|---|---|---|---|---|
| 6,603,240 B1* | 8/2003 | Kohno | .................... | B06B 1/064 |
| | | | | 310/334 |
| 2007/0167807 A1* | 7/2007 | Takeuchi | ................. | A61B 8/12 |
| | | | | 600/459 |
| 2014/0066768 A1* | 3/2014 | Sui | ....................... | G01S 7/52038 |
| | | | | 600/443 |

FOREIGN PATENT DOCUMENTS

| | | |
|---|---|---|
| CN | 1649544 A | 8/2005 |
| JP | 2002301068 A | 10/2002 |

OTHER PUBLICATIONS

The extended European Search Report dated Sep. 9, 2015 issued from the corresponding European Patent Application No. 15161208.2.

(Continued)

*Primary Examiner* — Angela M Hoffa
*Assistant Examiner* — Vani Gupta
(74) *Attorney, Agent, or Firm* — Lucas & Mercanti, LLP

(57) ABSTRACT

An ultrasound probe includes: an ultrasound input/output unit to output a transmission ultrasound to a test object by a pulse signal; and a signal input/output unit to output a reception signal when the ultrasound input/output unit receives a reflected ultrasound from the test object, wherein the ultrasound probe is set so that a difference between maximum and minimum values of a group delay in a transmission/reception frequency band at −20 dB of the ultrasonic probe is equal to or less than 0.15 radian, the group delay being obtained from a phase difference for each frequency between the input pulse signal and the reception signal obtained from the reflected ultrasound of the transmission ultrasound output by the pulse signal, or so that a standard deviation of the group delay in the transmission/reception frequency band at −20 dB of the ultrasonic probe is equal to or less than 0.025.

18 Claims, 29 Drawing Sheets

(51) Int. Cl.
*A61B 8/00* (2006.01)
*G01S 7/52* (2006.01)
*G01S 15/89* (2006.01)

(52) U.S. Cl.
CPC .......... *A61B 8/4483* (2013.01); *A61B 8/5207* (2013.01); *A61B 8/54* (2013.01); *G01S 7/5202* (2013.01); *G01S 7/52038* (2013.01); *G01S 7/52047* (2013.01); *G01S 15/895* (2013.01); *A61B 8/0866* (2013.01); *A61B 8/48* (2013.01)

(58) Field of Classification Search
CPC ..... A61B 8/5269; A61B 8/54; G01S 7/52038; G01S 15/89; G01S 15/895; G01S 7/5202; G01S 7/52047
See application file for complete search history.

(56) References Cited

OTHER PUBLICATIONS

Office Action dated Apr. 10, 2017 from corresponding Chinese Patent Application No. CN 201510167123.9 and English translation; Total of 17 pages.
Office Action dated Oct. 16, 2017 from corresponding Chinese Patent Application No. CN 201510167123.9 and English translation.
Office Action dated Mar. 26 1, 2018 from corresponding Chinese Patent Application No. CN 201510167123.9 and English translation.

\* cited by examiner

ULTRASOUND PROBE AND ULTRASOUND IMAGE DIAGNOSTIC APPARATUS

CROSS REFERENCE TO RELATED APPLICATION

This Application claims the priority of Japanese Patent Application No. 2014-082675 filed on Apr. 14, 2014, which is incorporated by reference herein.

BACKGROUND OF THE INVENTION

Field of the Invention

The present invention relates to an ultrasound probe and an ultrasound image diagnostic apparatus.

Description of Related Art

According to ultrasound diagnostics, a realtime display of heartbeat and/or motion of a fetus can be executed by a simple operation of applying an ultrasound probe to a body surface. Additionally, the ultrasound diagnostics are excellent in safety, and enable repeated examinations.

With regard to such technique to display ultrasound images, it has been known that a high contrast image can be obtained by imaging higher harmonic components (e.g. frequencies $2f_0$, $3f_0$, etc.) with respect to a fundamental component (frequency $f_0$) of a transmission signal. This imaging method is referred to as Tissue Harmonic Imaging.

The higher harmonic components appear mainly due to nonlinear distortions occurring when ultrasound propagates through a test object. Concretely, when the ultrasound irradiates a living body, the ultrasound signal is distorted due to a nonlinear response of tissue while propagating through the tissue, and thereby the higher harmonic components increase. As a result, a reception signal includes the frequency $2f_0$ which is twice the frequency $f_0$, and/or the frequency $3f_0$ which is three times the frequency $f_0$.

As a method for extracting the higher harmonic components in the Tissue Harmonic Imaging, there has been known a filter method and a pulse inversion method.

The filter method extracts, for example, the higher harmonic component $2f_0$ from the reception signal, by using a bandpass filter having a center frequency of $2f_0$.

The pulse inversion method transmits the first transmission pulse signal and the second transmission pulse signal obtained by polarity inversion or time reversal with a predetermined time interval, and combines the reception signals so that the fundamental components are canceled and thereby the secondary higher harmonic components are emphasized.

In the meantime, there is a problem that the higher harmonic components contained in the ultrasound signal are easily influenced by attenuation when propagating through a test object because higher harmonic components generally have higher frequencies than that of the fundamental component, and accordingly penetration of the reflected ultrasound signal from a deep part is not good. The penetration can be improved by lowering the frequency $f_0$ of the fundamental component so as to suppress the influence of the attenuation, but a tradeoff relationship occurs in this case, namely, the resolution is degraded.

Among the above two method, the filter method cuts a low frequency region without distinction of fundamental wave and higher harmonics wave, and thereby the influence of the attenuation remarkably appears. In addition, the filter method makes the extracted frequency band narrower, and accordingly the image quality deteriorates more than that of the pulse inversion method. For this reason, the pulse inversion method has become the mainstream in the devices/apparatuses other than low-end devices/apparatuses.

In recent years, there has been proposed a method for improving the image quality of the ultrasound images by using various kinds of higher harmonic components, for example, by using the secondary higher harmonic component and a differential sound component having a lower frequency than that of the secondary higher harmonic component so as to cope with the wider bandwidth ultrasound in the above-described pulse inversion method (for example, see Japanese Patent Application Laid-Open Publication No. 2002-301068).

However, the technique described in Japanese Patent Application Laid-Open Publication No. 2002-301068 has the problem that when the plural kinds of higher harmonic components are used, cancellation among the plural higher harmonics waves occurs due to group delay characteristics of the ultrasound probe. As a result, an intended distance resolution cannot be always obtained.

SUMMARY OF THE INVENTION

An object of the present invention is to provide an ultrasound probe and an ultrasound image diagnosis apparatus which can obtain ultrasound images having an excellent distance resolution by reducing cancellation among a plurality of kinds of higher harmonics waves.

To achieve at least one of the above objects, an ultrasound probe reflecting a first aspect of the present invention includes: an ultrasound input/output unit to output a transmission ultrasound to a test object in response to an input of a pulse signal; and a signal input/output unit to output a reception signal when the ultrasound input/output unit receives a reflected ultrasound from the test object, wherein the ultrasound probe is set so that a difference between a maximum value and a minimum value of a group delay in a transmission/reception frequency band at −20 dB of the ultrasonic probe is equal to or less than 0.15 radian, the group delay being obtained from a phase difference for each frequency between the input pulse signal and the reception signal obtained from the reflected ultrasound of the transmission ultrasound output by the pulse signal, or so that a standard deviation of the group delay in the transmission/reception frequency band at −20 dB of the ultrasonic probe is equal to or less than 0.025.

Preferably, in the ultrasound probe, a fractional bandwidth at −20 dB is 120% or more.

An ultrasound image diagnosis apparatus reflecting a second aspect of the present invention includes: an ultrasound probe which outputs at least one transmission ultrasound to a test object in response to an input of at least one pulse signal, and outputs at least one reception signal when at least one reflected ultrasound from the test object is received; and a transmission section which outputs a pulse signal of a predetermined driving waveform so as to cause the ultrasound probe to generate the transmission ultrasound, wherein the transmission section outputs the pulse signal of the driving waveform according to which a difference between a maximum value and a minimum value of a group delay obtained from a phase difference in each frequency, in a frequency band where a frequency band included in a transmission/reception frequency band at −20 dB of the ultrasound probe and a frequency band at −20 dB of the driving waveform in the pulse signal overlap each other, is equal to or less than 0.15 radian, or according to which a standard deviation of the group delay in the frequency band where the frequency band included in the transmission/reception frequency band at −20 dB of the ultrasound probe and the frequency band at −20 dB of the driving waveform in the pulse signal overlap each other is equal to or less than 0.025.

An ultrasound image diagnosis apparatus reflecting a third aspect of the present invention includes: an ultrasound probe which outputs a transmission ultrasound to a test object in response to an input of a pulse signal, and outputs a reception signal when a reflected ultrasound from the test object is received; and a transmission section which outputs a pulse signal of a predetermined driving waveform so as to cause the ultrasound probe to generate the transmission ultrasound, wherein the ultrasound probe and the driving waveform of the pulse signal output from the transmission section are set so that a difference between a maximum value and a minimum value of a totaling value in a frequency band where a frequency band included in a transmission/reception frequency band at −20 dB of the ultrasound probe and a frequency band at −20 dB of the driving waveform in the pulse signal overlap each other is equal to or less than 0.15 radian, the totalizing value being obtained by totalizing a group delay obtained from a phase difference in each frequency between the pulse signal input to the ultrasound probe and the reception signal obtained from the reflected ultrasound of the transmission ultrasound output by the pulse signal and a group delay obtained from a phase difference in each frequency of the pulse signal output by the transmission section.

Preferably, in the ultrasound image diagnosis apparatus, the ultrasound probe is set so that a difference between a maximum value and a minimum value of a group delay in the transmission/reception frequency band at −20 dB of the ultrasound probe is equal to or less than 0.15 radian, the group delay being obtained from a phase difference in each frequency between the input pulse signal and the reception signal obtained from the reflected ultrasound of the transmission ultrasound output by the pulse signal, or so that a standard deviation of the group delay in the transmission/reception frequency band at −20 dB of the ultrasound probe is equal to or less than 0.025, and the transmission section outputs the pulse signal of the driving waveform according to which a difference between a maximum value and a minimum value of a group delay obtained from a phase difference in each frequency, in a frequency band where a frequency band included in a transmission/reception frequency band at −20 dB of the ultrasound probe and a frequency band at −20 dB of the driving waveform in the pulse signal overlap each other, is equal to or less than 0.15 radian, or a standard deviation of the group delay in the frequency band where the frequency band included in the transmission/reception frequency band at −20 dB of the ultrasound probe and the frequency band at −20 dB of the driving waveform in the pulse signal overlap each other is equal to or less than 0.025.

Preferably, in the ultrasound image diagnosis apparatus, the transmission section outputs the pulse signal of the driving waveform in which the frequency band where the frequency band included in the transmission/reception frequency band at −20 dB of the ultrasound probe and the frequency band at −20 dB of the driving waveform in the pulse signal overlap each other covers 70% or more of a transmission/reception frequency bandwidth at −20 dB of the ultrasound probe.

Preferably, in the ultrasound image diagnosis apparatus, the transmission section outputs the pulse signal of the driving waveform whose period is equal to or more than 1.5.

Preferably, in the ultrasound image diagnosis apparatus, the transmission section outputs the pulse signal of the driving waveform whose pulse duration is equal to or more than a time corresponding to two periods at a center frequency of the transmission/reception frequency band at −20 dB of the ultrasound probe.

Preferably, in the ultrasound image diagnosis apparatus, the transmission section outputs the pulse signal according to a control signal of five values or less.

Preferably, in the ultrasound image diagnosis apparatus, the transmission section outputs the pulse signals of different driving waveforms to a same scanning line with a predetermined time interval for plural times, and the ultrasound image diagnosis further includes an image generating section to combine the reception signals obtained from the reflected ultrasounds of the transmission ultrasounds generated by the plural pulse signals to generate an ultrasound image data based on the combined reception signals.

Preferably, in the ultrasound image diagnosis apparatus, the transmission section outputs the pulse signals whose driving waveforms have an asymmetric relationship with each other to the same scanning line with the predetermined time interval for plural times.

Preferably, in the ultrasound image diagnosis apparatus, the transmission section outputs the pulse signal including intensity peaks of a frequency power spectrum on a low frequency side and on a high frequency side with respect to a center frequency of the transmission/reception frequency band at −20 dB of the ultrasonic probe.

Preferably, in the ultrasound image diagnosis apparatus, the transmission section outputs the pulse signal including two or more of intensity peaks of a frequency power spectrum on the high frequency side with respect to the center frequency of the transmission/reception frequency band at −20 dB of the ultrasound probe.

BRIEF DESCRIPTION OF THE DRAWINGS

The present invention will become more fully understood from the detailed description given hereinbelow and the appended drawings, and thus are not intended as a definition of the limits of the present invention, and wherein.

PREFERRED EMBODIMENT OF THE PRESENT INVENTION

Figure 1:
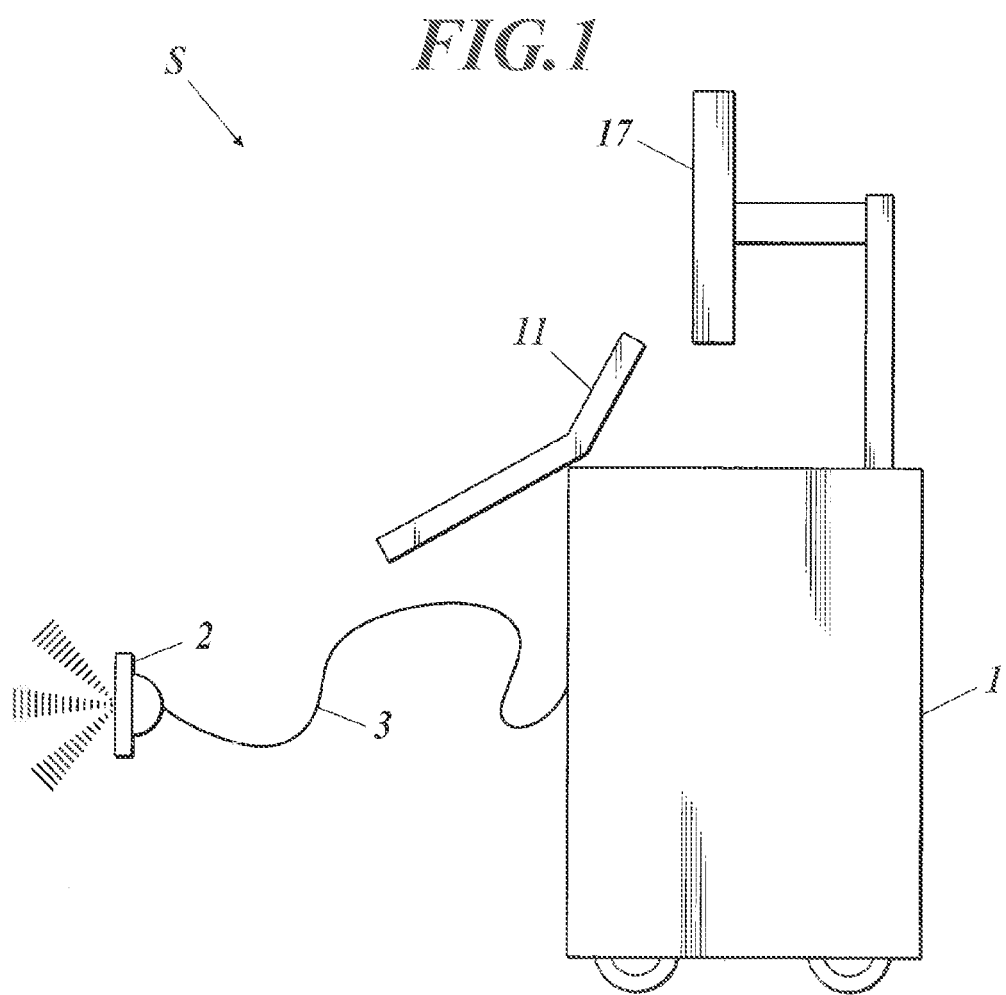
FIG. 1 is a diagram illustrating an external configuration of an ultrasound image diagnosis apparatus.

Hereinafter an ultrasound image diagnosis apparatus according to embodiments of the present invention will be described with reference to the drawings. In this regard, however, the scope of the invention is not limited to the illustrated examples. The same functions and configurations are described with the same reference characters, respectively, in the following descriptions, and redundant descriptions are omitted.

Figure 2:
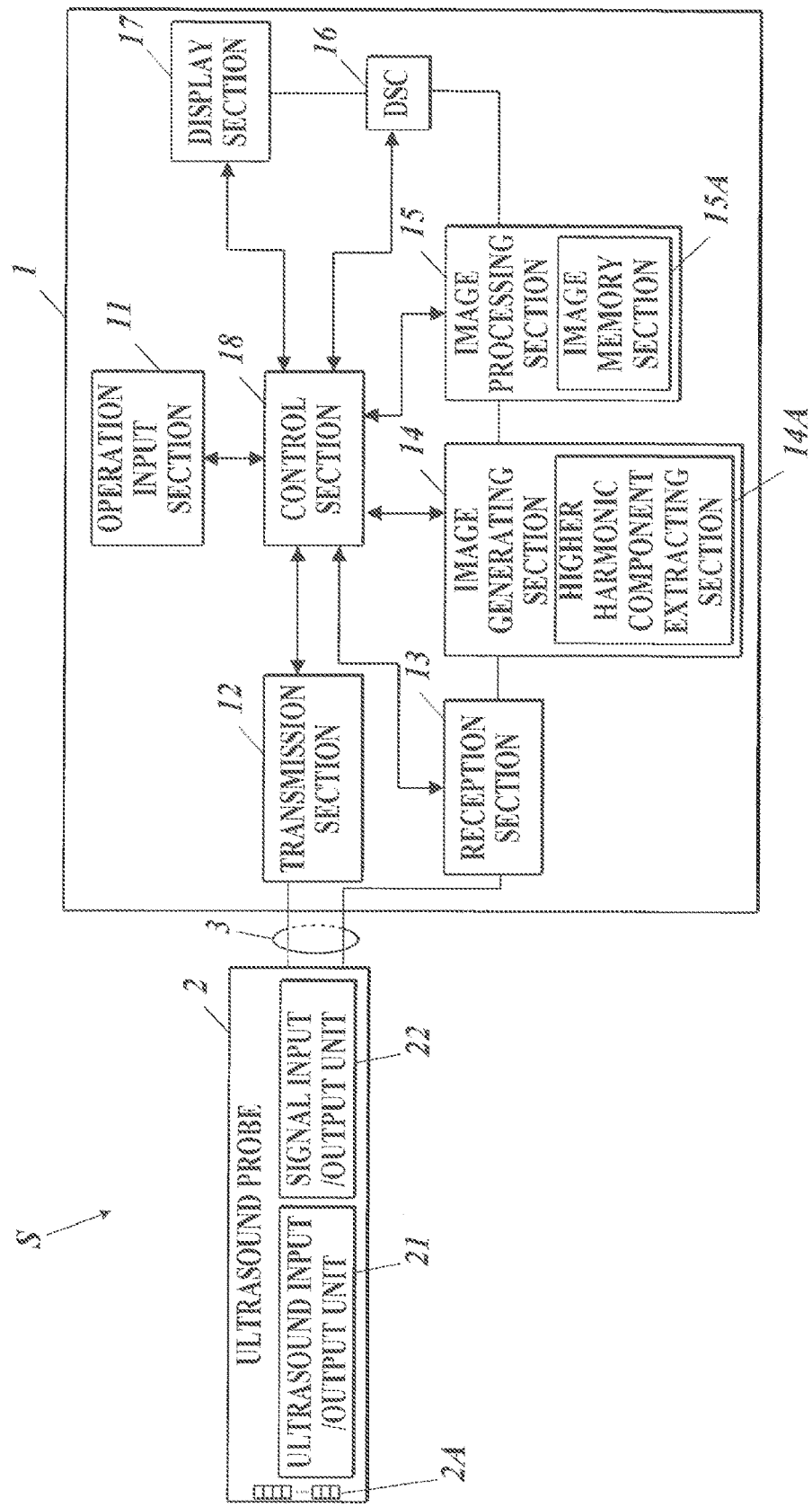
FIG. 2 is a block diagram illustrating a schematic configuration of the ultrasound image diagnosis apparatus.

An ultrasound image diagnosis apparatus S of this embodiment is equipped with an ultrasound image diagnosis apparatus body 1 and an ultrasound probe 2, as illustrated in FIGS. 1 and 2. The ultrasound probe 2 includes an ultrasound input/output unit 21 which transmits an ultrasound (transmission ultrasound) to a not-illustrated test object such as a living body, and receives a reflected wave (reflected ultrasound: echo) reflected on the test object. The ultrasound image diagnosis apparatus body 1 is connected to a signal input/output unit 22 of the ultrasound probe 2 via a cable 2. The ultrasound image diagnosis apparatus body 1 transmits an electrical driving signal to the signal input/output unit 22 of the ultrasound probe 2 so as to cause the ultrasound probe 2 to transmit the transmission ultrasound to the test object, and images an internal state of the test object as an ultrasound image based on an electrical reception signal generated by the ultrasound probe 2 in response to the reflected ultrasound received by the ultrasound probe 2 from the inside of the test object.

The ultrasound probe 2 has a composition including, for example, a backing layer, piezoelectric layer, acoustic matching layer and acoustic lens, which are laminated. The piezoelectric layer is equipped with oscillators 2A each including a piezoelectric device(s), and the oscillators 2A are arranged, for example, in one-dimensional array state in an orientation direction. This embodiment uses the ultrasound probe 2 including 192 oscillators 2A. Alternatively, the oscillators 2A can be arranged in two-dimensional array state. The number of the oscillators 2A can be arbitrary set. This embodiment adopts an electronic scan probe of linear scanning type as the ultrasound probe 2. Alternatively, either an electronic scanning type or a mechanical scanning type may be adopted, and any of a linear scanning type, sector scanning type and convex scanning type may be adopted. The effects of this embodiment are increased by adopting the ultrasound probe which can execute broadband transmission of the ultrasound with good sensitivity to obtain a high resolution transmission ultrasound, and thereby the ultrasound image having better qualities can be obtained. The bandwidth of the ultrasound probe can be arbitrary set. Preferably, a fractional bandwidth at −20 dB is 120% or more.

This embodiment uses the ultrasound probe having group delay characteristics according to which a difference between the maximum value and the minimum value of the transmission/reception frequency band at −20 dB is 0.15 radian or less.

The group delay characteristics of the ultrasound probe means group delay characteristics in a transmission/reception result of the ultrasound, and can be obtained from a phase difference, for each frequency, between an electrical signal applied to the ultrasound probe and an electrical signal obtained as a result of transmission/reception of the ultrasound.

Figure 3A:
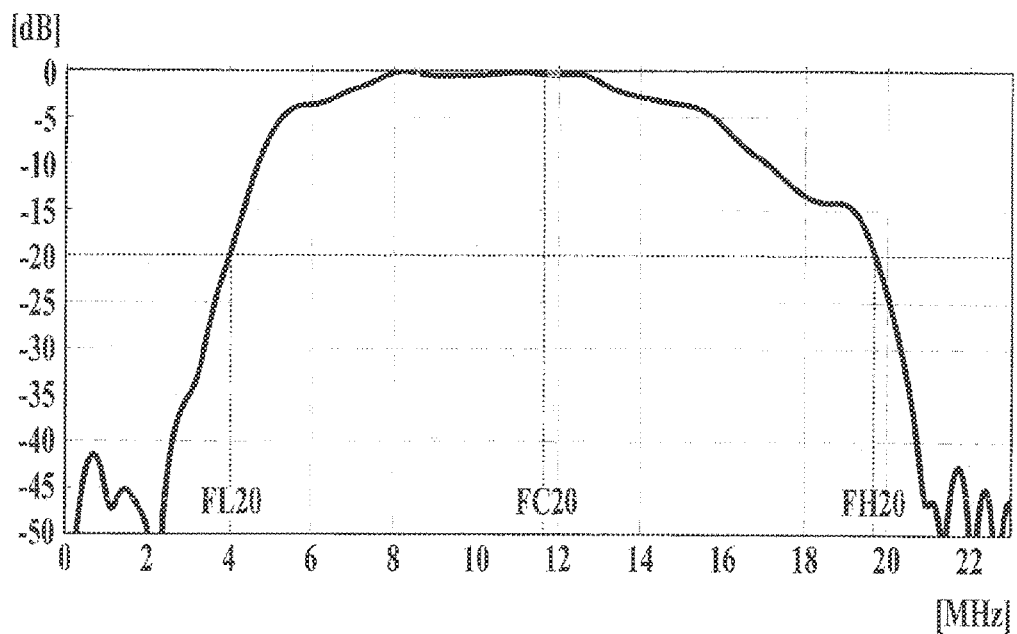
FIGS. 3A and 3B are diagrams each explaining transmission/reception band characteristics and group delay characteristics of an ultrasound probe.
Figure 3B:
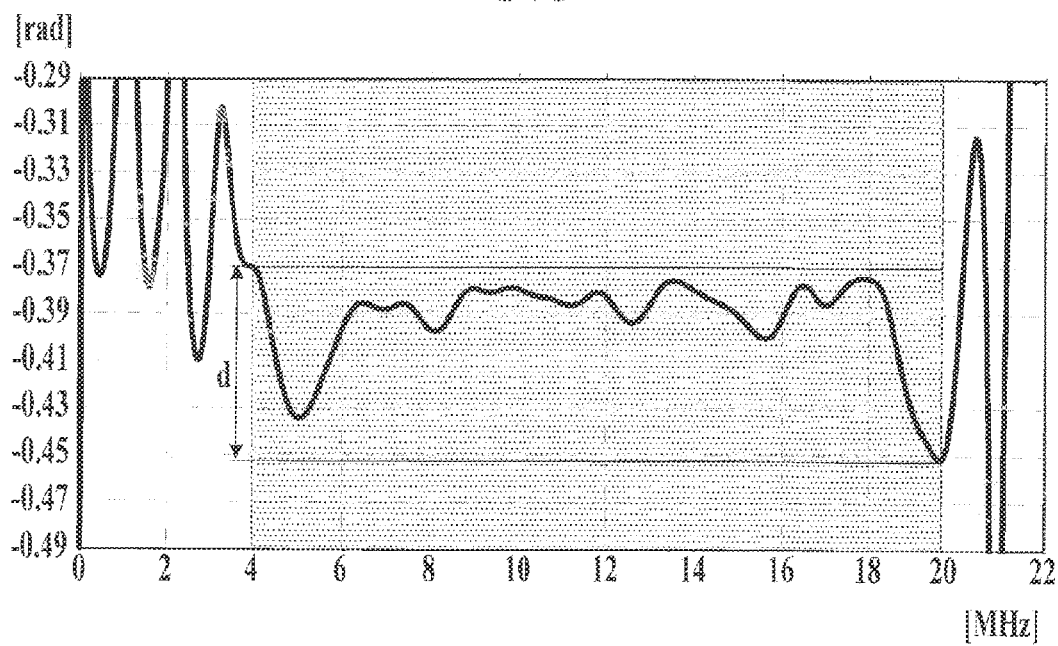

Specifically, for example, in the ultrasound probe having the transmission/reception band characteristics illustrated in FIG. 3A, the lower limit frequency (FL20) at −20 dB is 3.99 MHz, and the upper limit frequency (FH20) at −20 dB is 19.72 MHz. Thus, the transmission/reception frequency band at −20 dB is 3.99 to 19.72 MHz. The group delay characteristics of the ultrasound probe having the transmission/reception band characteristics of FIG. 3A is illustrated in FIG. 3B. As illustrated in FIG. 3B, the phase difference (delay amount) changes for each frequency, and the characteristics thereof is different depending on the characteristics of the ultrasound probe. In this embodiment, it is important that a range of vibration in the transmission/reception frequency band at −20 dB, at which transmission and reception of the ultrasound are effectively performed, is small in this group delay, namely, a difference (d) between the maximum value and the minimum value of the group delay amounts is small. The smaller the difference is, the more preferred the reception signal can be obtained, because cancellation hardly occur among a plurality of kinds of higher harmonic waves and an intended distance resolution can be obtained. Preferably, the difference between the maximum value and the minimum value is 0.15 radian or less.

Incidentally, also the group delay characteristics according to which the standard deviation in the transmission/reception frequency band at −20 dB is 0.025 or less can achieve the same effects.

The standard deviation of the group delays can be obtained, for example, by the following formula (1) indicating the standard deviation when subject data is considered as a whole population.

[Formula 1]

$$\sqrt{\frac{\sum (x-\bar{x})^2}{n}} \quad (1)$$

wherein $\bar{x}$ represents an average value of the subject data, and n represents the number of pieces of the subject data.

The granularity of data of the group delay characteristics for calculation is preferably 200 points or more in the transmission/reception frequency band at −20 dB of the ultrasound probe so as to enable obtaining reproducible results.

The group delay characteristics of the ultrasound probe 2 can be controlled by appropriately changing parameters of components of the ultrasound probe 2. For example, the frequency characteristics and/or the group delay characteristics of the ultrasound probe 2 can be adjusted by appropriately setting characteristics of piezoelectric material applied to the oscillators 2A, damping performance and/or acoustic reflection performance of backing material composing the backing layer, the number of sheets of the acoustic matching material composing the acoustic matching layer, acoustic impedance and thickness of the acoustic matching material, etc. Also filler filled between the oscillators 2A, through which the ultrasound does not pass directly, has influence on an unwanted vibration mode, and consequently the group delay characteristics of the oscillators 2A. Accordingly, changing of parameters related to the filler and/or a manufacturing process of the ultrasound probe 2 may be adjustment elements for controlling the group delay characteristics. Therefore, the ultrasound probe 2 having various characteristics can be produced by a comprehensive adjustment.

The ultrasound image diagnosis apparatus body 1 is equipped with, for example, an operation input section 11, transmission section 12, reception section 13, image generating section 14, image processing section 15, Digital Scan Converter (DSC) 16, display section 17 and control section 18, as illustrated in FIG. 2.

The operation input section 11 is composed of various switches, buttons, track ball, mouse, keyboard, etc. for inputting data such as a command to instruct to start the diagnosis and personal information of the test object, and outputs operation signals to the control section 18.

Figure 4:
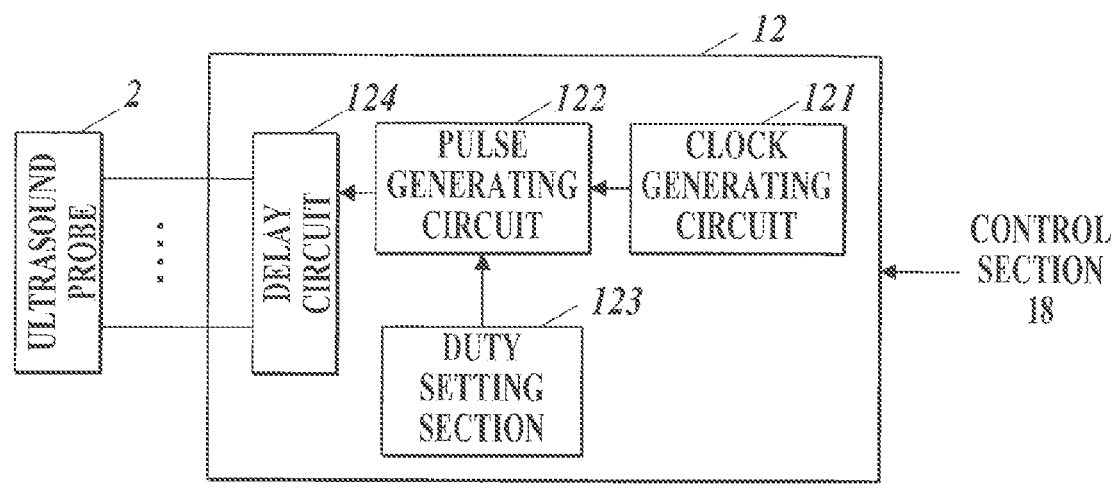
FIG. 4 is a block diagram illustrating a schematic configuration of a transmission section.

The transmission section 12 is a circuit which supplies the electrical driving signal to the ultrasound probe 2 via the cable 3 according to the control of the control section 18 so as to cause the ultrasound probe 2 to generate the transmission ultrasound. More specifically, as illustrated in FIG. 4, the transmission section 12 is equipped with a clock generating circuit 121, pulse generating circuit 122, duty setting section 123 and delay circuit 124.

The clock generating circuit 121 is a circuit which generates a clock signal determining the transmitting timing and/or transmission frequency of the driving signal.

Figure 5:
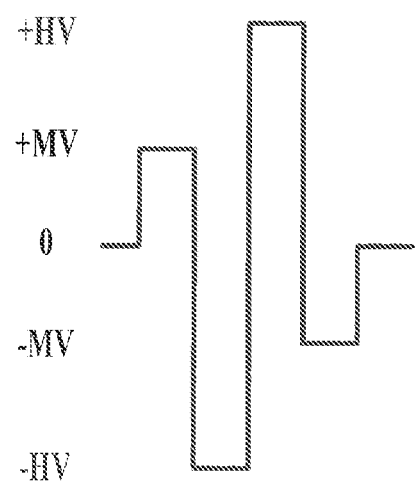
FIG. 5 is a diagram explaining a driving waveform of a pulse signal.

The pulse generating circuit 122 is a circuit which generates a pulse signal as the driving signal at a predetermined cycle. As illustrated in FIG. 5, the pulse generating circuit 122 switches a voltage among five values (+HV/+MV/0/−MV/−HV) to output the switched voltage, and thereby the pulse signal of rectangular wave is generated. The amplitude in positive polarity of the pulse signal is same as that in negative polarity in this example, but the amplitude is not limited to that. This embodiment switches the voltage among the five values to output the switched voltage, but the number of the values is not limited to five and can be set to an appropriate value. Preferably, the number of the values is five or less. This can improve flexibility of a control of frequency components at low costs, and thereby higher resolution transmission ultrasound can be obtained.

The duty setting section 123 sets a duty ratio of the pulse signal output from the pulse generating circuit 122. Concretely, the pulse generating circuit 122 outputs the pulse signal of the pulse waveform according to the duty ratio set by the duty setting section 123. The duty radio can be changed, for example, by an input operation in the operation input section 11.

In this embodiment, the duty ratio of the pulse signal is preferably set so that peaks included in the transmission/reception frequency band of the ultrasound probe 2 occur on low frequency side and on high frequency side with respect to the center frequency of the transmission/reception frequency band of the ultrasound probe 2. More preferably, the duty setting section 123 sets the duty ratio of the pulse signal so that the sensitivity in the transmission/reception frequency band at −20 dB of the ultrasound probe 2 becomes −20 dB or more.

Figure 6A:
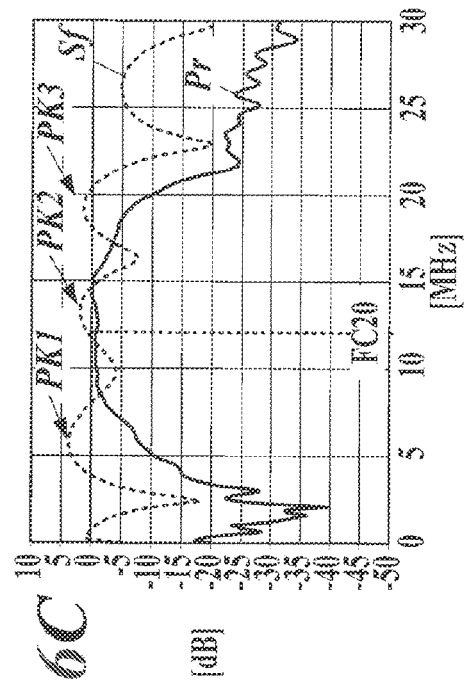
FIGS. 6A, 6B, 6C and 6D are diagrams each explaining a relationship between a transmission/reception band of the ultrasound probe and the driving waveform of the pulse signal.
Figure 6C:
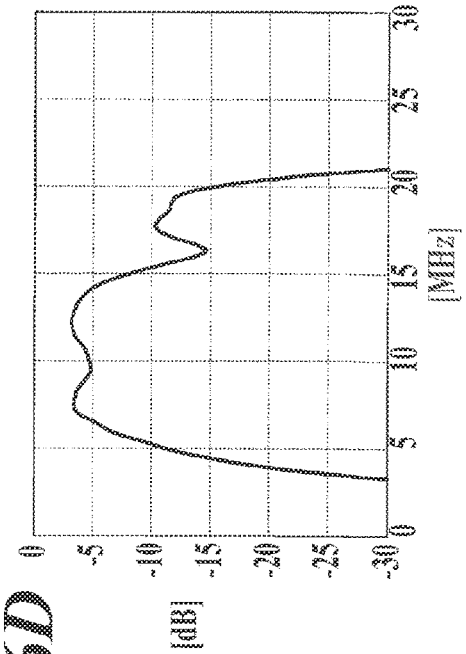
Figure 6B:
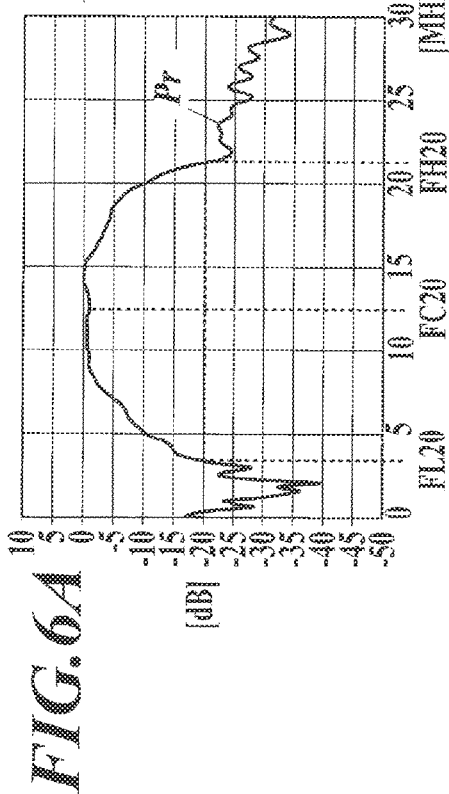
Figure 6D:
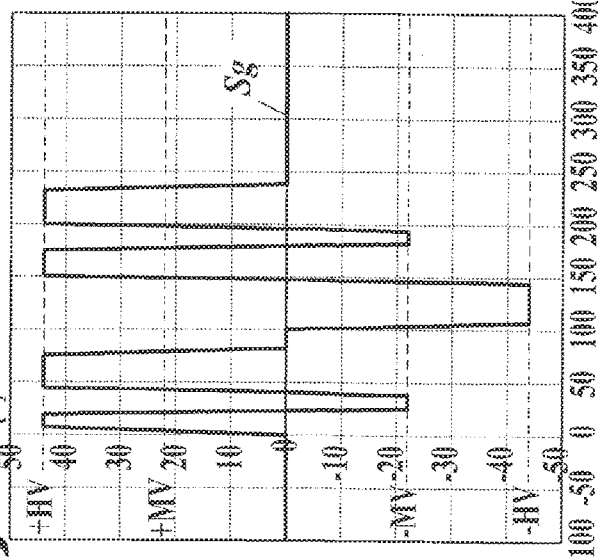

More detailed descriptions will be given with reference to FIGS. 6A, 6B, 6C and 6D. FIG. 6A illustrates an example of transmission/reception band characteristics Pr of the ultrasound probe. FIG. 6B illustrates an example of the driving waveform of the pulse signal output from the transmission section 12. FIG. 6C illustrates a frequency power spectrum obtained by a frequency analysis (FFT) of the driving waveform of the pulse signal of FIG. 6B. FIG. 6D illustrates the result of the frequency analysis (FFT) of the transmission ultrasound output from the ultrasound probe.

For example, the ultrasound probe of FIG. 6A has a peak frequency of 14.2 MHz, a lower limit frequency (FL20) at −20 dB of 3.4 MHz, an upper limit frequency (FH20) at −20 dB of 21.2 MHz, a center frequency at −20 dB (FC20) of 12.3 MHz and a fractional bandwidth at −20 dB of 145%.

To this ultrasound probe, for example, a pulse signal Sg having the driving waveform of FIG. 6B is applied. The pulse signal Sg is composed of a rectangular wave, and can be generated by switching the voltage among the five values. As illustrated in FIG. 6C, the frequency power spectrum, which is obtained by the frequency analysis of the driving waveform of the pulse signal Sg, has one (1) intensity peak (PK1: 5.8 MHz) on the low frequency side and two intensity peaks (PK2: 13.2 MHz, PK3: 19.2 MHz) on the high frequency side with respect to the center frequency (FC20) in the transmission frequency band at −20 dB of the ultrasound probe (the analysis result is indicated by "Sf" in FIG. 6C). In other words, when the pulse signal having the driving waveform of FIG. 6B is applied to the ultrasound probe having the characteristics of FIG. 6A, the peaks (PK1 to PK3) included in the transmission/reception frequency band of the ultrasound probe appear on the low frequency side and on the high frequency side with respect to the center frequency (FC20) in the transmission/reception frequency band (FL20 to FH20) of the ultrasound probe. At that time, the intensities (P1: 3.8 dB, P2: 2.0 dB, P3: 1.4 dB) at the respective intensity peaks are larger than the intensity (1.1 dB) of the frequency component of the frequency (12.3 MHz) same as the center frequency in the transmission/reception frequency band of the ultrasound probe. Each of intensities in the frequency regions between the adjacent intensity peaks is −20 dB or more on the basis of the intensity at PK1 which is the maximum value among the intensities of the intensity peaks. As a result, the transmission ultrasound having the characteristics illustrated in FIG. 6D is output from the ultrasound probe.

The transmission/reception band characteristics of the ultrasound probe 2 and/or the driving waveform of the pulse signal according to this embodiment is not limited to the above, and can be arbitrary set within the scope in which the present invention can be executed.

This embodiment outputs the pulse signal which has two intensity peaks on the high frequency side with respect to the center frequency (FC20) in the transmission/reception frequency band of the ultrasound probe 2. Alternatively, the pulse signal may have three or more intensity peaks. By making the pulse signal have two or more intensity peaks on the high frequency side with respect to the center frequency (FC20) in the transmission/reception frequency band of the ultrasound probe 2, it becomes possible to output the pulse signal having wider band on the high frequency side. Alternatively, the pulse signal may have only one (1) intensity peak on the high frequency side with respect to the center frequency (FC20) in the transmission/reception frequency band of the ultrasound probe 2.

The delay circuit 124 is a circuit which sets a delay time to a transmission timing of the driving signal for each of individual paths corresponding to the oscillators so as to delay transmission of the driving signal by the set delay time so that transmission beams composed of transmission ultrasounds are focused.

The transmission section 12 having the above configuration sequentially switches the oscillators 2A to which the driving signals are supplied, respectively, while shifting the oscillators 2A by a predetermined number every time the ultrasound is transmitted/received according to the control of the control section 18, and performs scanning by supplying the driving signals to the oscillators 2A whose outputs are selected.

In this embodiment, the transmission section 12 is configured to output the pulse signal of the driving waveform having the group delay characteristics according to which the difference between the maximum value and the minimum value is 0.15 radian or less in the frequency band where the frequency band contained in the transmission/reception frequency band at −20 dB of the ultrasound probe 2 and the frequency band at −20 dB of the driving waveform in the pulse signal overlap each other. In this embodiment, the phase component for each frequency at the time of performing the frequency analysis of the driving waveform is considered as the response delay, and the obtained calculation result is regarded as the group delay characteristics of the driving waveform.

Figure 7A:
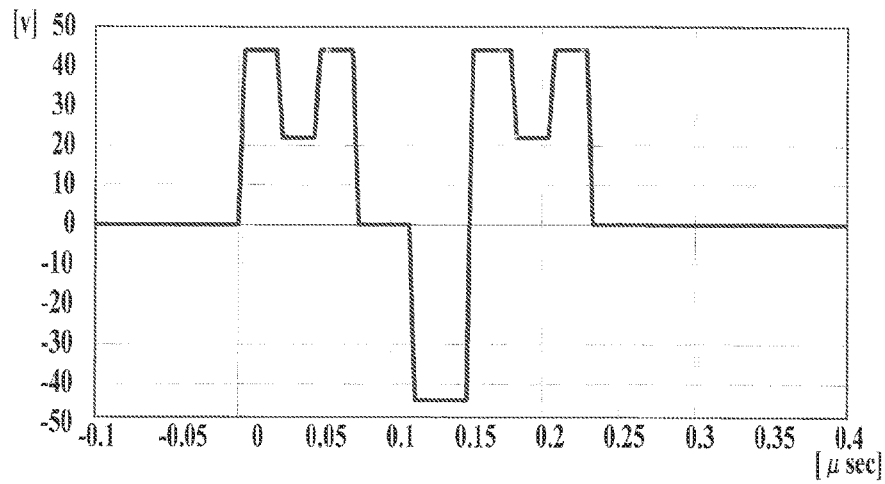
FIGS. 7A, 7B and 7C are diagrams each explaining driving waveform characteristics.
Figure 7B:
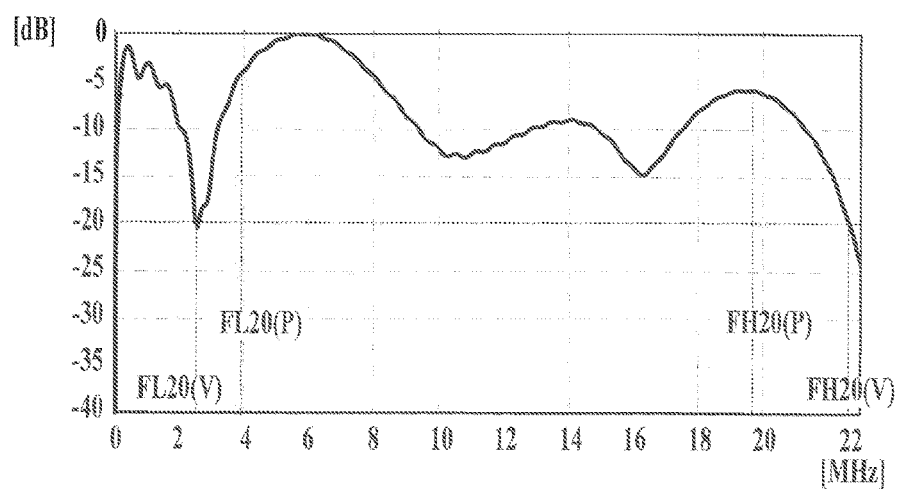
Figure 7C:
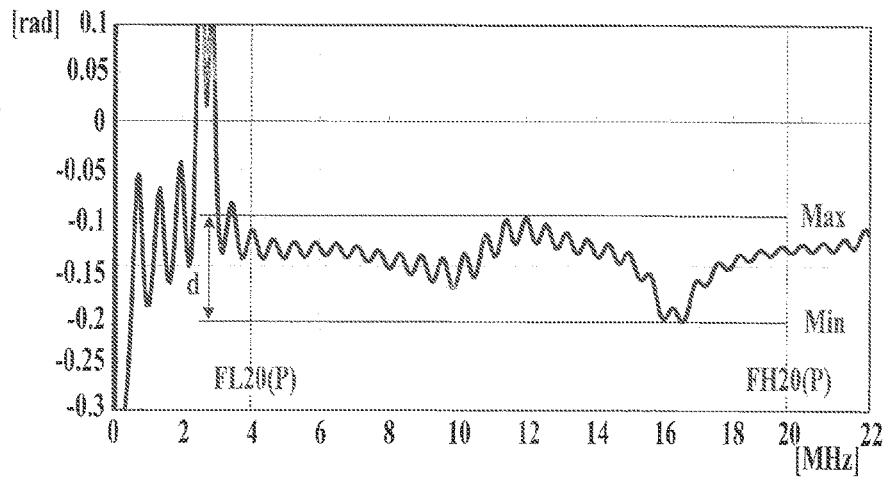

Specifically, for example, when the frequency analysis of the driving waveform of FIG. 7A is performed, the power spectrum illustrated in FIG. 7B is obtained. The group delay characteristics of the driving waveform of FIG. 7A becomes that illustrated in FIG. 7C. The frequency band at −20 dB of this driving waveform was within a range from the lower limit frequency (FL20 (V)) to the upper limit frequency (FH20 (V)), as illustrated in FIG. 7B. When the pulse signal having such driving waveform is applied to the ultrasound probe having the transmission/reception band characteristics of FIG. 3A, it is important that the difference (d) between the maximum value and the minimum value of the group delay amounts in the frequency band where the frequency band (the range from the lower limit frequency (FL20 (P)) to the upper limit frequency (FH20 (P)), namely, 3.99 to 19.72 MHz in this embodiment) contained in the transmission/reception frequency band at −20 dB of the ultrasound probe and the frequency band (the range from the lower limit frequency (FL20 (V)) to the upper limit frequency (FH20 (V))) at −20 dB of the driving waveform illustrated in FIG. 7B overlap each other. The smaller the difference is, the more preferable the obtained reception signal is, because cancellation among the multiple kinds of the higher harmonic waves hardly occurs and an intended distance resolution can be obtained. Preferably, the difference between the maximum value and the minimum value is 0.15 radian or less. In the above case, the frequency band where the frequency band contained in the transmission/reception frequency band at −20 dB of the ultrasound probe and the frequency band at −20 dB of the driving waveform overlap each other corresponds to the frequency band contained in the transmission/reception frequency band at −20 dB of the ultrasound probe. Therefore, the difference (d) between the maximum value and the minimum value of the group delay amounts within this range is preferably small as much as possible.

The group delay characteristics can be controlled by appropriately changing the driving waveform. It may be group delay characteristics according to which the standard deviation in the frequency band where the frequency band contained in the transmission/reception frequency band at −20 dB of the ultrasound probe 2 and the frequency band at −20 dB of the pulse signal overlap each other is 0.025 or less. The standard deviation can be obtained by the above-described method.

In this embodiment, more preferably, the ultrasound probe 2 and the driving waveform are set so that the difference between the maximum value and the minimum value of the group delays is 0.15 radian or less, the group delays being obtained by totaling the group delay of the ultrasound probe 2 obtained as described above and the group delay of the driving waveform in the pulse signal to be given to the ultrasound probe 2, in the frequency band where the frequency band contained in the transmission/reception frequency band at −20 dB of the ultrasound probe 2 and the frequency band at −20 dB of the driving waveform in the pulse signal overlap each other. Incidentally, at least one of the group delay characteristics of the ultrasound probe 2 and of the driving waveform does not have to meet the above-described condition, as long as the totalized group delay meets the above-described condition.

Incidentally, in the case of outputting the pulse signal of the driving waveform in which the frequency bandwidth where the frequency band contained in the transmission/reception frequency band at −20 dB of the ultrasound probe 2 and the frequency band at −20 dB of the driving waveform of the pulse signal overlap each other covers 70% or more of the frequency bandwidth at −20 dB of the ultrasound probe 2, the broadband ultrasound can be transmitted/received, and accordingly the effects of the present invention can be suitably obtained. According to the above-described condition, the frequency bandwidth where the frequency band contained in the transmission/reception frequency band at −20 dB of the ultrasound probe 2 and the frequency band at −20 dB of the driving waveform in the pulse signal overlap each other covers 100% of the frequency bandwidth at −20 dB of the ultrasound probe 2, and therefore the excellent broadband ultrasound can be transmitted/received.

In this embodiment, the driving waveform of the pulse signal to be output is made as the driving waveform of the period of 1.5 or more, which can scatter the output voltage of the pulse signal in a time axis direction. As a result, the maximum output voltage can be made small, and the costs can be reduced. Alternatively, the period of the driving waveform may be less than 1.5.

Figure 8:
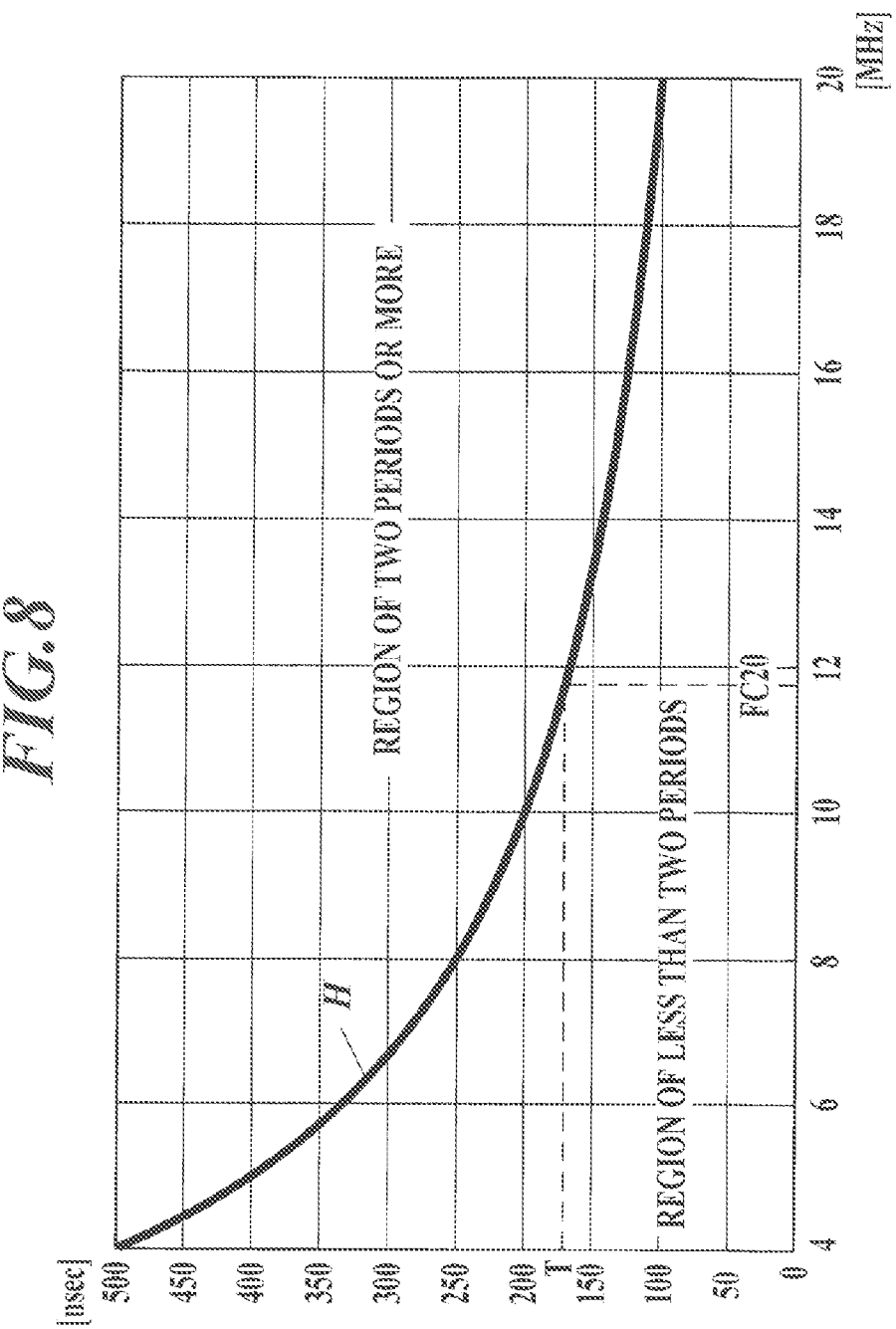
FIG. 8 is a graph illustrating a relationship between a frequency and a time corresponding to two periods of the frequency.

In this embodiment, the pulse duration of the pulse signal to be output is preferably set to the time corresponding to two period at the center frequency of the transmission/reception frequency band at −20 dB of the ultrasound probe 2 or more, which can scatter the output voltage of the pulse signal in the time axis direction. FIG. 8 illustrates a relationship between the frequency and the time corresponding to two period of the frequency. In this embodiment, preferably the pulse duration is set to be equal to or more than the time represented as curve H in FIG. 8H. For example, since the center frequency (FC20) in the transmission/reception frequency band at −20 dB of the ultrasound probe 2 having the transmission/reception band characteristics of FIG. 3A is 11.86 MHz, the pulse duration is preferably set to be equal or more than time T corresponding to this value. Alternatively, the pulse duration may be set to be less than the time corresponding to two period at the center frequency in the transmission/reception frequency band at −20 dB of the ultrasound probe 2.

This embodiment can execute the pulse inversion method to extract higher harmonic components to be described later. Concretely, when executing the pulse inversion method, the transmission section 12 can transmit the first pulse signal, and the second pulse signal obtained by inverting the polarity of the first pulse signal, to the same scanning line with a predetermined time interval. At that time, the transmission section 12 may transmit the second pulse signal obtained by inverting the polarity of the first pulse signal by making at least one of duty ratios different from other duty ratios of the first pulse signal, the second pulse signal having an asymmetric relationship with the first pulse signal. The asymmetric relationship between the waveforms means that one waveform is not linearly symmetrical, and is not symmetrical about a point, with another waveform. In other words, it means that a shape of one waveform does not match (is not symmetrical) a shape of another waveform even when the one waveform is subjected to time reversal or polarity inversion. The second pulse signal can be obtained also by making the first pulse signal subjected to time reversal. Thus, the transmission section 12 of this embodiment can output the pulse signals having different driving waveforms to the same scanning line with a predetermined time interval multiple times.

As illustrated in FIG. 2, the reception section 13 is a circuit which receives the electrical reception signals from the ultrasound probe 2 via the cable 3 according to the control by the control section 18. The reception section 13 is equipped with, for example, an amplifier, an A/D converting circuit and a phase regulating adder circuit. The amplifier is a circuit to amplify the reception signal at a predetermined amplification factor that is previously set, for each of the individual paths corresponding to the respective oscillators 2A. The A/D converting circuit is a circuit to make the amplified reception signal subjected to Analog/Digital (A/D) conversion. The phase regulating adder circuit is a circuit to apply the delay time to the reception signal subjected to the A/D conversion, for each of the individual paths corresponding to the respective oscillators 2A, to regulate the time phase, and adds (phasing addition) these reception signals to generate sound ray data.

The image generating section 14 performs an envelope detection processing and/or logarithmic amplification to the sound ray data output from the reception section 13, and performs luminance conversion by gain adjustment or the like, so as to generate B mode image data. Thus, the B mode image data represents the intensity of the reception signal with luminance. The B mode image data generated in the image generating section 14 is transmitted to the image processing section 15. The image generating section 14 is also equipped with a higher harmonic component extracting section 14A.

The higher harmonic component extracting section 14A extracts the higher harmonic components from the reception signal output from the reception section 13 by executing the pulse inversion method. In this embodiment, the higher harmonic component extracting section 14A extracts the higher harmonic components including mainly the secondary higher harmonic wave. The secondary higher harmonic components can be extracted by adding (totaling) the reception signals obtained from the reflected ultrasounds corresponding to two transmission ultrasounds, respectively, generated from the above-described first pulse signal and the second pulse signal, removing the basic wave components contained in the reception signals, and performing a filter processing.

The image processing section 15 is equipped with an image memory section 15A composed of a semiconductor memory such as a Dynamic Random Access Memory (DRAM). The image processing section 15 stores the B mode image data output from the image generating section 14 in a unit of frames in the image memory section 15A. The image data in the frame unit are sometimes referred to as ultrasound image data or frame image data. The image processing section 15 suitably reads out the ultrasound image data stored in the image memory section 15A to output the ultrasound image data to the DSC 16.

The DSC 16 converts the ultrasound image data received from the image processing section 15 into an image signal in a scanning system of a television signal, and outputs the image signal to the display section 17.

The display section 17 may be a display device such as a Liquid Crystal Display (LCD), Cathode-Ray Tube (CRT) display, organic Electronic Luminescence (EL) display, inorganic EL display and plasma display. The display section 17 displays the ultrasound image on a display screen according to the image signal output from the DSC 16.

The control section 18 is equipped with, for example, a Central Processing Unit (CPU), Read Only Memory (ROM) and Random Access Memory (RAM), and reads out the various processing programs such as a system program stored in the ROM to expand the programs in the RAM, and centrally controls the sections of the ultrasound image diagnosis apparatus S according to the expanded programs.

The ROM is composed of, for example, a nonvolatile memory such as semiconductor, and stores the system program applicable for the ultrasound image diagnosis apparatus S, various processing programs executable on the system program, and various pieces of data. These programs are stored in the form of program codes readable by the computers, and the CPU successively executes the operations according to the program codes.

The RAM forms a work area in which various programs executed by the CPU and data related to these programs are temporarily stored.

EXAMPLES

Hereinafter examples of the present invention will be described in more detail. It is needless to say that the present invention is not limited to these examples.

First, ultrasound probes A to D used in the examples and comparative examples as the ultrasound probes 2 will be described.

<Ultrasound Probe A>

Figure 9A:
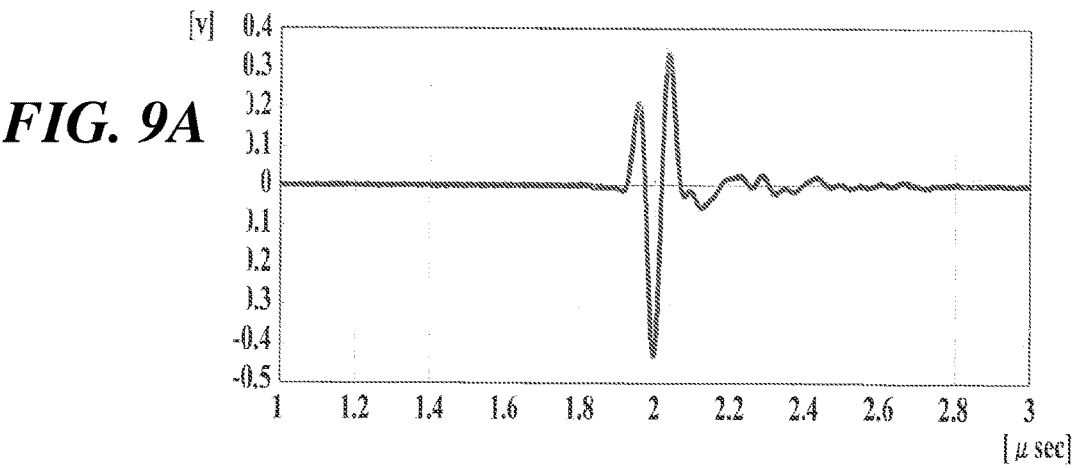
FIGS. 9A, 9B and 9C are diagrams each illustrating characteristics of an ultrasound probe A.
Figure 9B:
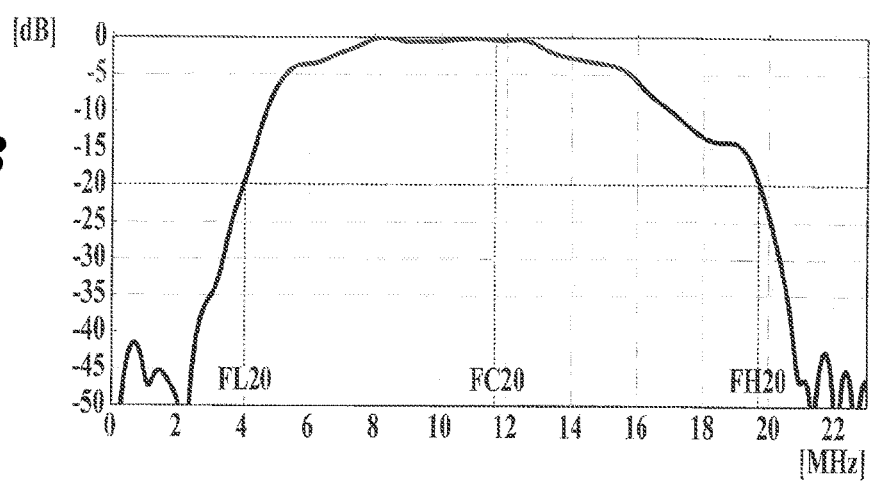
Figure 9C:
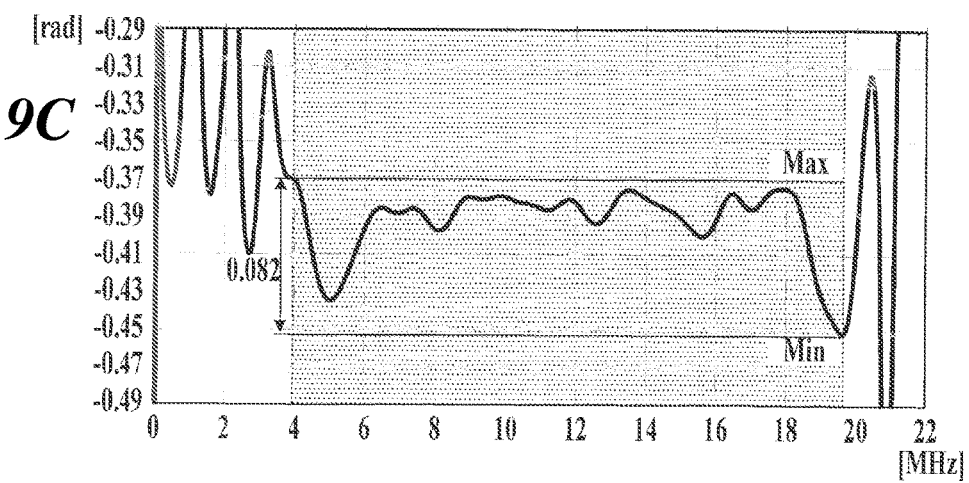

The ultrasound probe A having characteristics illustrated in FIGS. 9A, 9B and 9C was used. FIG. 9A illustrates impulse response characteristics at the time when an impulse signal was given to the ultrasound probe A, FIG. 9B illustrates the transmission/reception band characteristics of the ultrasound probe A, and FIG. 9C illustrates the group delay characteristics obtained from a phase difference, for each frequency, between the impulse signal given to the ultrasound probe A and the reception signal obtained as a result of the transmission/reception of the ultrasound executed by the impulse signal. In FIG. 9A, the horizontal axis indicates the time, and the vertical axis indicates the voltage. In FIG. 9B, the horizontal axis indicates the frequency, and the vertical axis indicates the sensitivity. In FIG. 9C, the horizontal axis indicates the frequency, and the vertical axis indicates the group delay amount.

The group delay characteristics was measured while a plate for making the ultrasound from the ultrasound probe reflected thereon was installed underwater so that the surface of the plate was perpendicular to the ultrasound probe. The plate was placed at a position of so-called Flat Plate Focus, namely, at a position where the maximum value of the intensity of the ultrasound can be obtained because the ultrasounds were converged at the position by the acoustic lens included in the ultrasound probe. The impulse signal given to the ultrasound probe was an impulse signal having a substantially flat frequency characteristics and a substantially flat group delay characteristics. One (1) element of the ultrasound probe was driven by an Olympus Model 5900PR pulser receiver in a transmission mode of 1 uJ, a frequency analysis was performed to the electrical reception signal at the time when the ultrasound was transmitted/received to/from the SUS plate placed at the Flat Plate Focus position in a degassed water so as to obtain the phase characteristics, and the phase characteristics was differentiated so as to obtain the group delay characteristics. The same measurements of the group delay characteristics were performed also to the ultrasound probes to be described later.

As illustrated in FIG. 9B, according to the transmission/reception band characteristics of the ultrasound probe A, the lower limit frequency (FL20) was 3.99 MHz, the upper limit frequency (FH20) was 19.72 MHz, the center frequency (FC20) was 11.86 MHz, and the fractional bandwidth at −20 dB of transmission/reception was 133%. The difference between the maximum value and the minimum value of the group delay amounts in the transmission/reception bandwidth (FL20: 3.99 MHz to FH20: 19.72 MHz) at −20 dB of the ultrasound probe A was 0.082, and the standard deviation of the group delay amounts in this transmission/reception bandwidth was 0.0184.

<Ultrasound Probe B>

Figure 10A:
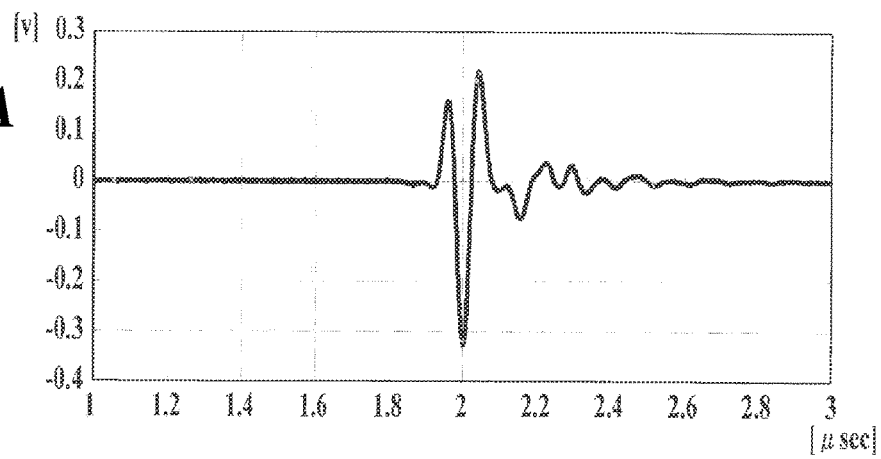
FIGS. 10A, 10B and 10C are diagrams each illustrating characteristics of an ultrasound probe B.
Figure 10B:
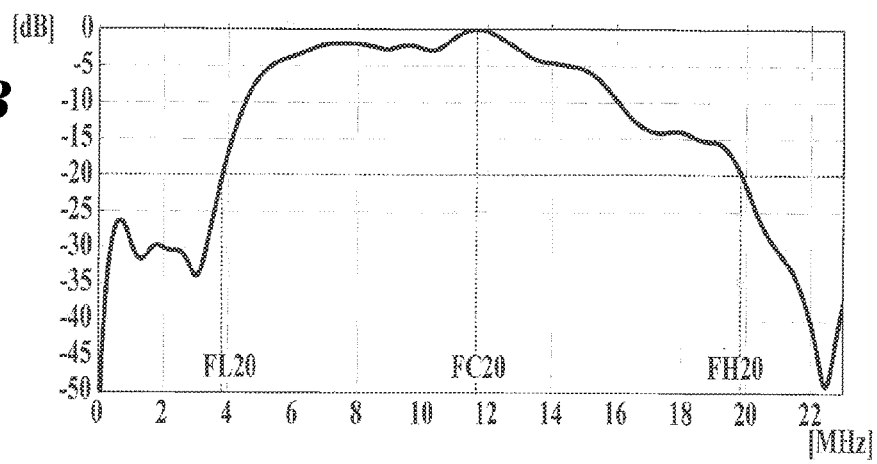
Figure 10C:
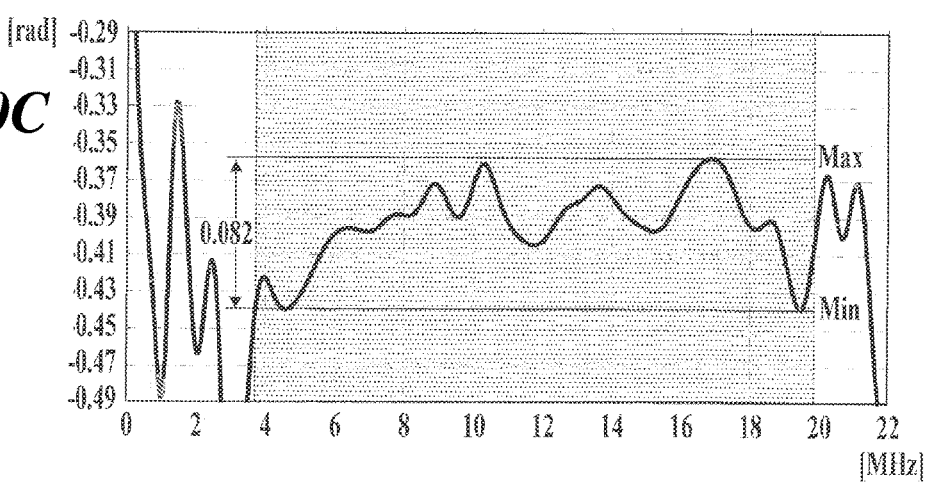

The ultrasound probe B having characteristics illustrated in FIGS. 10A, 10B and 10C was used. FIG. 10A illustrates an impulse response characteristics at the time when an impulse signal was given to the ultrasound probe B, FIG. 10B illustrates the transmission/reception band characteristics of the ultrasound probe B, and FIG. 10C illustrates the group delay characteristics obtained from a phase difference, for each frequency, between the impulse signal given to the ultrasound probe B and the reception signal obtained as a result of the transmission/reception of the ultrasound executed by the impulse signal. In FIG. 10A, the horizontal axis indicates the time, and the vertical axis indicates the voltage. In FIG. 10B, the horizontal axis indicates the frequency, and the vertical axis indicates the sensitivity. In FIG. 10C, the horizontal axis indicates the frequency, and the vertical axis indicates the group delay amount.

As illustrated in FIG. 10B, according to the transmission/reception band characteristics of the ultrasound probe B, the lower limit frequency (FL20) was 3.82 MHz, the upper limit frequency (FH20) was 19.86 MHz, the center frequency (FC20) was 11.84 MHz, and the fractional bandwidth at −20 dB of the transmission/reception was 135%. The difference between the maximum value and the minimum value of the group delay amounts in the transmission/reception bandwidth (FL20: 3.82 MHz to FH20: 19.86 MHz) at −20 dB of the ultrasound probe B was 0.082, and the standard deviation of the group delay amounts in this transmission/reception bandwidth was 0.0198.

<Ultrasound Probe C>

Figure 11A:
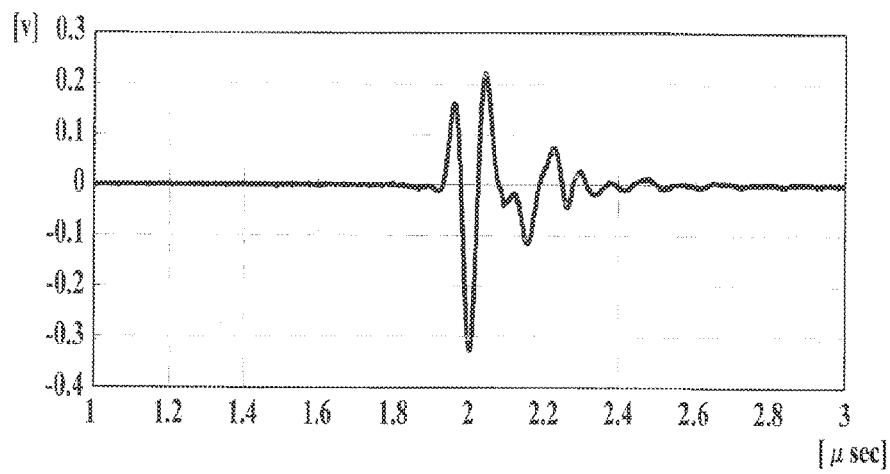
FIGS. 11A, 11B and 11C are diagrams each illustrating characteristics of an ultrasound probe C.
Figure 11B:
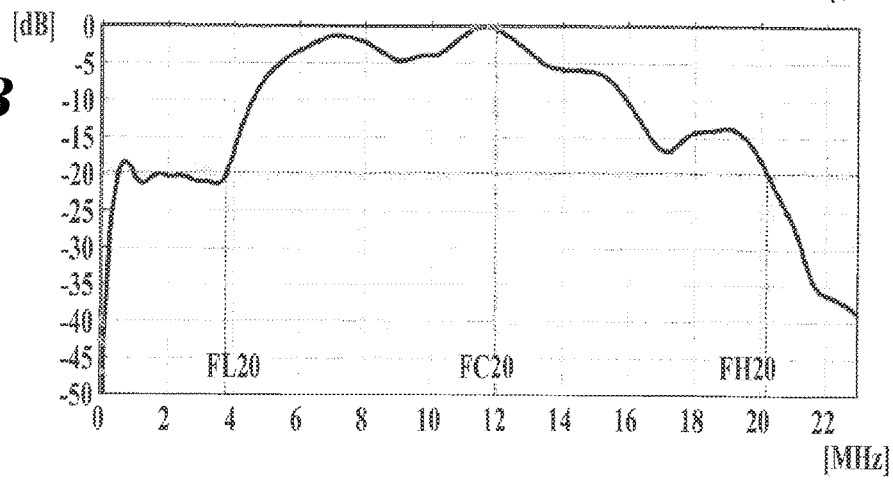
Figure 11C:
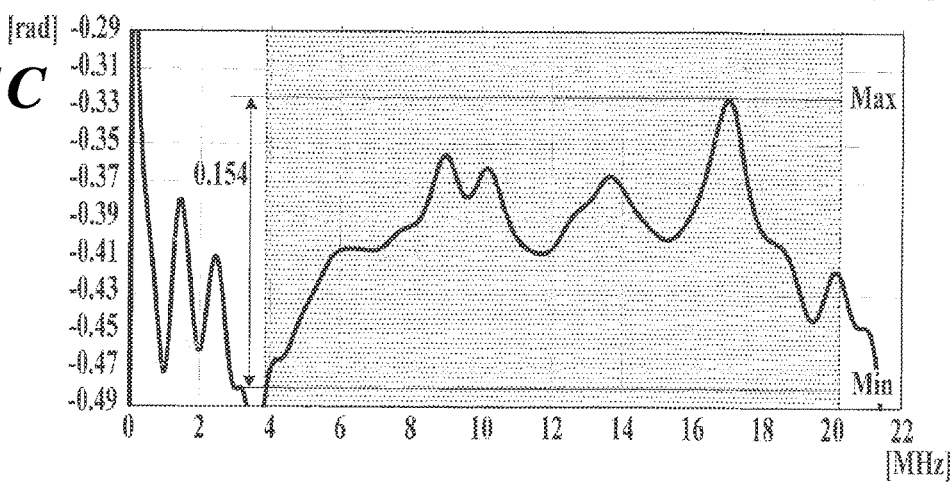

The ultrasound probe C having characteristics illustrated in FIGS. 11A, 11B and 11C was used. FIG. 11A illustrates an impulse response characteristics at the time when an impulse signal was given to the ultrasound probe C, FIG. 11B illustrates the transmission/reception band characteristics of the ultrasound probe C, and FIG. 11C illustrates the group delay characteristics obtained from a phase difference, for each frequency, between the impulse signal given to the ultrasound probe C and the reception signal obtained as a result of the transmission/reception of the ultrasound executed by the impulse signal. In FIG. 11A, the horizontal axis indicates the time, and the vertical axis indicates the voltage. In FIG. 11B, the horizontal axis indicates the frequency, and the vertical axis indicates the sensitivity. In FIG. 11C, the horizontal axis indicates the frequency, and the vertical axis indicates the group delay amount.

As illustrated in FIG. 11B, according to the transmission/reception band characteristics of the ultrasound probe C, the lower limit frequency (FL20) was 3.75 MHz, the upper limit frequency (FH20) was 20.23 MHz, the center frequency (FC20) was 11.99 MHz, and the fractional bandwidth at −20 dB of the transmission/reception was 137%. The difference between the maximum value and the minimum value of the group delay amounts in the transmission/reception bandwidth (FL20: 3.75 MHz to FH20: 20.23 MHz) at −20 dB of the ultrasound probe C was 0.154, and the standard deviation of the group delay amounts in this transmission/reception bandwidth was 0.0287.

<Ultrasound Probe D>

Figure 12A:
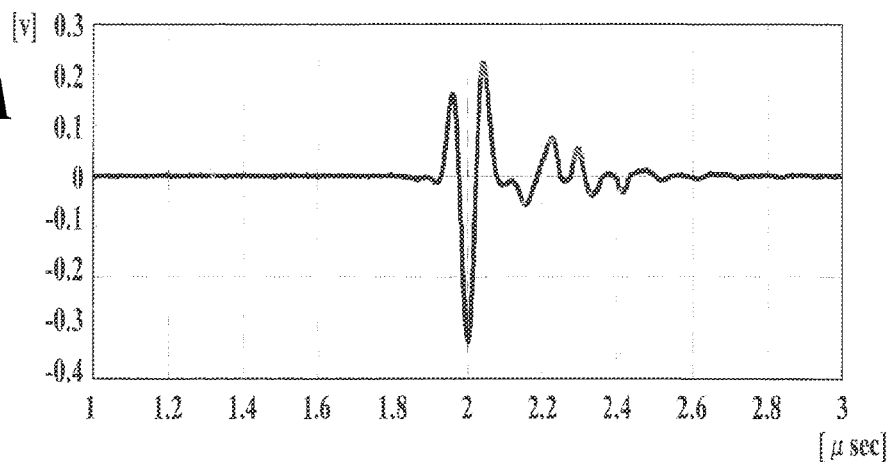
FIGS. 12A, 12B and 12C are diagrams each illustrating characteristics of an ultrasound probe D.
Figure 12B:
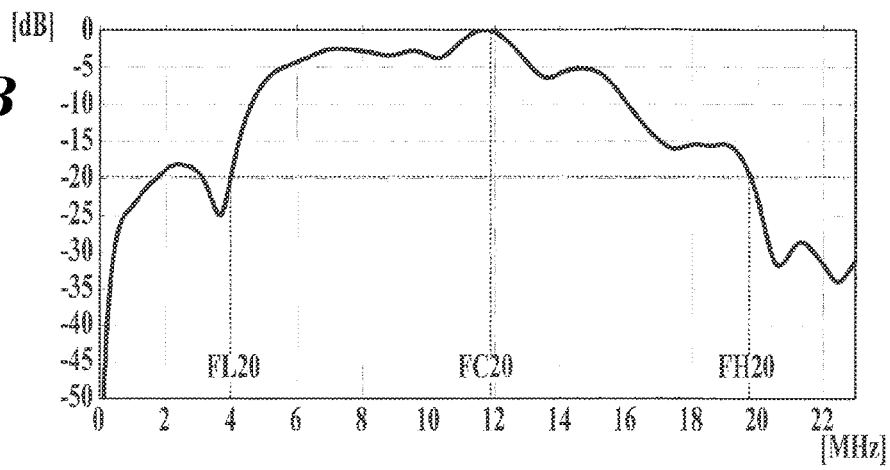
Figure 12C:
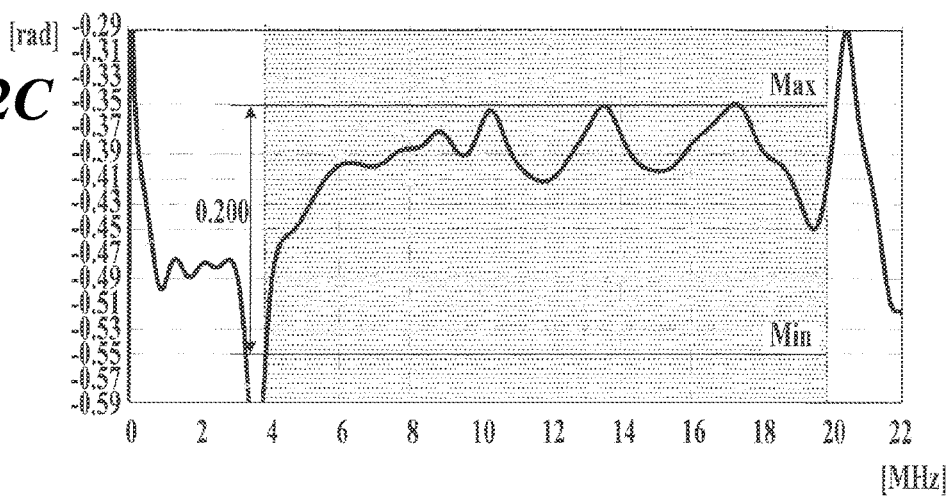

The ultrasound probe D having characteristics illustrated in FIGS. 12A, 12B and 12C was used. FIG. 12A illustrates an impulse response characteristics at the time when an impulse signal was given to the ultrasound probe D, FIG. 12B illustrates the transmission/reception band characteristics of the ultrasound probe D, and FIG. 12C illustrates the group delay characteristics obtained from a phase difference, for each frequency, between the impulse signal given to the ultrasound probe D and the reception signal obtained as a result of the transmission/reception of the ultrasound executed by the impulse signal. In FIG. 12A, the horizontal axis indicates the time, and the vertical axis indicates the voltage. In FIG. 12B, the horizontal axis indicates the frequency, and the vertical axis indicates the sensitivity. In FIG. 12C, the horizontal axis indicates the frequency, and the vertical axis indicates the group delay amount.

As illustrated in FIG. 12B, according to the transmission/reception band characteristics of the ultrasound probe D, the lower limit frequency (FL20) was 3.96 MHz, the upper limit frequency (FH20) was 19.78 MHz, the center frequency (FC20) was 11.87 MHz, and the fractional bandwidth at −20 dB of the transmission/reception was 133%. The difference between the maximum value and the minimum value of the group delay amounts in the transmission/reception bandwidth (FL20: 3.96 MHz to FH20: 19.78 MHz) at −20 dB of the ultrasound probe D was 0.200, and the standard deviation of the group delay amounts in this transmission/reception bandwidth was 0.0301.

Example 1

The above-described ultrasound probe A was used as the ultrasound probe 2.

Figure 13A:
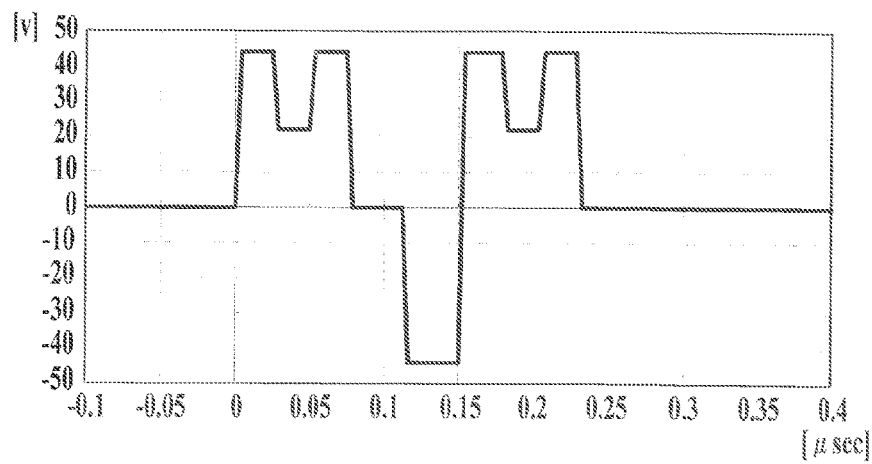
FIGS. 13A, 13B and 13C are diagrams each illustrating characteristics of a driving waveform A.
Figure 13B:
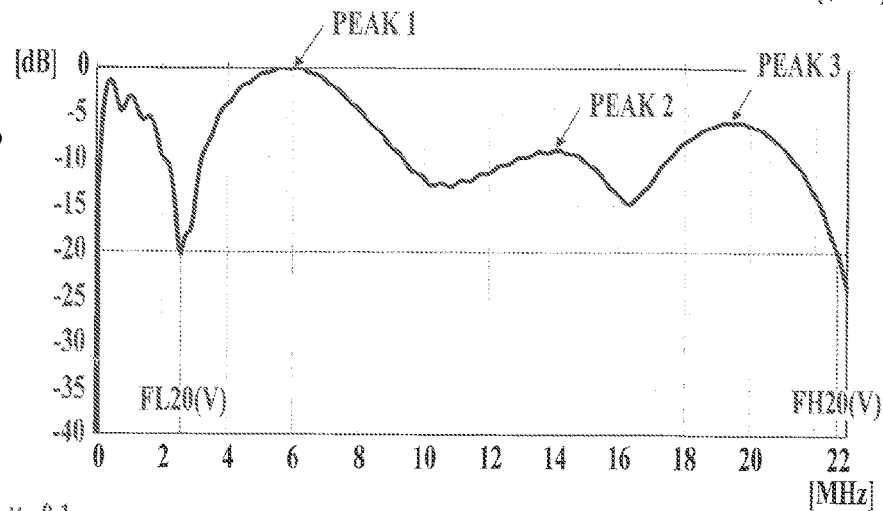
Figure 13C:
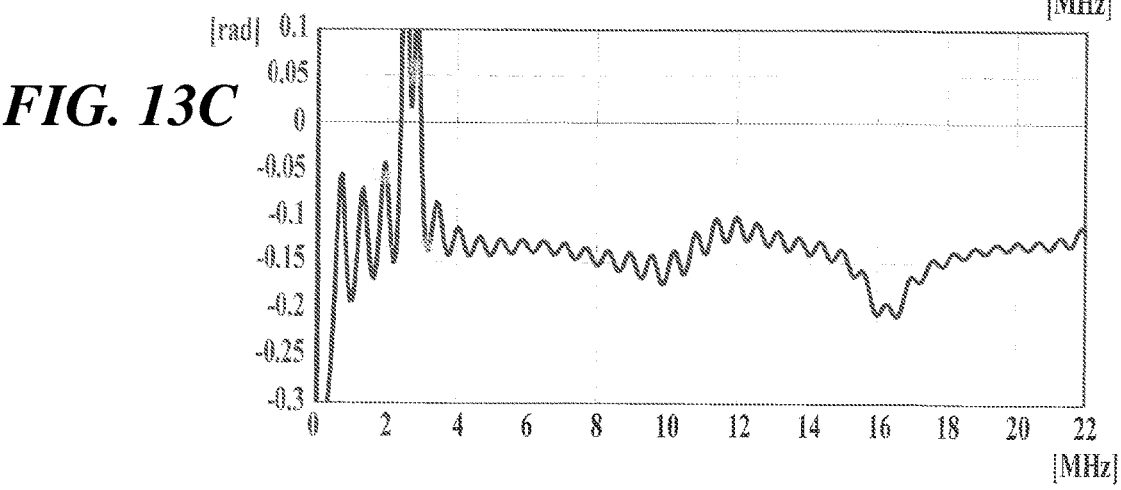

The first pulse signal output from the transmission section 12 was the driving signal of the driving waveform A illustrated in FIG. 13A. FIG. 13B illustrates the frequency power spectrum obtained by the frequency analysis of the driving waveform A. FIG. 13C illustrates the group delay characteristics of the driving waveform A. In FIG. 13A, the horizontal axis indicates the time, and the vertical axis indicates the voltage. In FIG. 13B, the horizontal axis indicates the frequency, and the vertical axis indicates the signal intensity. In FIG. 13C, the horizontal axis indicates the frequency, and the vertical axis indicates the group delay amount.

The group delay characteristics was measured by measuring a voltage waveform at the time when a probe receptacle included in the ultrasound image diagnosis apparatus body was terminated with a resistance of 50Ω and driven, then performing the frequency analysis to this voltage waveform to obtain the phase characteristics, and differentiating the phase characteristics. The same measurements of the group delay characteristics were performed to the driving waveforms to be described later.

The driving waveform A had three intensity peaks in the transmission/reception frequency band (3.99 MHz to 19.72 MHz) at −20 dB of the ultrasound probe A, and one of the intensity peaks located on the low frequency side with respect to the center frequency (FC20: 11.86 MHz) in the transmission/reception frequency band at −20 dB of the ultrasound probe A, and other two intensity peaks located on the high frequency side with respect to the center frequency (FC20: 11.86 MHz) in the transmission/reception frequency band at −20 dB of the ultrasound probe A.

Figure 24:
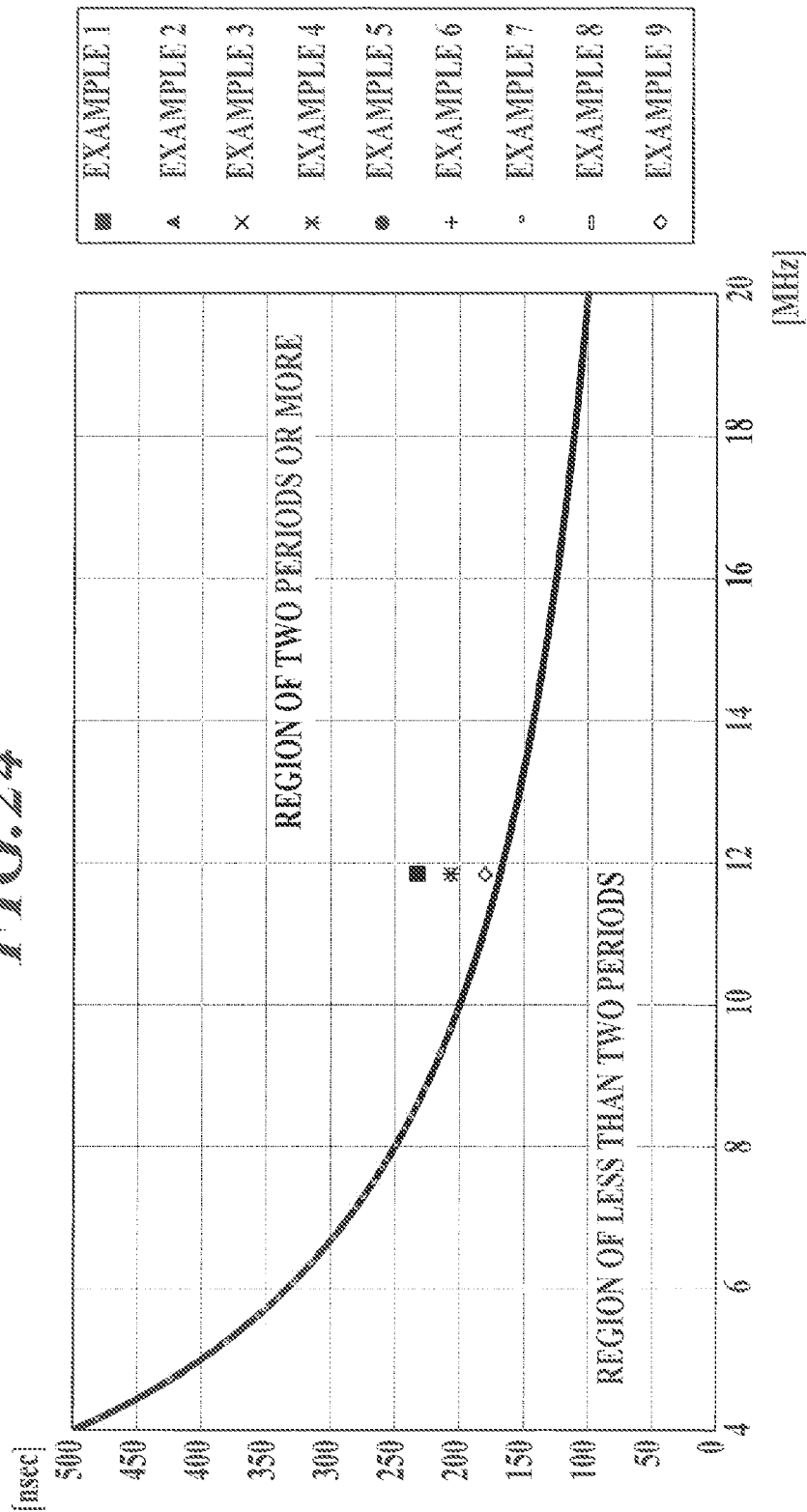
FIG. 24 is a graph illustrating a relationship between a frequency and a time corresponding to two periods of the frequency.

The pulse duration of the driving waveform A was 233 ns, which corresponded to 2.76 periods at the center frequency (FC20: 11.86 MHz) in the transmission/reception frequency band at −20 dB of the ultrasound probe A. In other words, the pulse duration of the driving waveform A was equal to or more than the time corresponding to two periods at the center frequency (FC20: 11.86 MHz) in the transmission/reception frequency band at −20 dB of the ultrasound probe A (see FIG. 24).

The frequency band where the frequency band included in the transmission/reception frequency band at −20 dB of the ultrasound probe A and the frequency band at −20 dB of the driving waveform A overlap each other corresponds to the transmission/reception frequency band at −20 dB of the ultrasound probe A, which was within the range from the lower limit frequency of 3.99 MHz (FL20) to the upper limit frequency of 19.72 MHz (FH20). A cover ratio of the ultrasound probe A of this frequency bandwidth over the transmission/reception frequency bandwidth at −20 dB was 100%.

The difference between the maximum value and the minimum value of the group delays of the driving waveform A in the frequency band where the frequency band included in the transmission/reception frequency band at −20 dB of the ultrasound probe A and the frequency band at −20 dB of the driving waveform A overlap each other was 0.107 radian. The standard deviation of the group delays of the driving waveform A in the frequency band where the frequency band included in the transmission/reception frequency band at −20 dB of the ultrasound probe A and the frequency band at −20 dB of the driving waveform A overlap each other was 0.0208.

Figure 21:
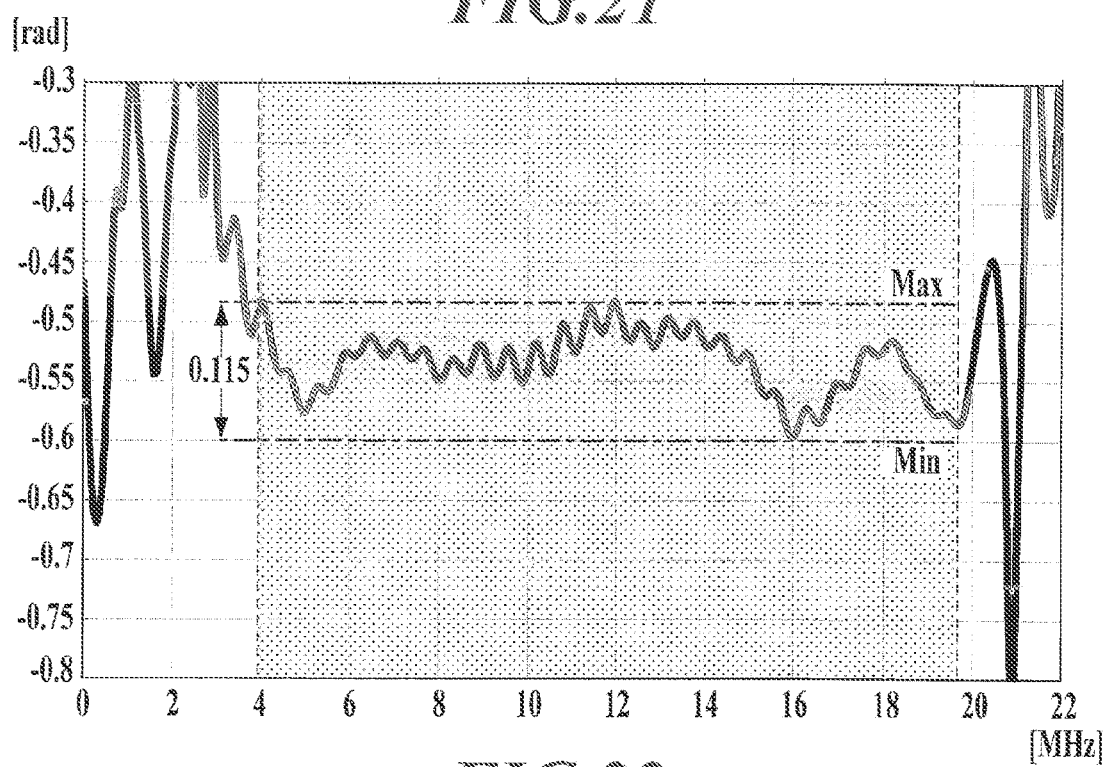
FIG. 21 is a diagram illustrating a totaling result of a group delay of the ultrasound probe A and a group delay of the driving waveform A.

The difference between the maximum value and the minimum value of the totaling values of the group delay of the ultrasound probe A obtained as described above and the group delay of the driving waveform A, in the frequency band where the frequency band included in the transmission/reception frequency band at −20 dB of the ultrasound probe A and the frequency band at −20 dB of the driving waveform A overlap each other, was 0.115. FIG. 21 illustrates the totaling result of the group delay of the ultrasound probe A and the group delay of the driving waveform A.

The second pulse signal was the driving signal of the driving waveform obtained by inverting the polarity of the driving waveform A.

Example 2

The above-described ultrasound probe B was used as the ultrasound probe 2.

The first pulse signal output from the transmission section 12 was the driving signal of the driving waveform A same as that of Example 1.

The driving waveform A had three intensity peaks in the transmission/reception frequency band (3.82 MHz to 19.86 MHz) at −20 dB of the ultrasound probe B, and one of the intensity peaks located on the low frequency side with respect to the center frequency (FC20: 11.84 MHz) in the transmission/reception frequency band at −20 dB of the ultrasound probe B, and other two intensity peaks located on the high frequency side with respect to the center frequency (FC20: 11.84 MHz) in the transmission/reception frequency band at −20 dB of the ultrasound probe B.

The pulse duration of the driving waveform A was 233 ns, which corresponded to 2.76 periods at the center frequency (FC20: 11.84 MHz) in the transmission/reception frequency band at −20 dB of the ultrasound probe B. In other words, the pulse duration of the driving waveform A was equal to or more than the time corresponding to two periods at the center frequency (FC20: 11.84 MHz) in the transmission/reception frequency band at −20 dB of the ultrasound probe B (see FIG. 24).

The frequency band where the frequency band included in the transmission/reception frequency band at −20 dB of the ultrasound probe B and the frequency band at −20 dB of the driving waveform A overlap each other corresponds to the transmission/reception frequency band at −20 dB of the ultrasound probe B, which was within the range from the lower limit frequency of 3.82 MHz (FL20) to the upper limit frequency of 19.86 MHz (FH20). A cover ratio of the ultrasound probe B of this frequency bandwidth over the transmission/reception frequency bandwidth at −20 dB was 100%.

The difference between the maximum value and the minimum value of the group delays of the driving waveform A in the frequency band where the frequency band included in the transmission/reception frequency band at −20 dB of the ultrasound probe B and the frequency band at −20 dB of the driving waveform A overlap each other was 0.107 radian. The standard deviation of the group delays of the driving waveform A in the frequency band where the frequency band included in the transmission/reception frequency band at −20 dB of the ultrasound probe B and the frequency band at −20 dB of the driving waveform A overlap each other was 0.0208.

The difference between the maximum value and the minimum value of the totaling value of the group delay of the ultrasound probe B obtained as described above and the group delay of the driving waveform A, in the frequency band where the frequency band included in the transmission/reception frequency band at −20 dB of the ultrasound probe B and the frequency band at −20 dB of the driving waveform A overlap each other, was 0.089.

The second pulse signal was the driving signal of the driving waveform obtained by inverting the polarity of the driving waveform A.

Example 3

The above-described ultrasound probe A was used as the ultrasound probe 2.

The first pulse signal output from the transmission section 12 was the driving signal of the driving waveform A same as that of Example 1.

Figure 15A:
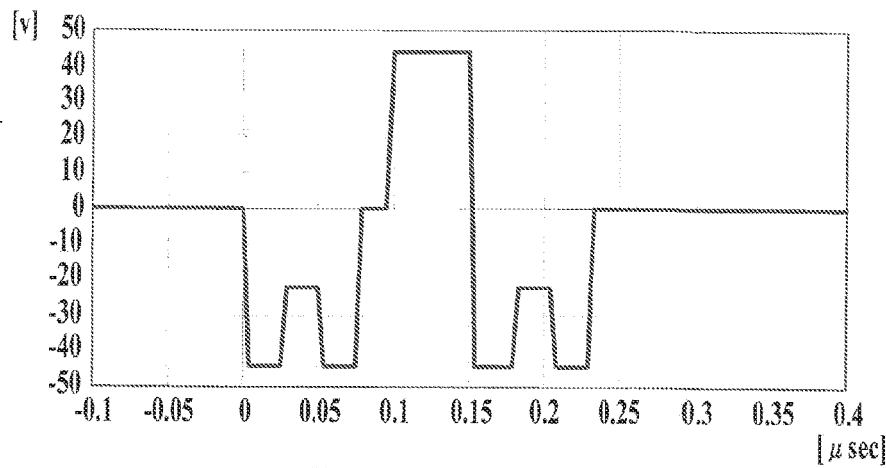
FIGS. 15A, 15B and 15C are diagrams each illustrating characteristics of a driving waveform C.
Figure 15B:
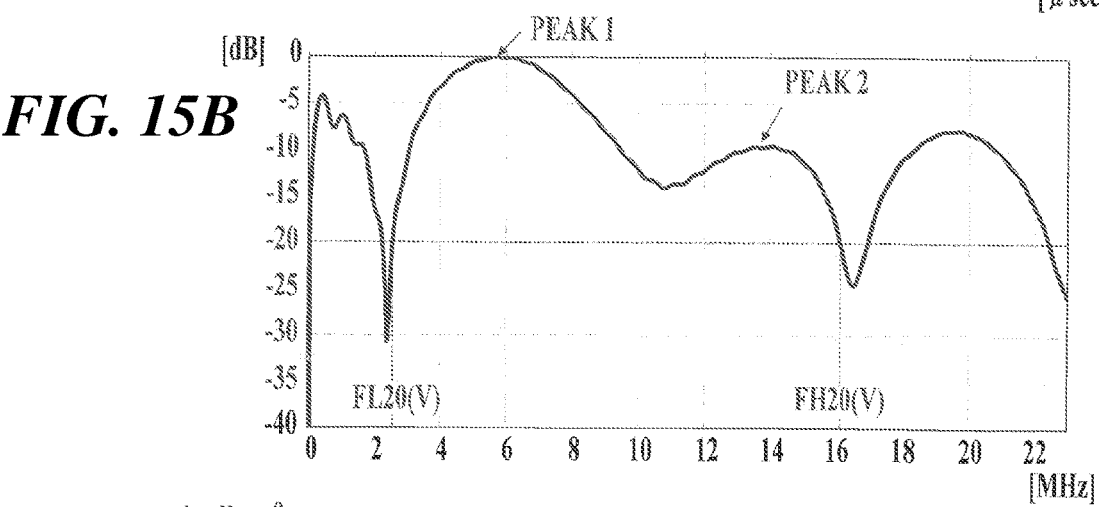
Figure 15C:
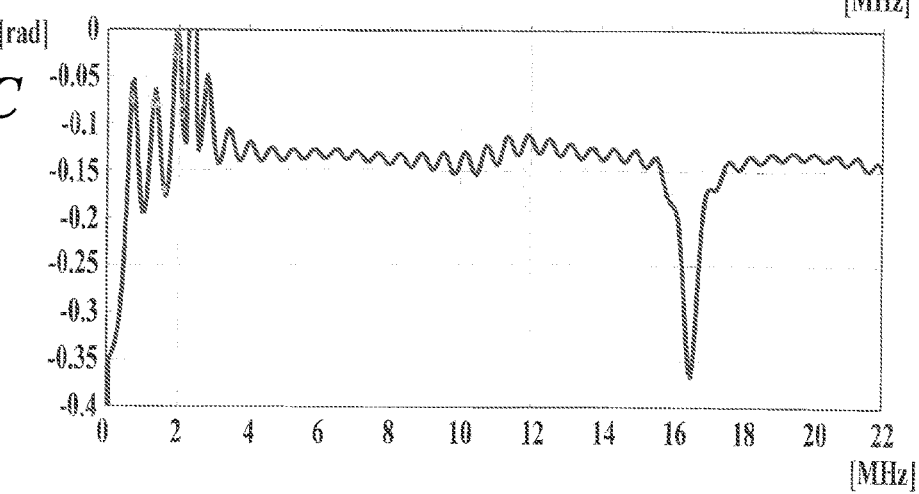

The second pulse signal was the driving signal of the driving waveform C illustrated in FIG. 15A. FIG. 15B illustrates the frequency power spectrum obtained by the frequency analysis of the driving waveform C. FIG. 15C illustrates the group delay characteristics of the driving waveform C. In FIG. 15A, the horizontal axis indicates the time, and the vertical axis indicates the voltage. In FIG. 15B, the horizontal axis indicates the frequency, and the vertical axis indicates the signal intensity. In FIG. 15C, the horizontal axis indicates the frequency, and the vertical axis indicates the group delay amount.

The driving waveform C had two intensity peaks in the transmission/reception frequency band (3.99 MHz to 19.72 MHz) at −20 dB of the ultrasound probe A. One intensity peak located on the low frequency side, and another intensity peak located on the high frequency side, with respect to the center frequency (FC20: 11.86 MHz) in the transmission/reception frequency band at −20 dB of the ultrasound probe A.

The driving waveform C was obtained by inverting the polarity of the driving waveform A by partially changing the duty radios of the driving waveform thereof.

The pulse duration of the driving waveform C was 233 ns, which corresponded to 2.76 periods at the center frequency (FC20: 11.86 MHz) in the transmission/reception frequency band at −20 dB of the ultrasound probe A. In other words, the pulse duration of the driving waveform C was equal to or more than the time corresponding to two periods at the center frequency (FC20: 11.86 MHz) in the transmission/reception frequency band at −20 dB of the ultrasound probe A (see FIG. 24).

The frequency band where the frequency band included in the transmission/reception frequency band at −20 dB of the ultrasound probe A and the frequency band at −20 dB of the driving waveform C overlap each other was within the range from the lower limit frequency (FL20) of 3.99 MHz to the upper limit frequency (FH20) of 16.13 MHz. Concretely, the above upper limit frequency was smaller than the upper limit frequency in the transmission/reception frequency band at −20 dB of the ultrasound probe A, whereas the above lower limit frequency corresponds to the lower limit frequency in the transmission/reception frequency band at −20 dB of the ultrasound probe A. Thus, this frequency band is narrower than the transmission frequency band at −20 dB of the ultrasound probe A. A cover ratio of the ultrasound probe A of this frequency bandwidth over the transmission/reception frequency bandwidth at −20 dB was 77%.

The difference between the maximum value and the minimum value of the group delays of the driving waveform C in the frequency band where the frequency band included in the transmission/reception frequency band at −20 dB of the ultrasound probe A and the frequency band at −20 dB of the driving waveform C overlap each other was 0.079 radian. The standard deviation of the group delays of the driving waveform C in the frequency band where the frequency band included in the transmission/reception frequency band at −20 dB of the ultrasound probe A and the frequency band at −20 dB of the driving waveform C overlap each other was 0.0117.

The difference between the maximum value and the minimum value of the totaling values of the group delay of the ultrasound probe A obtained as described above and the group delay of the driving waveform C, in the frequency band where the frequency band included in the transmission/reception frequency band at −20 dB of the ultrasound probe A and the frequency band at −20 dB of the driving waveform C overlap each other, was 0.087.

Example 4

The above-described ultrasound probe A was used as the ultrasound probe 2.

Figure 14A:
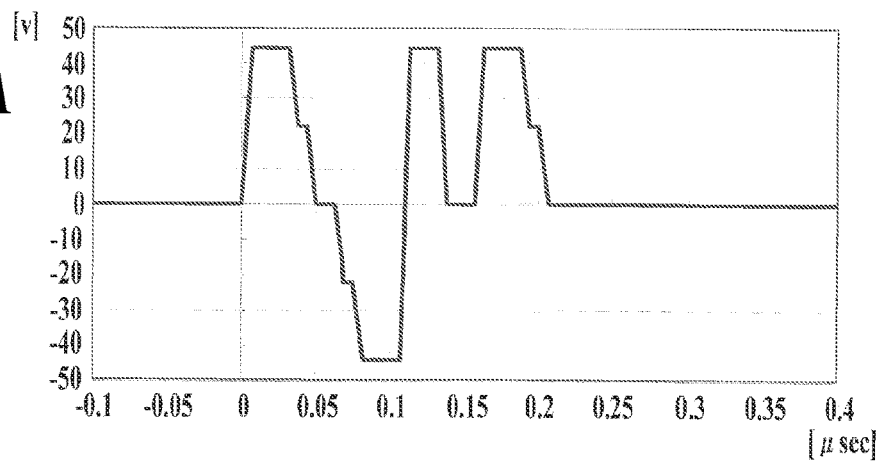
FIGS. 14A, 14B and 14C are diagrams each illustrating characteristics of a driving waveform B.
Figure 14B:
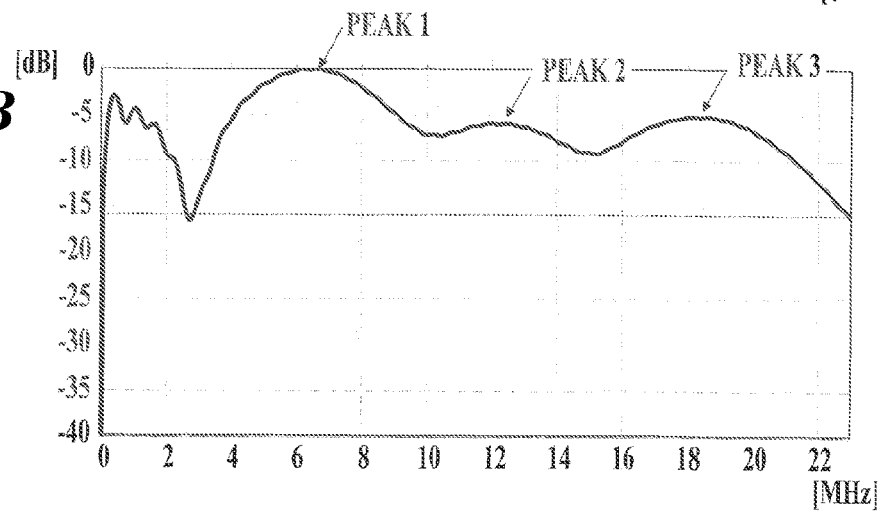
Figure 14C:
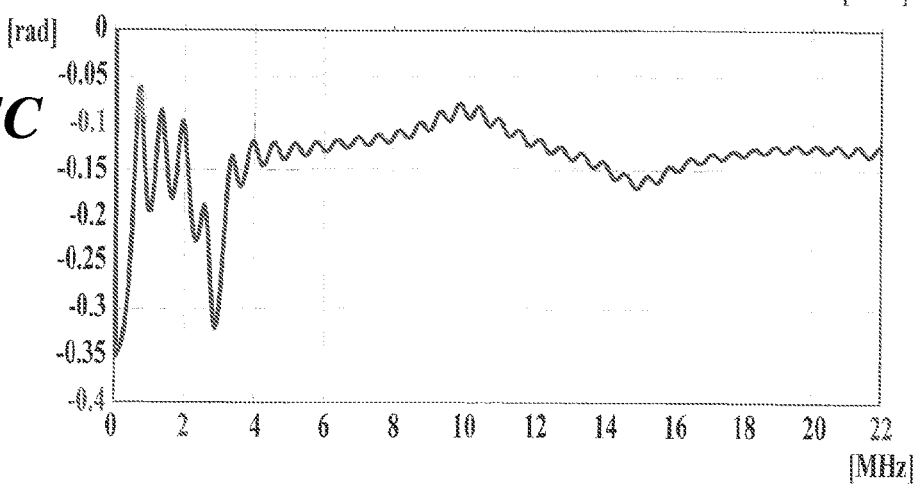

The first pulse signal output from the transmission section 12 was the driving signal of the driving waveform B illustrated in FIG. 14A. FIG. 14B illustrates the frequency power spectrum obtained by the frequency analysis of the driving waveform B. FIG. 14C illustrates the group delay characteristics of the driving waveform B. In FIG. 14A, the horizontal axis indicates the time, and the vertical axis indicates the voltage. In FIG. 14B, the horizontal axis indicates the frequency, and the vertical axis indicates the signal intensity. In FIG. 14C, the horizontal axis indicates the frequency, and the vertical axis indicates the group delay amount.

The driving waveform B had three intensity peaks in the transmission/reception frequency band (3.99 MHz to 19.72 MHz) at −20 dB of the ultrasound probe A, and one of the intensity peaks located on the low frequency side with respect to the center frequency (FC20: 11.86 MHz) in the transmission/reception frequency band at −20 dB of the ultrasound probe A, and other two intensity peaks located on the high frequency side with respect to the center frequency (FC20: 11.86 MHz) in the transmission/reception frequency band at −20 dB of the ultrasound probe A.

The pulse duration of the driving waveform B was 207 ns, which corresponded to 2.45 periods at the center frequency (FC20: 11.86 MHz) of the transmission/reception frequency band at −20 dB of the ultrasound probe A. In other words, the pulse duration of the driving waveform B was equal to or more than the time corresponding to two periods at the center frequency (FC20: 11.86 MHz) of the transmission/reception frequency band at −20 dB of the ultrasound probe A (see FIG. 24).

The frequency band where the frequency band included in the transmission/reception frequency band at −20 dB of the ultrasound probe A and the frequency band at −20 dB of the driving waveform B overlap each other corresponds to the transmission/reception frequency band at −20 dB of the ultrasound probe A, which was within the range from the lower limit frequency of 3.99 MHz (FL20) to the upper limit frequency of 19.72 MHz (FH20). A cover ratio of the ultrasound probe A of this frequency bandwidth over the transmission/reception frequency bandwidth at −20 dB was 100%.

The difference between the maximum value and the minimum value of the group delays of the driving waveform B in the frequency band where the frequency band included in the transmission/reception frequency band at −20 dB of the ultrasound probe A and the frequency band at −20 dB of the driving waveform B overlap each other was 0.092 radian. The standard deviation of the group delays of the driving waveform B in the frequency band where the frequency band included in the transmission/reception frequency band at −20 dB of the ultrasound probe A and the frequency band at −20 dB of the driving waveform B overlap each other was 0.0195.

The difference between the maximum value and the minimum value of the totaling values of the group delay of the ultrasound probe A obtained as described above and the group delay of the driving waveform B, in the frequency band where the frequency band included in the transmission/reception frequency band at −20 dB of the ultrasound probe A and the frequency band at −20 dB of the driving waveform B overlap each other, was 0.120.

The second pulse signal was the driving signal of the driving waveform obtained by inverting the polarity of the driving waveform B.

Example 5

The above-described ultrasound probe A was used as the ultrasound probe 2.

The first pulse signal output from the transmission section 12 was the driving signal of the driving waveform C described by referring to FIGS. 15A, 15B and 15C.

The second pulse signal was the driving signal of the driving waveform obtained by inverting the polarity of the driving waveform C.

Example 6

The above-described ultrasound probe A was used as the ultrasound probe 2.

Figure 16A:
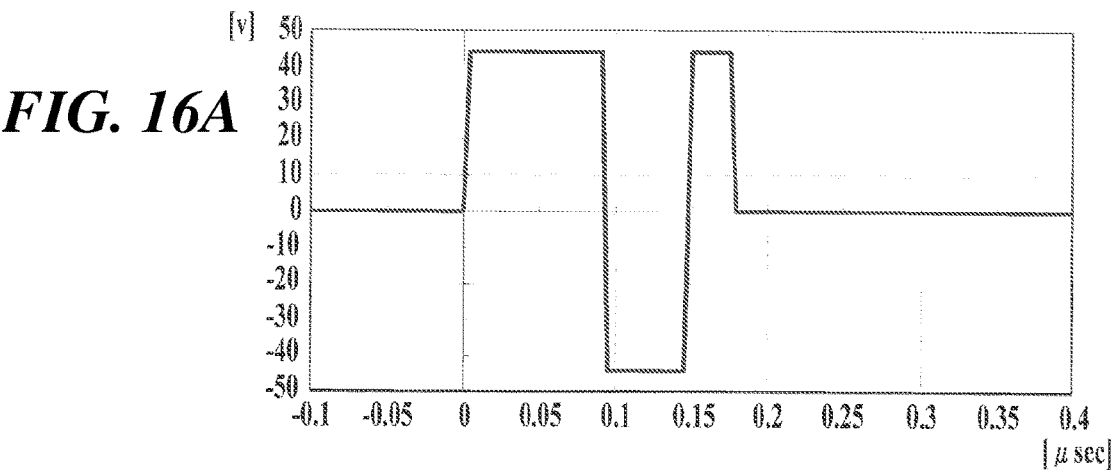
FIGS. 16A, 16B and 16C are diagrams each illustrating characteristics of a driving waveform D.
Figure 16B:
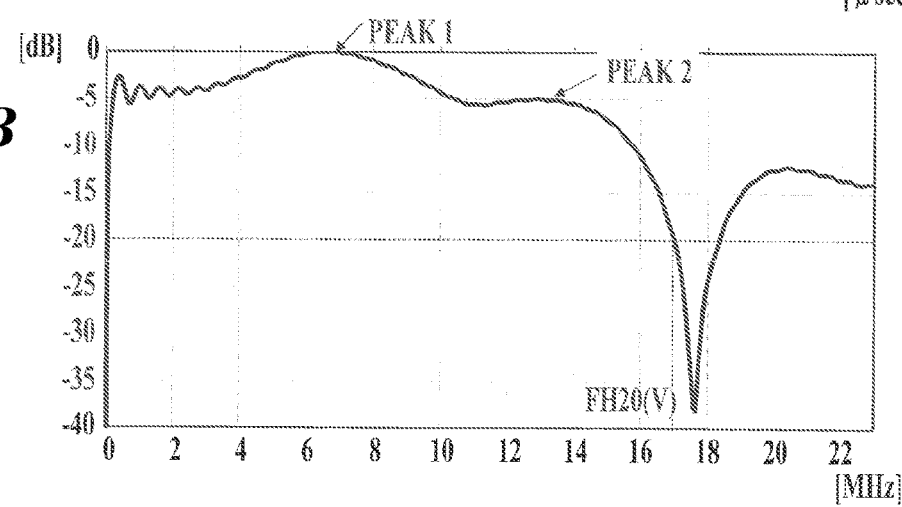
Figure 16C:
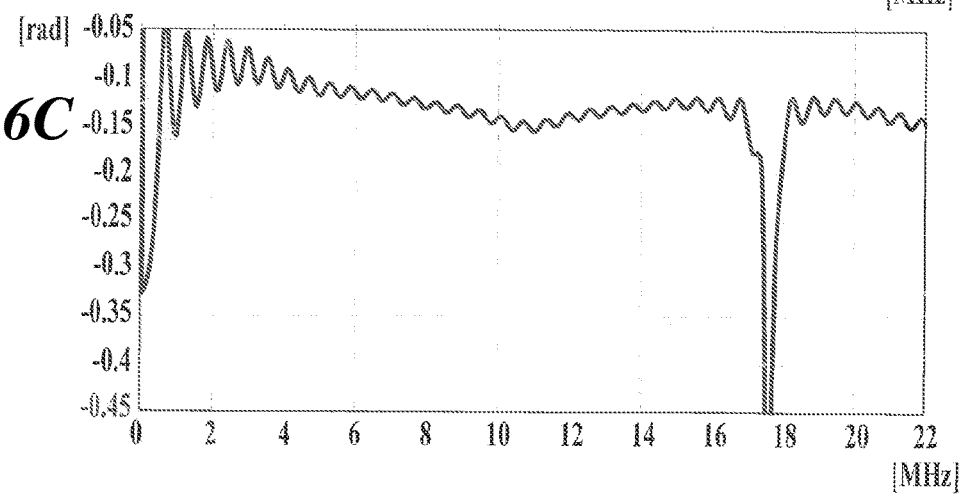

The first pulse signal output from the transmission section 12 was the driving signal of the driving waveform D illustrated in FIG. 16A. FIG. 16B illustrates the frequency power spectrum obtained by the frequency analysis of the driving waveform D. FIG. 16C illustrates the group delay characteristics of the driving waveform D. In FIG. 16A, the horizontal axis indicates the time, and the vertical axis indicates the voltage. In FIG. 16B, the horizontal axis indicates the frequency, and the vertical axis indicates the signal intensity. In FIG. 16C, the horizontal axis indicates the frequency, and the vertical axis indicates the group delay amount.

The driving waveform D had two intensity peaks in the transmission/reception frequency band (3.99 MHz to 19.72 MHz) at −20 dB of the ultrasound probe A. One intensity peak located on the low frequency side, and another intensity peak located on the high frequency side, with respect to the center frequency (FC20: 11.86 MHz) in the transmission/reception frequency band at −20 dB of the ultrasound probe A.

The pulse duration of the driving waveform D was 180 ns, which corresponded to 2.13 periods at the center frequency (FC20: 11.86 MHz) in the transmission/reception frequency band at −20 dB of the ultrasound probe A. In other words, the pulse duration of the driving waveform D was equal to or more than the time corresponding to two periods at the center frequency (FC20: 11.86 MHz) of the transmission/reception frequency band at −20 dB of the ultrasound probe A (see FIG. 24).

The frequency band where the frequency band included in the transmission/reception frequency band at −20 dB of the ultrasound probe A and the frequency band at −20 dB of the driving waveform D overlap each other was within the range from the lower limit frequency (FL20) of 3.99 MHz to the upper limit frequency (FH20) of 17.02 MHz. Concretely, the above upper limit frequency was smaller than the upper limit frequency of the transmission/reception frequency band at −20 dB of the ultrasound probe A, whereas the above lower limit frequency corresponds to the lower limit frequency of the transmission/reception frequency band at −20 dB of the ultrasound probe A. Thus, this frequency band is narrower than the transmission frequency band at −20 dB of the ultrasound probe A. A cover ratio of the ultrasound probe A of this frequency bandwidth over the transmission/reception frequency bandwidth at −20 dB was 83%.

The difference between the maximum value and the minimum value of the group delays of the driving waveform D in the frequency band where the frequency band included in the transmission/reception frequency band at −20 dB of the ultrasound probe A and the frequency band at −20 dB of the driving waveform D overlap each other was 0.065 radian. The standard deviation of the group delays of the driving waveform D in the frequency band where the frequency band included in the transmission/reception frequency band at −20 dB of the ultrasound probe A and the frequency band at −20 dB of the driving waveform D overlap each other was 0.0130.

The difference between the maximum value and the minimum value of the totaling values of the group delay of the ultrasound probe A obtained as described above and the group delay of the driving waveform D, in the frequency band where the frequency band included in the transmission/reception frequency band at −20 dB of the ultrasound probe A and the frequency band at −20 dB of the driving waveform D overlap each other, was 0.089.

The second pulse signal was the driving signal of the driving waveform obtained by inverting the polarity of the driving waveform D.

Example 7

The above-described ultrasound probe A was used as the ultrasound probe 2.

Figure 17A:
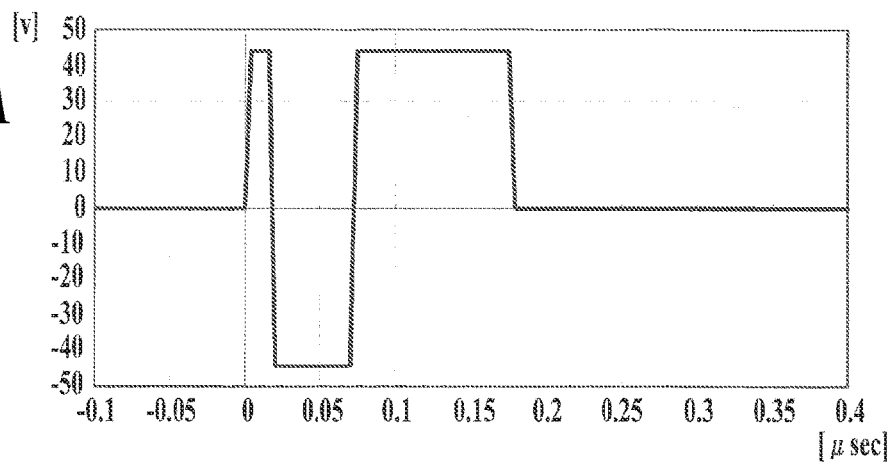
FIGS. 17A, 17B and 17C are diagrams each illustrating characteristics of a driving waveform E.
Figure 17B:
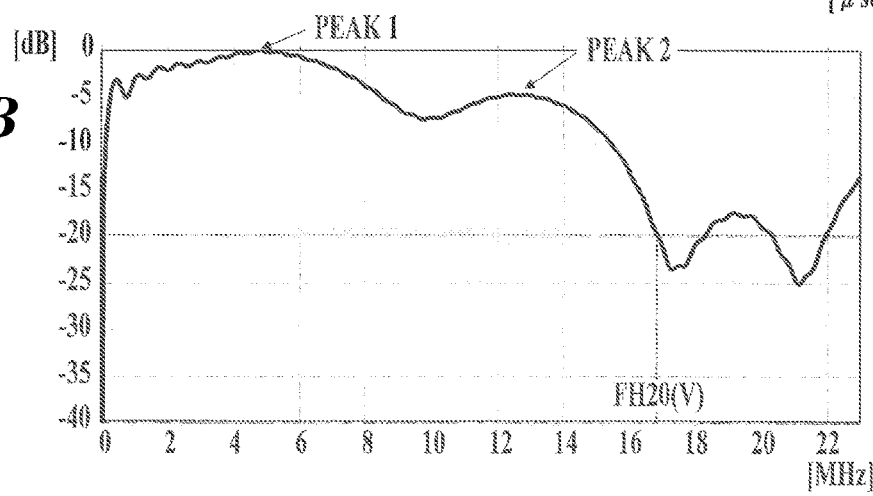
Figure 17C:
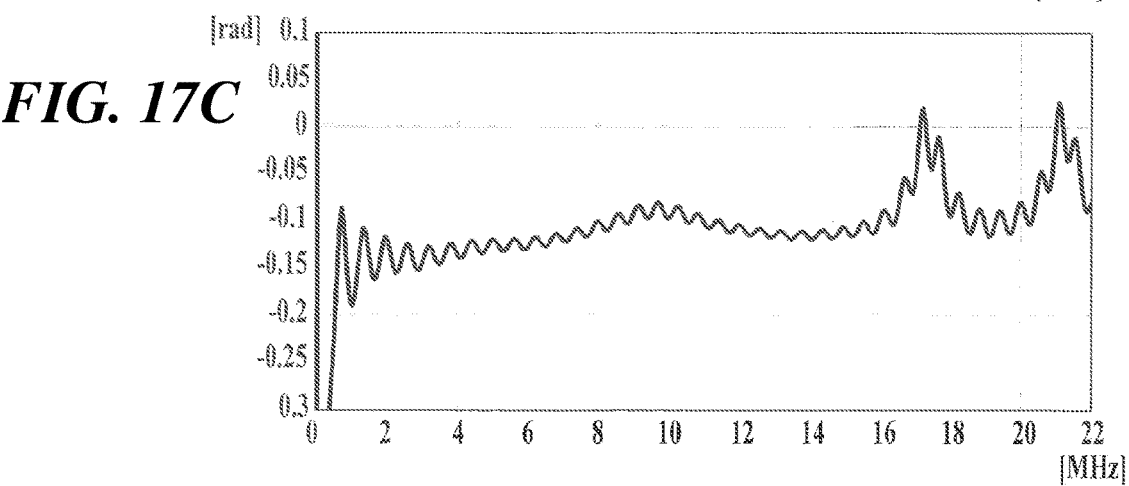

The first pulse signal output from the transmission section 12 was the driving signal of the driving waveform E illustrated in FIG. 17A. FIG. 17B illustrates the frequency power spectrum obtained by the frequency analysis of the driving waveform E. FIG. 17C illustrates the group delay characteristics of the driving waveform E. In FIG. 17A, the horizontal axis indicates the time, and the vertical axis indicates the voltage. In FIG. 17B, the horizontal axis indicates the frequency, and the vertical axis indicates the signal intensity. In FIG. 17C, the horizontal axis indicates the frequency, and the vertical axis indicates the group delay amount.

The driving waveform E had two intensity peaks in the transmission/reception frequency band (3.99 MHz to 19.72 MHz) at −20 dB of the ultrasound probe A. One intensity peak located on the low frequency side, and another intensity peak located on the high frequency side, with respect to the center frequency (FC20: 11.86 MHz) in the transmission/reception frequency band at −20 dB of the ultrasound probe A.

The pulse duration of the driving waveform E was 180 ns, which corresponded to 2.13 periods at the center frequency (FC20: 11.86 MHz) in the transmission/reception frequency band at −20 dB of the ultrasound probe A. In other words, the pulse duration of the driving waveform E was equal to or more than the time corresponding to two periods at the center frequency (FC20: 11.86 MHz) in the transmission/reception frequency band at −20 dB of the ultrasound probe A (see FIG. 24).

The frequency band where the frequency band included in the transmission/reception frequency band at −20 dB of the ultrasound probe A and the frequency band at −20 dB of the driving waveform E overlap each other was within the range from the lower limit frequency (FL20) of 3.99 MHz to the upper limit frequency (FH20) of 16.88 MHz. Concretely, the above upper limit frequency was smaller than the upper limit frequency of the transmission/reception frequency band at −20 dB of the ultrasound probe A, whereas the above lower limit frequency corresponds to the lower limit frequency of the transmission/reception frequency band at −20 dB of the ultrasound probe A. Thus, this frequency band is narrower than the transmission frequency band at −20 dB of the ultrasound probe A. A cover ratio of the ultrasound probe A of this frequency bandwidth over the transmission/reception frequency bandwidth at −20 dB was 82%.

The difference between the maximum value and the minimum value of the group delays of the driving waveform E in the frequency band where the frequency band included in the transmission/reception frequency band at −20 dB of the ultrasound probe A and the frequency band at −20 dB of the driving waveform E overlap each other was 0.086 radian. The standard deviation of the group delays of the driving waveform E in the frequency band where the frequency band included in the transmission/reception frequency band at −20 dB of the ultrasound probe A and the frequency band at −20 dB of the driving waveform E overlap each other was 0.0149.

The difference between the maximum value and the minimum value of the totaling values of the group delay of the ultrasound probe A obtained as described above and the group delay of the driving waveform E, in the frequency band where the frequency band included in the transmission/reception frequency band at −20 dB of the ultrasound probe A and the frequency band at −20 dB of the driving waveform E overlap each other, was 0.127.

The second pulse signal was the driving signal of the driving waveform obtained by inverting the polarity of the driving waveform E.

Example 8

The above-described ultrasound probe B was used as the ultrasound probe 2.

The first pulse signal output from the transmission section 12 was the driving signal of the driving waveform B described by referring to FIGS. 14A, 14B and 14C.

The driving waveform B had three intensity peaks in the transmission/reception frequency band (3.82 MHz to 19.86 MHz) at −20 dB of the ultrasound probe B, and one of the intensity peaks located on the low frequency side with respect to the center frequency (FC20: 11.84 MHz) in the transmission/reception frequency band at −20 dB of the ultrasound probe B, and other two intensity peaks located on the high frequency side with respect to the center frequency (FC20: 11.84 MHz) in the transmission/reception frequency band at −20 dB of the ultrasound probe B.

The pulse duration of the driving waveform B was 207 ns, which corresponded to 2.45 periods at the center frequency (FC20: 11.84 MHz) in the transmission/reception frequency band at −20 dB of the ultrasound probe B. In other words, the pulse duration of the driving waveform B was equal to or more than the time corresponding to two periods at the center frequency (FC20: 11.84 MHz) in the transmission/reception frequency band at −20 dB of the ultrasound probe B (see FIG. 24).

The frequency band where the frequency band included in the transmission/reception frequency band at −20 dB of the ultrasound probe B and the frequency band at −20 dB of the driving waveform B overlap each other corresponds to the transmission/reception frequency band at −20 dB of the ultrasound probe B, which was within the range from the lower limit frequency of 3.82 MHz (FL20) to the upper limit frequency of 19.86 MHz (FH20). A cover ratio of the ultrasound probe B of this frequency bandwidth over the transmission/reception frequency bandwidth at −20 dB was 100%.

The difference between the maximum value and the minimum value of the group delays of the driving waveform B in the frequency band where the frequency band included in the transmission/reception frequency band at −20 dB of the ultrasound probe B and the frequency band at −20 dB of the driving waveform B overlap each other was 0.092 radian. The standard deviation of the group delays of the driving waveform B in the frequency band where the frequency band included in the transmission/reception frequency band at −20 dB of the ultrasound probe B and the frequency band at −20 dB of the driving waveform B overlap each other was 0.0194.

Figure 22:
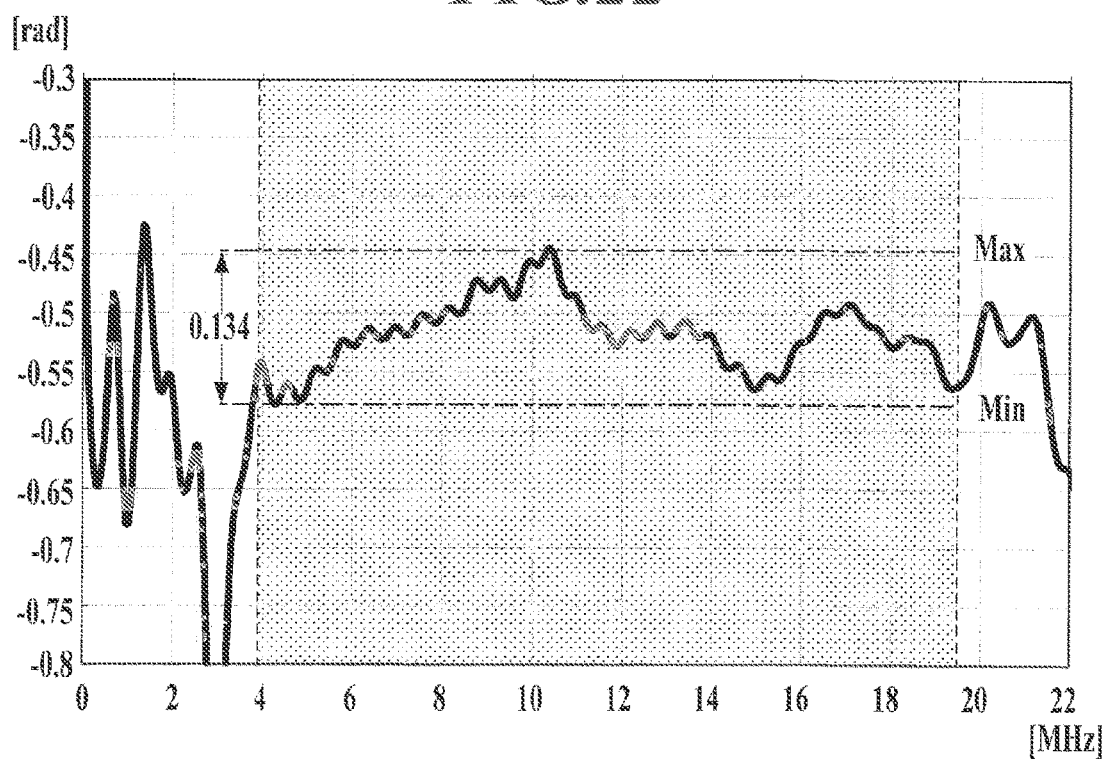
FIG. 22 is a diagram illustrating a totaling result of a group delay of the ultrasound probe B and a group delay of the driving waveform B.

The difference between the maximum value and the minimum value of the totaling values of the group delay of the ultrasound probe B obtained as described above and the group delay of the driving waveform B, in the frequency band where the frequency band included in the transmission/reception frequency band at −20 dB of the ultrasound probe B and the frequency band at −20 dB of the driving waveform B overlap each other, was 0.134. FIG. 22 illustrates the totaling result of the group delay of the ultrasound probe B and the group delay of the driving waveform B.

The second pulse signal was the driving signal of the driving waveform obtained by inverting the polarity of the driving waveform B.

Example 9

The above-described ultrasound probe B was used as the ultrasound probe 2.

The first pulse signal output from the transmission section 12 was the driving signal of the driving waveform D described by referring to FIGS. 16A, 16B and 16C.

The driving waveform D had two intensity peaks in the transmission/reception frequency band (3.82 MHz to 19.86 MHz) at −20 dB of the ultrasound probe B. One intensity peak located on the low frequency side, and another intensity peak located on the high frequency side, with respect to the center frequency (FC20: 11.84 MHz) in the transmission/reception frequency band at −20 dB of the ultrasound probe B.

The pulse duration of the driving waveform D was 180 ns, which corresponded to 2.13 periods at the center frequency (FC20: 11.84 MHz) in the transmission/reception frequency band at −20 dB of the ultrasound probe B. In other words, the pulse duration of the driving waveform D was equal to or more than the time corresponding to two periods at the center frequency (FC20: 11.84 MHz) in the transmission/reception frequency band at −20 dB of the ultrasound probe B (see FIG. 24).

The frequency band where the frequency band included in the transmission/reception frequency band at −20 dB of the ultrasound probe B and the frequency band at −20 dB of the driving waveform D overlap each other was within the range from the lower limit frequency (FL20) of 3.82 MHz to the upper limit frequency (FH20) of 17.02 MHz. Concretely, the above upper limit frequency was smaller than the upper limit frequency of the transmission/reception frequency band at −20 dB of the ultrasound probe B, whereas the above lower limit frequency corresponds to the lower limit frequency of the transmission/reception frequency band at −20 dB of the ultrasound probe B. Thus, this frequency band is narrower than the transmission frequency band at −20 dB of the ultrasound probe B. A cover ratio of the ultrasound probe B of this frequency bandwidth over the transmission/reception frequency bandwidth at −20 dB was 82%.

The difference between the maximum value and the minimum value of the group delays of the driving waveform D in the frequency band where the frequency band included in the transmission/reception frequency band at −20 dB of the ultrasound probe B and the frequency band at −20 dB of the driving waveform D overlap each other was 0.065 radian. The standard deviation of the group delays of the driving waveform D in the frequency band where the frequency band included in the transmission/reception frequency band at −20 dB of the ultrasound probe B and the frequency band at −20 dB of the driving waveform D overlap each other was 0.0131.

The difference between the maximum value and the minimum value of the totaling value of the group delay of the ultrasound probe B obtained as described above and the group delay of the driving waveform D, in the frequency band where the frequency band included in the transmission/reception frequency band at −20 dB of the ultrasound probe B and the frequency band at −20 dB of the driving waveform D overlap each other, was 0.076.

The second pulse signal was the driving signal of the driving waveform obtained by inverting the polarity of the driving waveform D.

Comparative Example 1

The above-described ultrasound probe C was used as the ultrasound probe 2.

The first pulse signal output from the transmission section 12 was the driving signal of the driving waveform A same as that of Example 1.

The driving waveform A had three intensity peaks in the transmission/reception frequency band (3.75 MHz to 20.23 MHz) at −20 dB of the ultrasound probe C, and one of the intensity peaks located on the low frequency side with respect to the center frequency (FC20: 11.99 MHz) in the transmission/reception frequency band at −20 dB of the ultrasound probe C, and other two intensity peaks located on the high frequency side with respect to the center frequency (FC20: 11.99 MHz) in the transmission/reception frequency band at −20 dB of the ultrasound probe C.

The pulse duration of the driving waveform A was 233 ns, which corresponded to 2.79 periods at the center frequency (FC20: 11.99 MHz) in the transmission/reception frequency band at −20 dB of the ultrasound probe C.

The frequency band where the frequency band included in the transmission/reception frequency band at −20 dB of the ultrasound probe C and the frequency band at −20 dB of the driving waveform A overlap each other corresponds to the transmission/reception frequency band at −20 dB of the ultrasound probe C, which was within the range from the lower limit frequency of 3.75 MHz (FL20) to the upper limit frequency of 20.23 MHz (FH20). A cover ratio of the ultrasound probe C of this frequency bandwidth over the transmission/reception frequency bandwidth at −20 dB was 100%.

The difference between the maximum value and the minimum value of the group delays of the driving waveform A in the frequency band where the frequency band included in the transmission/reception frequency band at −20 dB of the ultrasound probe C and the frequency band at −20 dB of the driving waveform A overlap each other was 0.107 radian. The standard deviation of the group delays of the driving waveform A in the frequency band where the frequency band included in the transmission/reception frequency band at −20 dB of the ultrasound probe C and the frequency band at −20 dB of the driving waveform A overlap each other was 0.0206.

The difference between the maximum value and the minimum value of the totaling values of the group delay of the ultrasound probe C obtained as described above and the group delay of the driving waveform A, in the frequency band where the frequency band included in the transmission/reception frequency band at −20 dB of the ultrasound probe C and the frequency band at −20 dB of the driving waveform A overlap each other, was 0.152.

The second pulse signal was the driving signal of the driving waveform obtained by inverting the polarity of the driving waveform A.

Comparative Example 2

The above-described ultrasound probe D was used as the ultrasound probe 2.

The first pulse signal output from the transmission section 12 was the driving signal of the driving waveform A same as that of Example 1.

The driving waveform A had three intensity peaks in the transmission/reception frequency band (3.96 MHz to 19.78 MHz) at −20 dB of the ultrasound probe D, and one of the intensity peaks located on the low frequency side with respect to the center frequency (FC20: 11.87 MHz) in the transmission/reception frequency band at −20 dB of the ultrasound probe D, and other two intensity peaks located on the high frequency side with respect to the center frequency (FC20: 11.87 MHz) in the transmission/reception frequency band at −20 dB of the ultrasound probe D.

The pulse duration of the driving waveform A was 233 ns, which corresponded to 2.77 periods at the center frequency (FC20: 11.87 MHz) in the transmission/reception frequency band at −20 dB of the ultrasound probe D.

The frequency band where the frequency band included in the transmission/reception frequency band at −20 dB of the ultrasound probe D and the frequency band at −20 dB of the driving waveform A overlap each other corresponds to the transmission/reception frequency band at −20 dB of the ultrasound probe D, which was within the range from the lower limit frequency of 3.96 MHz (FL20) to the upper limit frequency of 19.78 MHz (FH20). A cover ratio of the ultrasound probe D of this frequency bandwidth over the transmission/reception frequency bandwidth at −20 dB was 100%.

The difference between the maximum value and the minimum value of the group delays of the driving waveform A in the frequency band where the frequency band included in the transmission/reception frequency band at −20 dB of the ultrasound probe D and the frequency band at −20 dB of the driving waveform A overlap each other was 0.107 radian. The standard deviation of the group delays of the driving waveform A in the frequency band where the frequency band included in the transmission/reception frequency band at −20 dB of the ultrasound probe D and the frequency band at −20 dB of the driving waveform A overlap each other was 0.0208.

The difference between the maximum value and the minimum value of the totaling values of the group delay of the ultrasound probe D obtained as described above and the group delay of the driving waveform A, in the frequency band where the frequency band included in the transmission/reception frequency band at −20 dB of the ultrasound probe D and the frequency band at −20 dB of the driving waveform A overlap each other, was 0.163.

The second pulse signal was the driving signal of the driving waveform obtained by inverting the polarity of the driving waveform A.

Comparative Example 3

The above-described ultrasound probe A was used as the ultrasound probe 2.

Figure 18A:
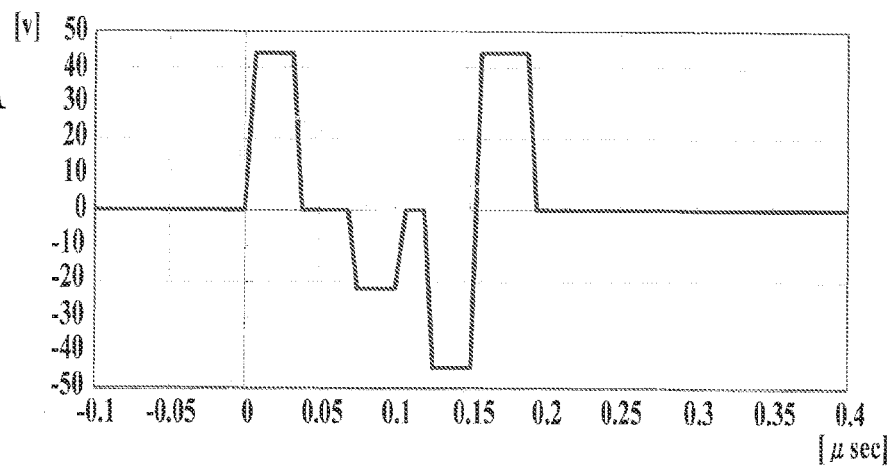
FIGS. 18A, 18B and 18C are diagrams each illustrating characteristics of a driving waveform F.
Figure 18B:
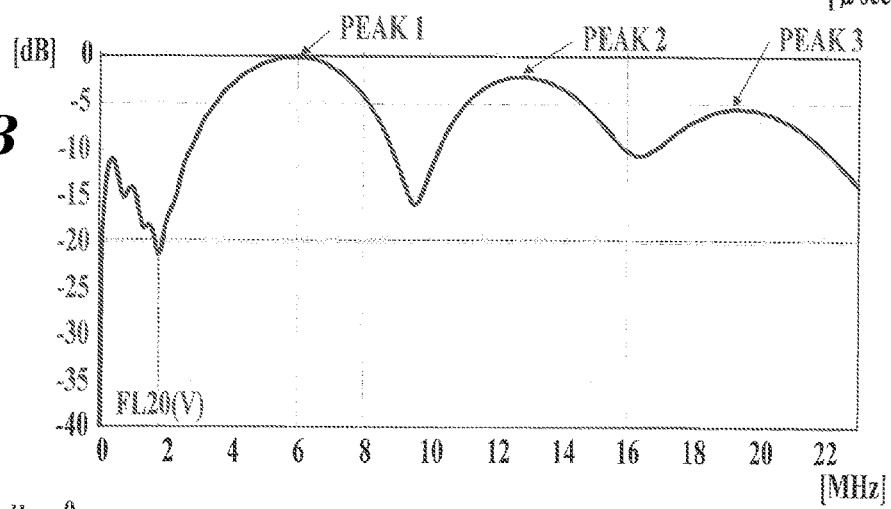
Figure 18C:
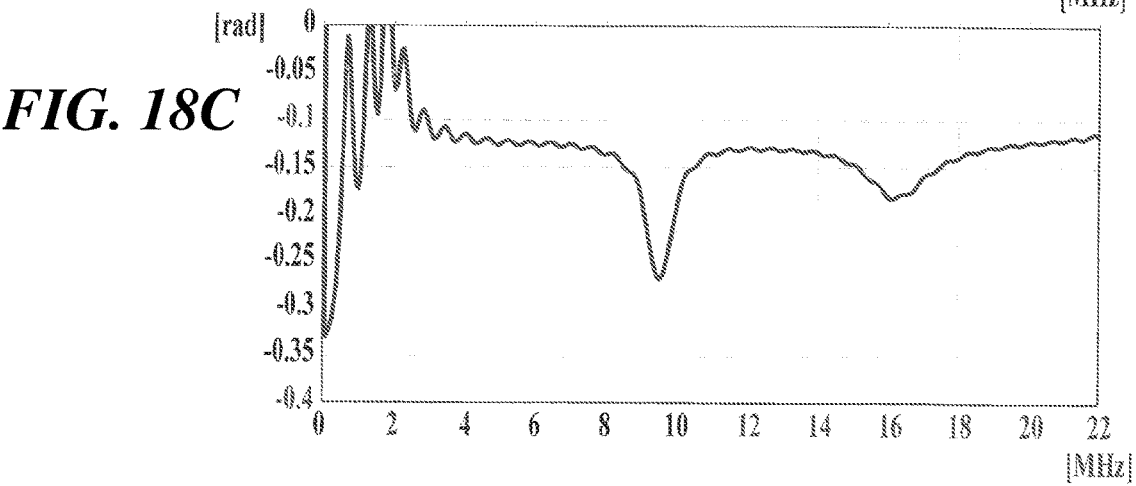

The first pulse signal output from the transmission section 12 was the driving signal of the driving waveform F illustrated in FIG. 18A. FIG. 18B illustrates the frequency power spectrum obtained by the frequency analysis of the driving waveform F. FIG. 18C illustrates the group delay characteristics of the driving waveform F. In FIG. 18A, the horizontal axis indicates the time, and the vertical axis indicates the voltage. In FIG. 18B, the horizontal axis indicates the frequency, and the vertical axis indicates the signal intensity. In FIG. 18C, the horizontal axis indicates the frequency, and the vertical axis indicates the group delay amount.

The driving waveform F had three intensity peaks in the transmission/reception frequency band (3.99 MHz to 19.72 MHz) at −20 dB of the ultrasound probe A, and one of the intensity peaks located on the low frequency side with respect to the center frequency (FC20: 11.86 MHz) in the transmission/reception frequency band at −20 dB of the ultrasound probe A, and other two intensity peaks located on the high frequency side with respect to the center frequency (FC20: 11.86 MHz) in the transmission/reception frequency band at −20 dB of the ultrasound probe A.

The pulse duration of the driving waveform F was 194 ns, which corresponded to 2.30 periods at the center frequency (FC20: 11.86 MHz) in the transmission/reception frequency band at −20 dB of the ultrasound probe A.

The frequency band where the frequency band included in the transmission/reception frequency band at −20 dB of the ultrasound probe A and the frequency band at −20 dB of the driving waveform F overlap each other corresponds to the transmission/reception frequency band at −20 dB of the ultrasound probe A, which was within the range from the lower limit frequency of 3.99 MHz (FL20) to the upper limit frequency of 19.72 MHz (FH20). A cover ratio of the ultrasound probe A of this frequency bandwidth over the transmission/reception frequency bandwidth at −20 dB was 100%.

The difference between the maximum value and the minimum value of the group delays of the driving waveform F in the frequency band where the frequency band included in the transmission/reception frequency band at −20 dB of the ultrasound probe A and the frequency band at −20 dB of the driving waveform F overlap each other was 0.153 radian. The standard deviation of the group delays of the driving waveform F in the frequency band where the frequency band included in the transmission/reception frequency band at −20 dB of the ultrasound probe A and the frequency band at −20 dB of the driving waveform F overlap each other was 0.0287.

The difference between the maximum value and the minimum value of the totaling values of the group delay of the ultrasound probe A obtained as described above and the group delay of the driving waveform F, in the frequency band where the frequency band included in the transmission/reception frequency band at −20 dB of the ultrasound probe A and the frequency band at −20 dB of the driving waveform F overlap each other, was 0.162.

The second pulse signal was the driving signal of the driving waveform obtained by inverting the polarity of the driving waveform F.

Comparative Example 4

The above-described ultrasound probe A was used as the ultrasound probe 2.

Figure 19A:
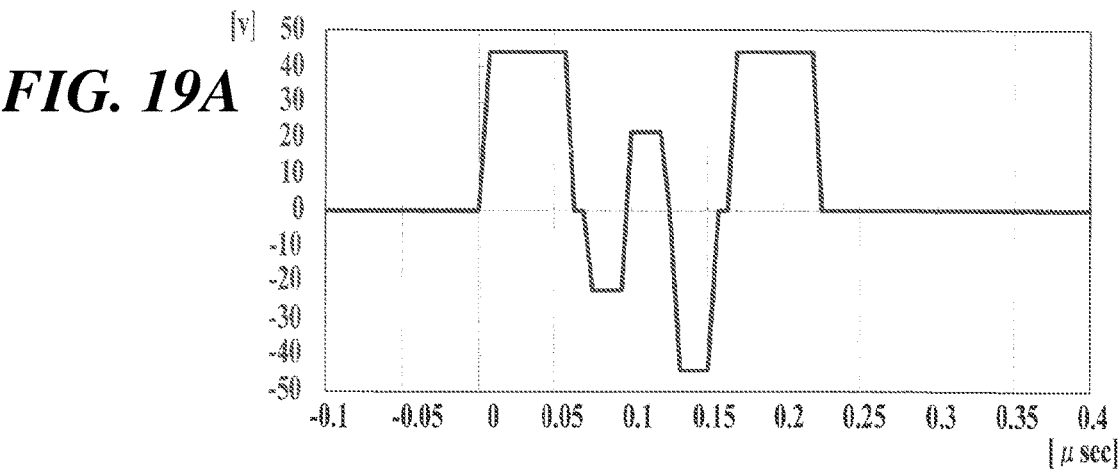
FIGS. 19A, 19B and 19C are diagrams each illustrating characteristics of a driving waveform G.
Figure 19B:
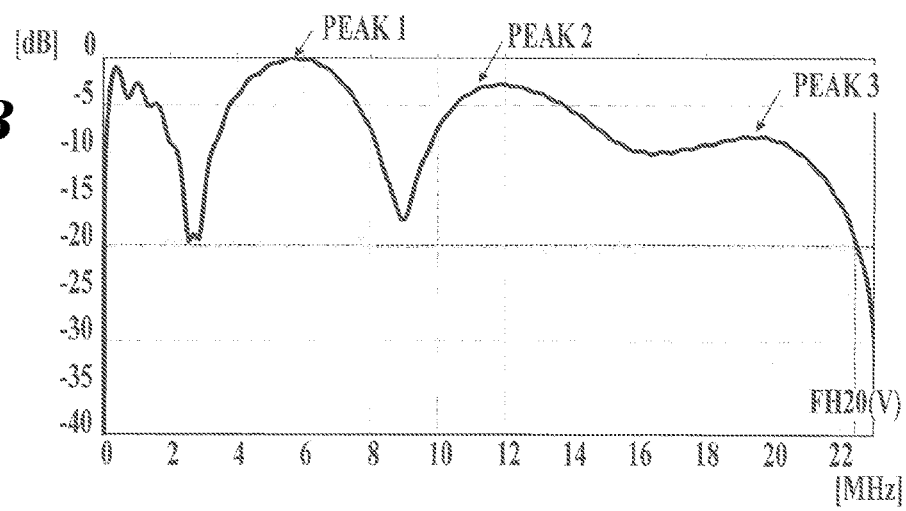
Figure 19C:
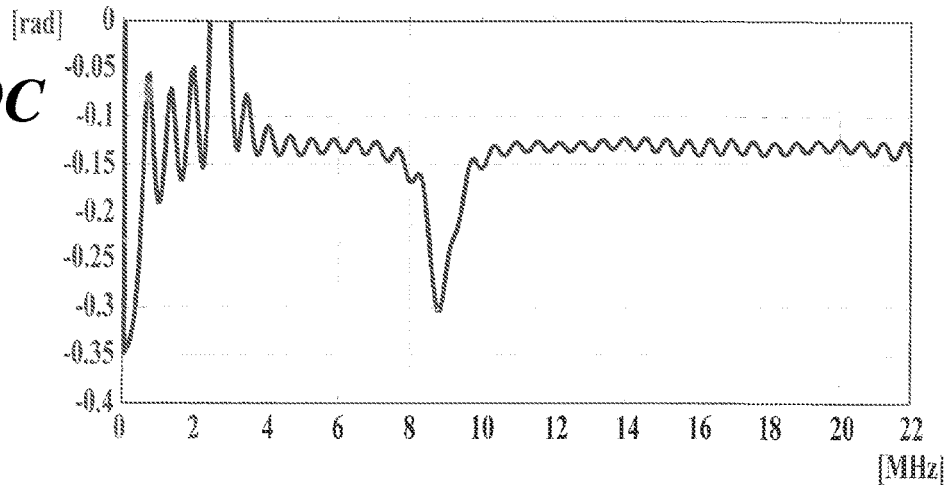

The first pulse signal output from the transmission section 12 was the driving signal of the driving waveform G illustrated in FIG. 19A. FIG. 19B illustrates the frequency power spectrum obtained by the frequency analysis of the driving waveform G. FIG. 19C illustrates the group delay characteristics of the driving waveform G. In FIG. 19A, the horizontal axis indicates the time, and the vertical axis indicates the voltage. In FIG. 19B, the horizontal axis indicates the frequency, and the vertical axis indicates the signal intensity. In FIG. 19C, the horizontal axis indicates the frequency, and the vertical axis indicates the group delay amount.

The driving waveform G had three intensity peaks in the transmission/reception frequency band (3.99 MHz to 19.72 MHz) at −20 dB of the ultrasound probe A, and two of the intensity peaks located on the low frequency side with respect to the center frequency (FC20: 11.86 MHz) in the transmission/reception frequency band at −20 dB of the ultrasound probe A, and remaining one intensity peak located on the high frequency side with respect to the center frequency (FC20: 11.86 MHz) in the transmission/reception frequency band at −20 dB of the ultrasound probe A.

The pulse duration of the driving waveform G was 225 ns, which corresponded to 2.67 periods at the center frequency (FC20: 11.86 MHz) in the transmission/reception frequency band at −20 dB of the ultrasound probe A.

The frequency band where the frequency band included in the transmission/reception frequency band at −20 dB of the ultrasound probe A and the frequency band at −20 dB of the driving waveform G overlap each other corresponds to the transmission/reception frequency band at −20 dB of the ultrasound probe A, which was within the range from the lower limit frequency of 3.99 MHz (FL20) to the upper limit frequency of 19.72 MHz (FH20). A cover ratio of the ultrasound probe A of this frequency bandwidth over the transmission/reception frequency bandwidth at −20 dB was 100%.

The difference between the maximum value and the minimum value of the group delays of the driving waveform G in the frequency band where the frequency band included in the transmission/reception frequency band at −20 dB of the ultrasound probe A and the frequency band at −20 dB of the driving waveform G overlap each other was 0.195 radian. The standard deviation of the group delays of the driving waveform G in the frequency band where the frequency band included in the transmission/reception frequency band at −20 dB of the ultrasound probe A and the frequency band at −20 dB of the driving waveform G overlap each other was 0.0314.

Figure 23:
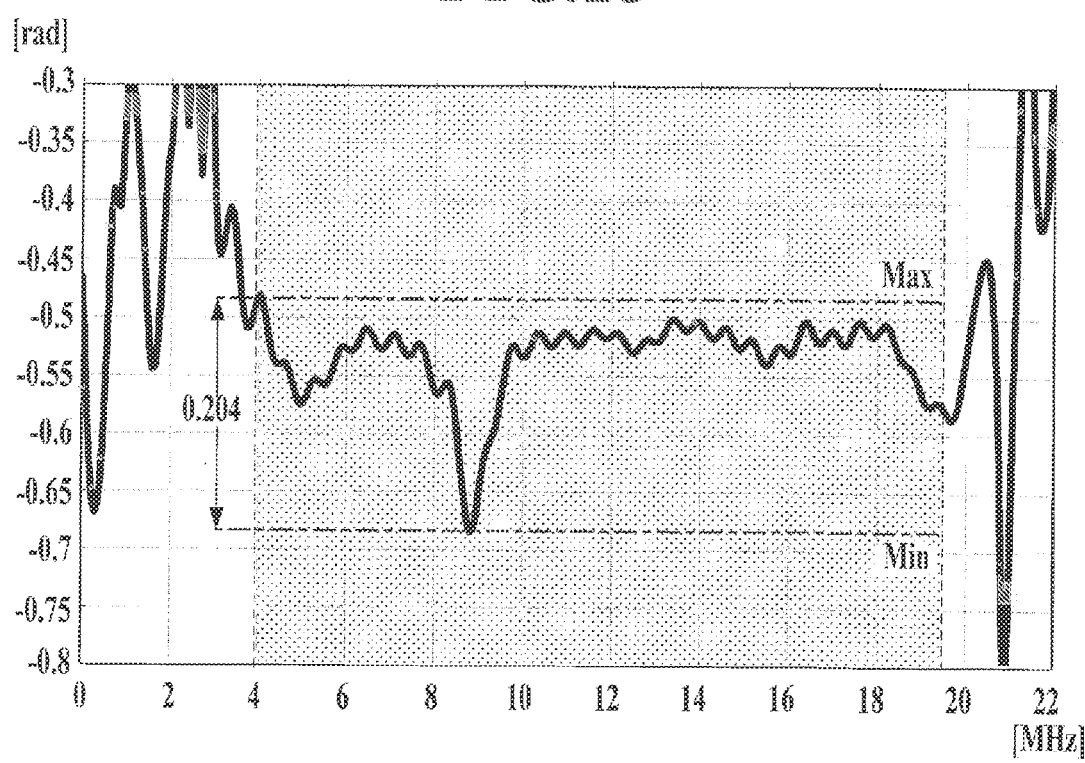
FIG. 23 is a diagram illustrating a totaling result of a group delay of the ultrasound probe A and a group delay of the driving waveform G.

The difference between the maximum value and the minimum value of the totaling values of the group delay of the ultrasound probe A obtained as described above and the group delay of the driving waveform G, in the frequency band where the frequency band included in the transmission/reception frequency band at −20 dB of the ultrasound probe A and the frequency band at −20 dB of the driving waveform G overlap each other, was 0.204. FIG. 23 illustrates the totaling result of the group delay of the ultrasound probe A and the group delay of the driving waveform G.

The second pulse signal was the driving signal of the driving waveform obtained by the inverting the polarity of the driving waveform G.

Comparative Example 5

The above-described ultrasound probe A was used as the ultrasound probe 2.

Figure 20A:
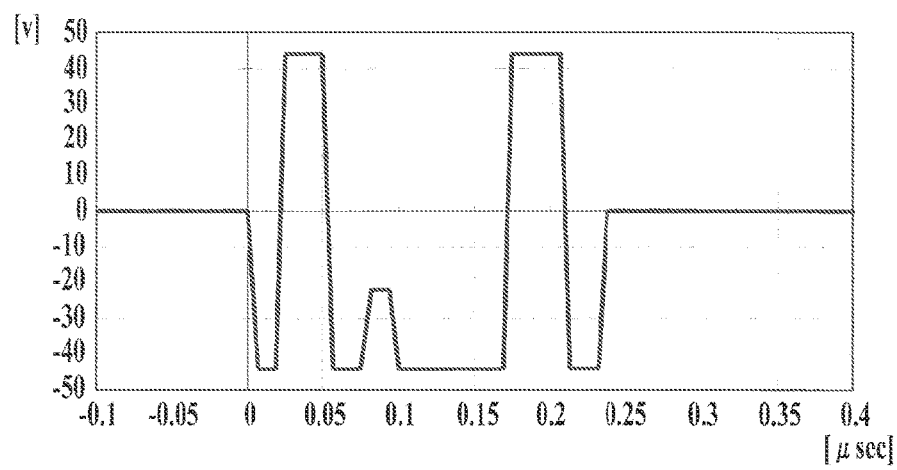
FIGS. 20A, 20B and 20C are diagrams each illustrating characteristics of a driving waveform H.
Figure 20B:
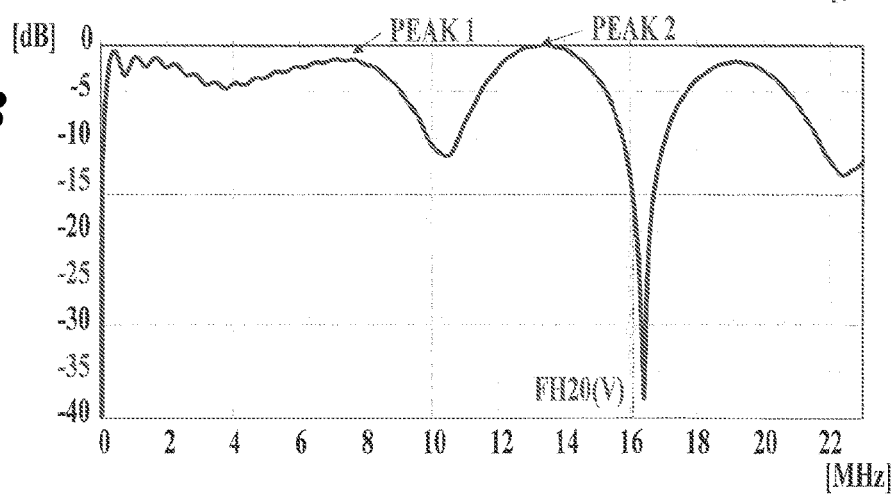
Figure 20C:
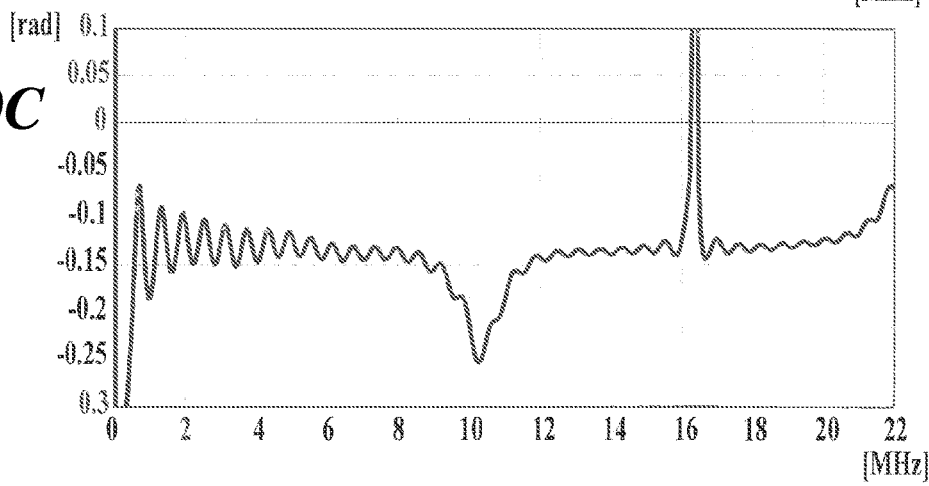

The first pulse signal output from the transmission section 12 was the driving signal of the driving waveform H illustrated in FIG. 20A. FIG. 20B illustrates the frequency power spectrum obtained by the frequency analysis of the driving waveform H. FIG. 20C illustrates the group delay characteristics of the driving waveform H. In FIG. 20A, the horizontal axis indicates the time, and the vertical axis indicates the voltage. In FIG. 20B, the horizontal axis indicates the frequency, and the vertical axis indicates the signal intensity. In FIG. 20C, the horizontal axis indicates the frequency, and the vertical axis indicates the group delay amount.

The driving waveform H had two intensity peaks in the transmission/reception frequency band (3.99 MHz to 19.72 MHz) at −20 dB of the ultrasound probe A. One intensity peak located on the low frequency side, and another intensity peak located on the high frequency side, with respect to the center frequency (FC20: 11.86 MHz) in the transmission/reception frequency band at −20 dB of the ultrasound probe A.

The pulse duration of the driving waveform H was 238 ns, which corresponded to 2.82 periods at the center frequency (FC20: 11.86 MHz) in the transmission/reception frequency band at −20 dB of the ultrasound probe A.

The frequency band where the frequency band included in the transmission/reception frequency band at −20 dB of the ultrasound probe A and the frequency band at −20 dB of the driving waveform H overlap each other was within the range from the lower limit frequency (FL20) of 3.99 MHz to the upper limit frequency (FH20) of 16.18 MHz. Concretely, the above upper limit frequency was smaller than the upper limit frequency of the transmission/reception frequency band at −20 dB of the ultrasound probe A, whereas the above lower limit frequency corresponds to the lower limit frequency of the transmission/reception frequency band at −20 dB of the ultrasound probe A. Thus, this frequency band is narrower than the transmission frequency band at −20 dB of the ultrasound probe A. A cover ratio of the ultrasound probe A of this frequency bandwidth over the transmission/reception frequency bandwidth at −20 dB was 77%.

The difference between the maximum value and the minimum value of the group delays of the driving waveform H in the frequency band where the frequency band included in the transmission/reception frequency band at −20 dB of the ultrasound probe A and the frequency band at −20 dB of the driving waveform H overlap each other was 0.172 radian. The standard deviation of the group delays of the driving waveform H in the frequency band where the frequency band included in the transmission/reception frequency band at −20 dB of the ultrasound probe A and the frequency band at −20 dB of the driving waveform H overlap each other was 0.0278.

The difference between the maximum value and the minimum value of the totaling values of the group delay of the ultrasound probe A obtained as described above and the group delay of the driving waveform H, in the frequency band where the frequency band included in the transmission/reception frequency band at −20 dB of the ultrasound probe A and the frequency band at −20 dB of the driving waveform H overlap each other, was 0.170.

The second pulse signal was the driving signal of the driving waveform obtained by inverting the polarity of the driving waveform H.

Comparative Example 6

The above-described ultrasound probe B was used as the ultrasound probe 2.

The first pulse signal output from the transmission section 12 was the driving signal of the driving waveform H same as that of Comparative example 5.

The driving waveform H had two intensity peaks in the transmission/reception frequency band (3.82 MHz to 19.86 MHz) at −20 dB of the ultrasound probe B. One intensity peak located on the low frequency side, and another intensity peak located on the high frequency side, with respect to the center frequency (FC20: 11.84 MHz) in the transmission/reception frequency band at −20 dB of the ultrasound probe B.

The pulse duration of the driving waveform H was 238 ns, which corresponded to 2.82 periods at the center frequency (FC20: 11.84 MHz) in the transmission/reception frequency band at −20 dB of the ultrasound probe B.

The frequency band where the frequency band included in the transmission/reception frequency band at −20 dB of the ultrasound probe B and the frequency band at −20 dB of the driving waveform H overlap each other was within the range from the lower limit frequency (FL20) of 3.82 MHz to the upper limit frequency (FH20) of 16.18 MHz. Concretely, the above upper limit frequency was smaller than the upper limit frequency of the transmission/reception frequency band at −20 dB of the ultrasound probe B, whereas the above lower limit frequency corresponds to the lower limit frequency of the transmission/reception frequency band at −20 dB of the ultrasound probe B. Thus, this frequency band is narrower than the transmission frequency band at −20 dB of the ultrasound probe B. A cover ratio of the ultrasound probe B of this frequency bandwidth over the transmission/reception frequency bandwidth at −20 dB was 77%.

The difference between the maximum value and the minimum value of the group delays of the driving waveform H in the frequency band where the frequency band included in the transmission/reception frequency band at −20 dB of the ultrasound probe B and the frequency band at −20 dB of the driving waveform H overlap each other was 0.172 radian. The standard deviation of the group delays of the driving waveform H in the frequency band where the frequency band included in the transmission/reception frequency band at −20 dB of the ultrasound probe B and the frequency band at −20 dB of the driving waveform H overlap each other was 0.0277.

The difference between the maximum value and the minimum value of the totaling values of the group delay of the ultrasound probe B obtained as described above and the group delay of the driving waveform H, in the frequency band where the frequency band included in the transmission/reception frequency band at −20 dB of the ultrasound probe B and the frequency band at −20 dB of the driving waveform H overlap each other, was 0.162.

The second pulse signal was the driving signal of the driving waveform obtained by inverting the polarity of the driving waveform H.

The conditions of the above examples and comparative examples are illustrated in Table 1.

TABLE 1

| | ULTRASOUND PROBE | | | | | | DRIVING WAVEFORM |
|---|---|---|---|---|---|---|---|
| | | | | | GROUP DELAY (RADIAN; WITHIN BW20) | | |
| | No. | FL20 [MHz] | FH20 [MHz] | FC20 [MHz] | BW20 [%] | STANDARD DEVIATION | Max − Min | No. |
| EXAMPLE 1 | A | 3.99 | 19.72 | 11.86 | 133 | 0.0184 | 0.082 | *1 A<br>*2 A(APOLARITY INVERSION) |
| EXAMPLE 2 | B | 3.82 | 19.86 | 11.84 | 135 | 0.0198 | 0.082 | *1 A<br>*2 A(APOLARITY INVERSION) |
| COMPARATIVE EXAMPLE 1 | C | 3.75 | 20.23 | 11.99 | 137 | 0.0287 | 0.154 | *1 A<br>*2 A(APOLARITY INVERSION) |
| COMPARATIVE EXAMPLE 2 | D | 3.96 | 19.78 | 11.87 | 133 | 0.0301 | 0.200 | *1 A<br>*2 A(APOLARITY INVERSION) |
| EXAMPLE 3 | A | 3.99 | 19.72 | 11.88 | 133 | 0.0184 | 0.082 | *1 A<br>*2 C |
| EXAMPLE 4 | | | | | | | | *1 B<br>*2 B(APOLARITY INVERSION) |
| EXAMPLE 5 | | | | | | | | *1 C<br>*2 C(APOLARITY INVERSION) |
| EXAMPLE 6 | | | | | | | | *1 D<br>*2 D(APOLARITY INVERSION) |
| EXAMPLE 7 | | | | | | | | *1 E<br>*2 E(APOLARITY INVERSION) |
| COMPARATIVE EXAMPLE 3 | | | | | | | | *1 F<br>*2 F(APOLARITY INVERSION) |
| COMPARATIVE EXAMPLE 4 | | | | | | | | *1 G<br>*2 G(APOLARITY INVERSION) |
| COMPARATIVE EXAMPLE 5 | | | | | | | | *1 H<br>*2 H(APOLARITY INVERSION) |
| EXAMPLE 8 | B | 3.82 | 19.86 | 11.84 | 135 | 0.0198 | 0.082 | *1 B<br>*2 B(APOLARITY INVERSION) |
| EXAMPLE 9 | | | | | | | | *1 D<br>*2 D(APOLARITY INVERSION) |
| COMPARATIVE EXAMPLE 6 | | | | | | | | *1 H<br>*2 H(APOLARITY INVERSION) |

| | DRIVING WAVEFORM | | | | | GROUP DELAY (RADIAN; WITHIN BW20) | | PROBE + DRIVING WAVEFORM TOTALING OF GROUP DELAYS (RADIAN; WITHIN BW20) |
|---|---|---|---|---|---|---|---|---|
| | *3 | *4 | *5 FL20 [MHz] | *5 FH20 [MHz] | *6 | STANDARD DEVIATION | Max − Min | Max − Min |
| EXAMPLE 1 | 233 | 2.76 | 3.99 | 19.72 | 100 | 0.0208 | 0.0107 | 0.115 |
| EXAMPLE 2 | 233 | 2.76 | 3.82 | 19.86 | 100 | 0.0206 | 0.0107 | 0.089 |
| COMPARATIVE EXAMPLE 1 | 233 | 2.79 | 3.75 | 20.23 | 100 | 0.0206 | 0.0107 | 0.152 |
| COMPARATIVE EXAMPLE 2 | 233 | 2.77 | 3.96 | 19.78 | 100 | 0.0208 | 0.0107 | 0.163 |
| EXAMPLE 3 | 233 | 2.76 | 3.99 | 19.72 | 100 | 0.0208 | 0.0107 | 0.115 |
| | 233 | 2.76 | 3.99 | 16.13 | 77 | 0.0117 | 0.079 | 0.087 |
| EXAMPLE 4 | 207 | 2.45 | 3.99 | 19.72 | 100 | 0.0195 | 0.092 | 0.120 |
| EXAMPLE 5 | 233 | 2.76 | 3.99 | 16.13 | 77 | 0.0117 | 0.079 | 0.087 |

TABLE 1-continued

| | *1 | *2 | *3 | *4 | *5 | *6 | | |
|---|---|---|---|---|---|---|---|---|
| EXAMPLE 6 | 180 | 2.13 | 3.99 | 17.02 | 83 | 0.0130 | 0.065 | 0.089 |
| EXAMPLE 7 | 180 | 2.13 | 3.99 | 16.88 | 82 | 0.0149 | 0.086 | 0.127 |
| COMPARATIVE EXAMPLE 3 | 194 | 2.30 | 3.99 | 19.72 | 100 | 0.0287 | 0.153 | 0.162 |
| COMPARATIVE EXAMPLE 4 | 225 | 2.87 | 3.99 | 19.72 | 100 | 0.0314 | 0.195 | 0.204 |
| COMPARATIVE EXAMPLE 5 | 238 | 2.82 | 3.99 | 16.18 | 77 | 0.0278 | 0.172 | 0.170 |
| EXAMPLE 8 | 207 | 2.45 | 3.82 | 19.86 | 100 | 0.0194 | 0.092 | 0.134 |
| EXAMPLE 9 | 180 | 2.13 | 3.82 | 17.02 | 82 | 0.0131 | 0.065 | 0.076 |
| COMPARATIVE EXAMPLE 6 | 238 | 2.82 | 3.82 | 16.18 | 77 | 0.0277 | 0.172 | 0.162 |

*1: FIRST WAVE TRANSMISSION
*2: SECOND WAVE TRANSMISSION
*3: PULSE DURATION [nsec]
*4 PROBE −20 dB CENTER FREQUENCY CONVERSION WAVENUMBER
*5: BAND OF DRIVING WAVEFORM WITHIN PROBE −20 dB BAND
*6: COVER RATIO OF DRIVING WAVEFORM BW20 OVER PROBE −BW20[%]

<Evaluation Method>

An SUS wire of 50 μm was embedded in an acoustic equivalent material part same as GAMMEX RMI 404GS-LE0.5 at the position of the depth of 15 mm. Then the first and second pulse signals of the driving waveforms of the conditions illustrated in Table 1 were applied to the same scanning line of the ultrasound probe with a predetermined time interval so that the ultrasound probe transmits/receives the first and second ultrasounds, and the reception signals obtained from the received first and second ultrasounds, respectively, were combined by the pulse inversion method to obtain the ultrasound image according to the Tissue Harmonic Imaging (THI). At that time, the transmission focal point was 15 mm. Then the wire visualization brightness at the time of imaging was converted into a sound intensity (dB) to obtain 20 dB resolution (distance resolution, azimuth resolution). Furthermore, the first and second ultrasounds were transmitted/received to the acoustic equivalent material part of GAMMEX RMI 403GS-LE0.5 while the transmission focal point was set to 15 mm. The ultrasound images of two consecutive frames was thus obtained, and a correlation between the ultrasound images of two frames was obtained. The depth at the time when the correlation is below 0.5 was obtained to be set as a Penetration. Moreover, a carpus, MetacarpoPhalangea (MP) joint flexor tendon, biceps brachii tendon, medial meniscus were visualized under the respective conditions of Examples 1 to 9 and Comparative examples 1 to 6, and ten persons including doctors engaged in orthopedics related business and medical technologists obtain scores according to the following evaluation criteria, and obtain an average of these values to set the average to a visualization score.

[Evaluation Criteria]
10: Visualization degree satisfactory in grasping a condition of tissue
8: Visualization degree with no trouble practically in grasping the condition of tissue
6: Visualization degree not good but capable of grasping the condition of tissue
4: Visualization degree negatively affecting in the grasp of the condition of tissue
2: Visualization degree difficult to grasp the condition of tissue The evaluation result is shown in Table 2.

TABLE 2

| | EVALUATION RESULT OF IMAGE QUALITY | | | | | | |
|---|---|---|---|---|---|---|---|
| | DISTANCE RESOLUTION [μm] | AZIMUTH RESOLUTION [μm] | PENTRATION [mm] | CARPUS | MP JOINT FLEXOR TENDON | BICEPS BRACHII TENDON | MEDIAL MENISCUS |
| EXAMPLE 1 | 190 | 628 | 59 | 9.7 | 9.8 | 8.3 | 8.0 |
| EXAMPLE 2 | 212 | 640 | 56 | 9.4 | 9.7 | 8.1 | 7.8 |
| COMPARATIVE EXAMPLE 1 | 329 | 698 | 49 | 6.6 | 7.6 | 6.8 | 5.9 |
| COMPARATIVE EXAMPLE 2 | 339 | 696 | 50 | 6.4 | 7.4 | 6.4 | 6.0 |
| EXAMPLE 3 | 198 | 630 | 62 | 9.6 | 9.7 | 8.9 | 8.6 |
| EXAMPLE 4 | 222 | 646 | 54 | 9.2 | 9.6 | 7.9 | 7.6 |
| EXAMPLE 5 | 230 | 660 | 55 | 9.0 | 9.1 | 7.9 | 7.6 |
| EXAMPLE 6 | 220 | 691 | 60 | 8.9 | 9.6 | 7.7 | 8.1 |
| EXAMPLE 7 | 240 | 689 | 57 | 8.6 | 9.0 | 7.6 | 7.9 |
| COMPARATIVE EXAMPLE 3 | 346 | 688 | 52 | 6.0 | 5.8 | 6.6 | 6.3 |
| COMPARATIVE EXAMPLE 4 | 389 | 708 | 49 | 5.5 | 6.2 | 5.6 | 5.2 |
| COMPARATIVE EXAMPLE 5 | 341 | 692 | 52 | 5.9 | 7.0 | 6.6 | 6.2 |
| EXAMPLE 8 | 244 | 688 | 54 | 8.4 | 8.8 | 7.4 | 7.6 |
| EXAMPLE 9 | 222 | 689 | 60 | 8.9 | 9.6 | 7.7 | 8.1 |
| COMPARATIVE EXAMPLE 6 | 352 | 679 | 50 | 6.2 | 7.3 | 6.2 | 6.2 |

<Evaluation Result>

It was found that from the result in Table 2, Examples 1 to 9 showed the better distance resolutions compared with Comparative examples 1 to 6, and the better visualization evaluation compared with comparative examples 1 to 6. The specific evaluation result is shown below.

Figure 25A:
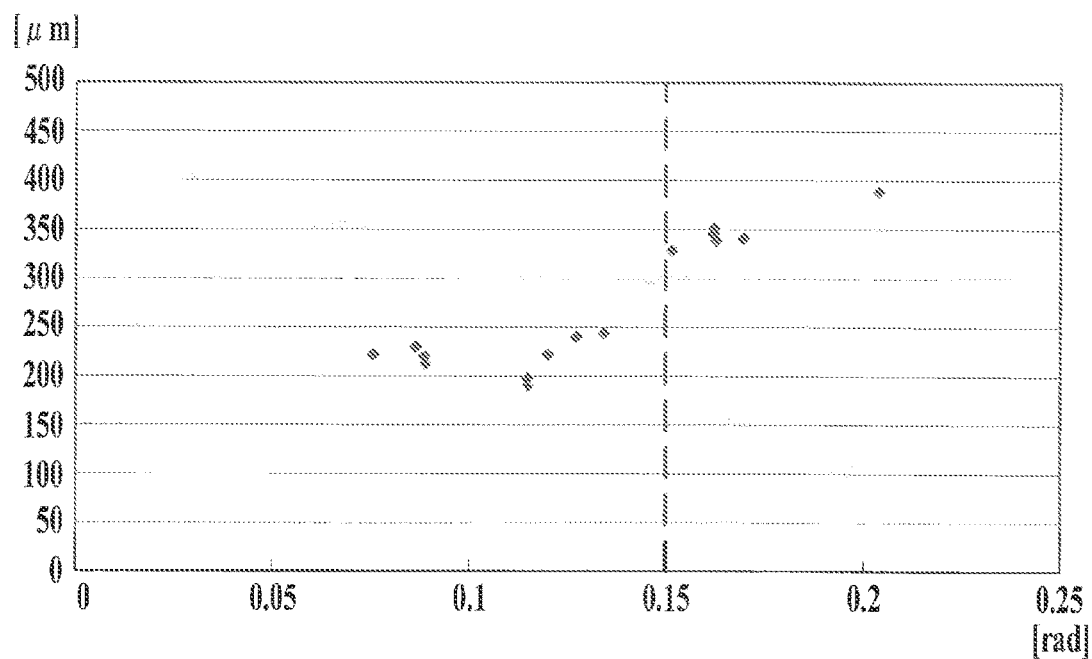
FIGS. 25A and 25B are diagrams each illustrating a relationship between a difference and an evaluation result, the difference being between the maximum value and the minimum value of the totaling result of the group delay of the ultrasound probe and the group delay of the driving waveform.

FIG. 25A is a graph illustrating a relationship between the distance resolution and the difference between the maximum value and the minimum value of the totaling values of the group delay of the ultrasound probe and the group delay of the ultrasound probe in the frequency band where the frequency band included in the transmission/reception frequency band at −20 dB of the ultrasound probe and the frequency band at −20 dB of the driving waveform overlap each other, obtained from the evaluation result of Examples 1 to 9 and Comparative examples 1 to 6. According to this drawing, the resistance resolution was more excellent in the case that the difference between the maximum value and the minimum value of the totaling values of the group delay of the ultrasound probe and the group delay of the ultrasound probe was equal to or less than 0.15 radian, compared with the case that the difference exceeded 0.15 radian.

Figure 25B:
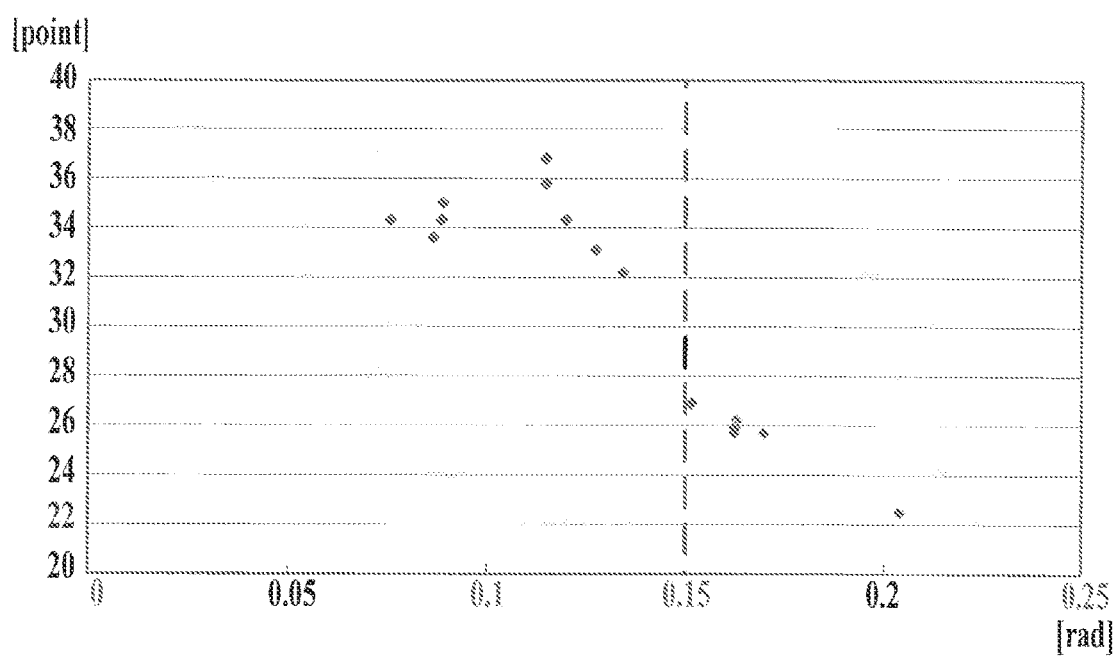

FIG. 25B is a graph illustrating a relationship between the total (total of image quality scores) of visualization evaluation values of the carpus, MP joint flexor tendon, biceps brachii tendon and medial meniscus and the difference between the maximum value and the minimum value of the totaling results of the group delay of the ultrasound probe and the group delay of the driving waveform in the frequency band where the frequency band included in the transmission/reception frequency band at −20 dB of the ultrasound probe and the frequency band at −20 dB of the driving waveform overlap each other, obtained from the evaluation result of Examples 1 to 9 and Comparative examples 1 to 6. According to this drawing, the total of the image quality scores in the case that the difference between the maximum value and the minimum value of the totaling values of the group delay of the ultrasound probe and the group delay of the ultrasound probe was equal to or less than 0.15 radian was far higher than that in the case that the difference exceeded 0.15 radian.

Figure 26A:
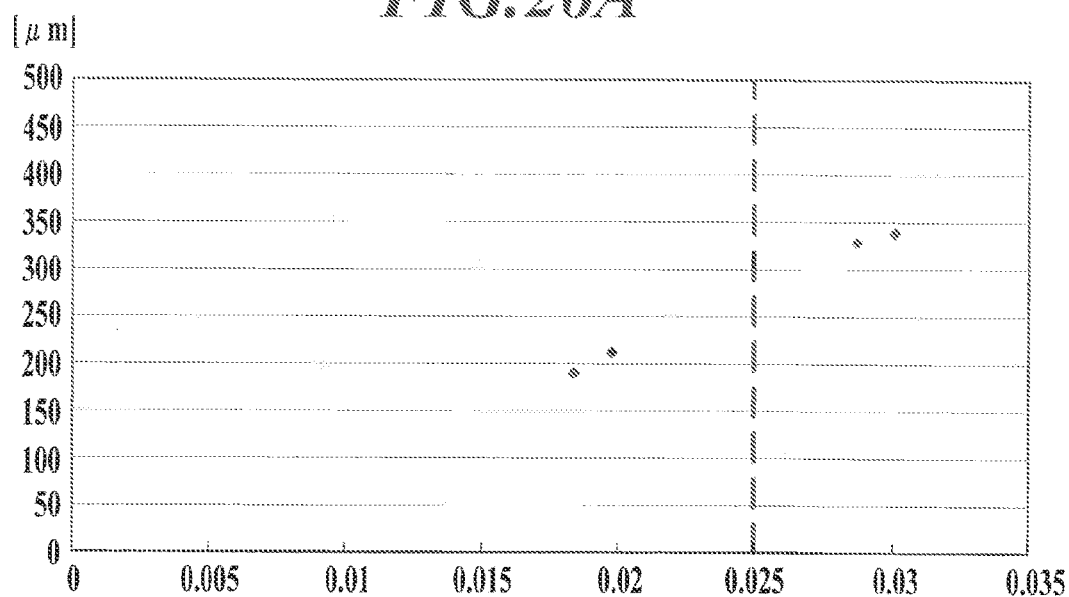
FIGS. 26A and 26B are diagrams each illustrating a relationship between a standard deviation of the group delay of the ultrasound probe and the evaluation result.

FIG. 26A is a graph illustrating a relationship between the distance resolution and the standard deviation of the group delay amounts in the transmission/reception bandwidth at −20 dB of the ultrasound probe, obtained from the evaluation result of Examples 1 to 2 and Comparative examples 1 to 2. According to this drawing, the distance resolution was more excellent in the case that the standard deviation of the group delay amounts of the ultrasound probe was equal to or less than 0.025, compared with the case that the standard deviation exceeded 0.025.

Figure 26B:
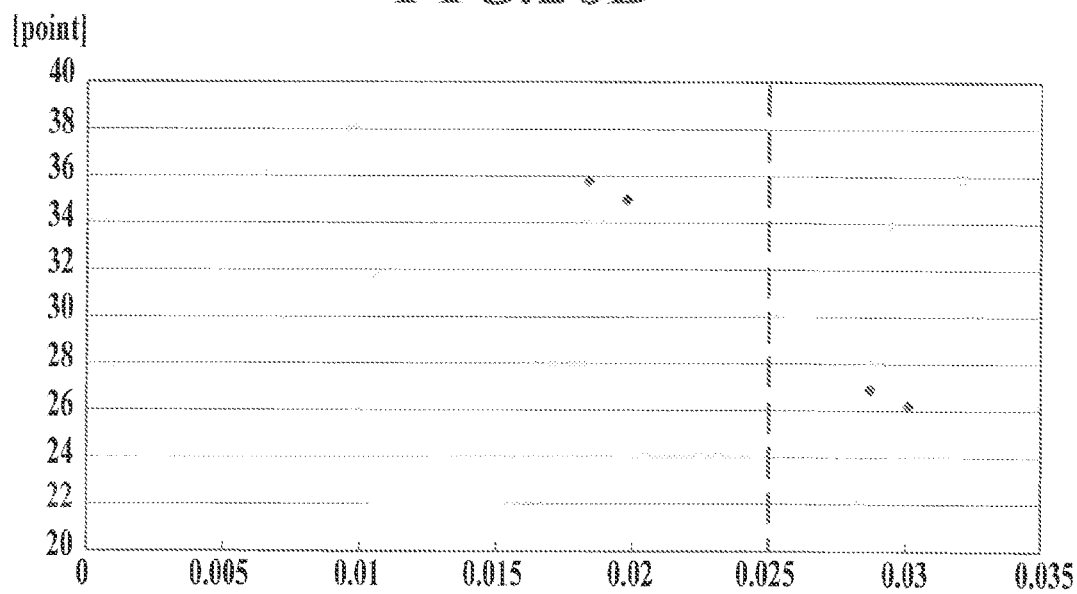

FIG. 26B is a graph illustrating the relationship between the total of image quality scores and the standard deviation of the group delay amounts in the transmission/reception frequency bandwidth at −20 dB of the ultrasound probe, obtained from the evaluation result of the Examples 1 to 2 and Comparative examples 1 to 2. According to this drawing, the total of the image quality scores in the case that the standard deviation of the group delays of the ultrasound probe was equal to or less than 0.025 was far higher than that in the case that the standard deviation exceeded 0.025.

Figure 27A:
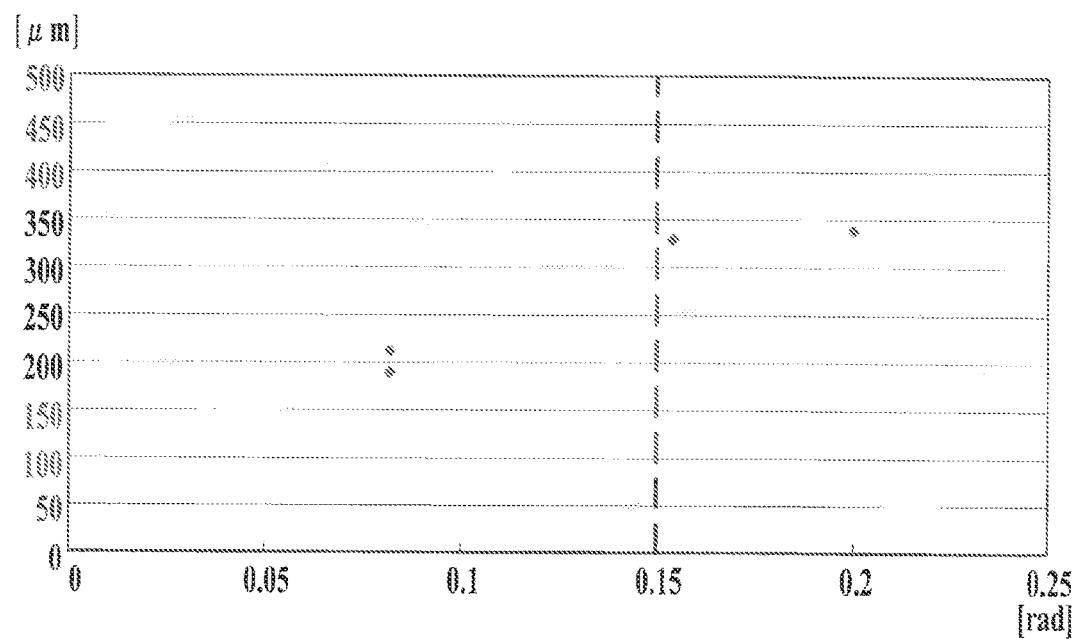
FIGS. 27A and 27B are diagrams each illustrating a relationship between a difference between the maximum value and the minimum value of the group delay of the ultrasound probe and the evaluation result.

FIG. 27A is a graph illustrating a relationship between the distance resolution and the difference between the maximum value and the minimum value of the group delay amounts in the transmission/reception frequency bandwidth at −20 dB of the ultrasound probe, obtained from the evaluation result of Examples 1 to 2 and Comparative examples 1 to 2. According to this drawing, the distance resolution was more excellent in the case that the difference between the maximum value and the minimum value of the group delay amounts of the ultrasound probe was equal to or less than 0.15 radian, compared with the case that the difference exceeds 0.15 radian.

Figure 27B:
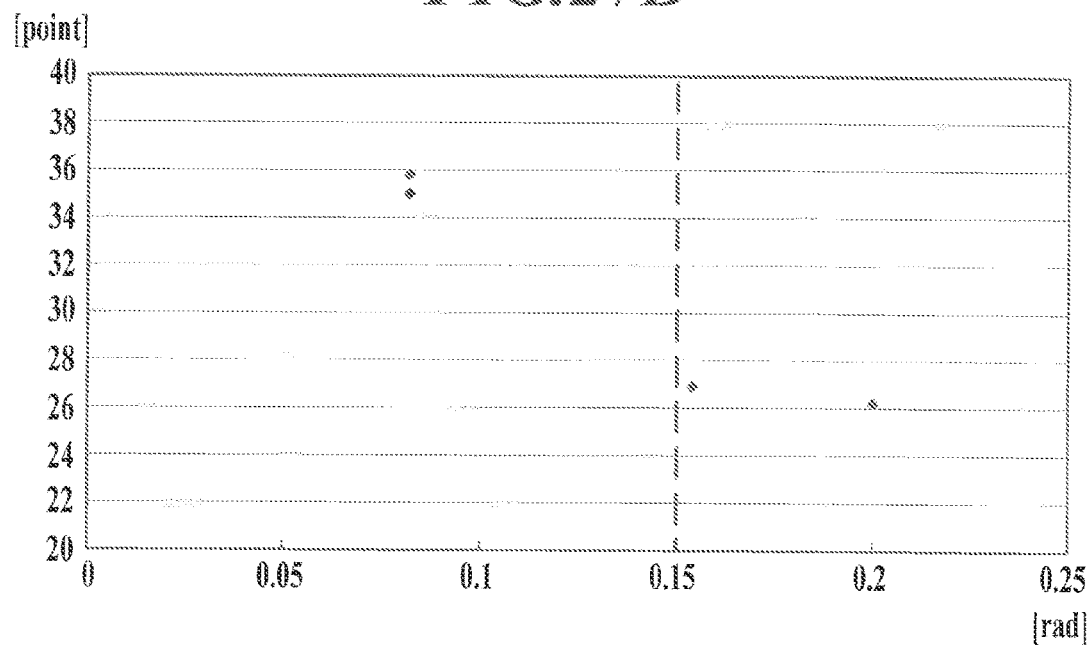

FIG. 27B is a graph illustrating a relationship between the total of the image quality scores and the difference between the maximum value and the minimum value of the group delay amounts in the transmission/reception frequency bandwidth at −20 dB of the ultrasound probe, obtained from the evaluation result of Examples 1 to 2 and Comparative examples 1 to 2. According to this drawing, the total of the image quality scores in the case that the difference between the maximum value and the minimum value of the group delay amounts of the ultrasound probe was equal to or less than 0.15 radian was far higher than that in the case that the difference exceeded 0.15 radian.

Figure 28A:
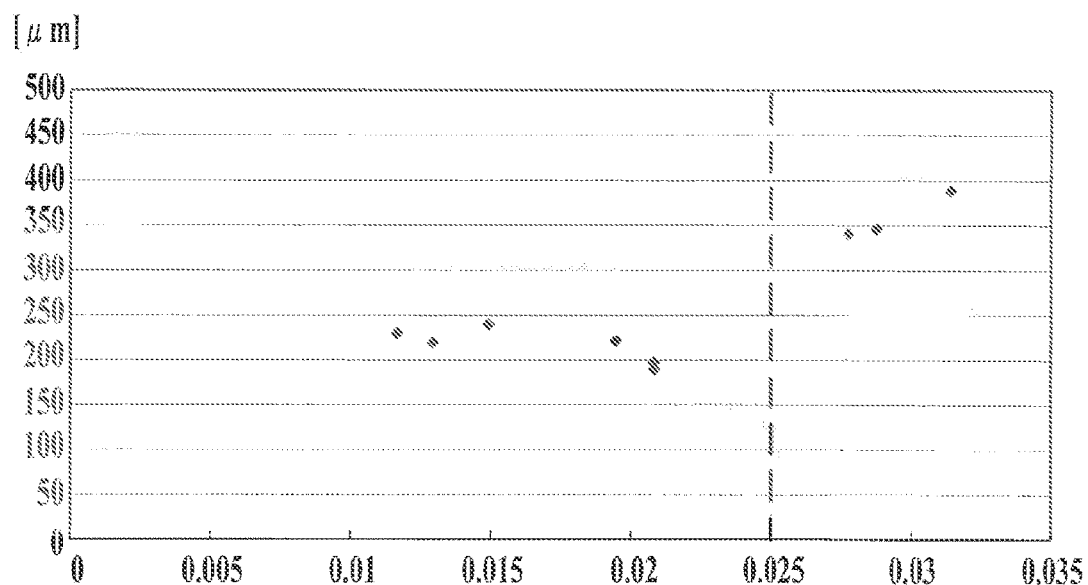
FIGS. 28A and 28B are diagrams each illustrating a relationship between a standard deviation of the group delay of the driving waveform and the evaluation result.

FIG. 28A is a graph illustrating a relationship between the distance solution and the standard deviation of the group delays of the driving waveform in the frequency band where the frequency band included in the transmission/reception frequency band at −20 dB of the ultrasound probe A and the frequency band at −20 dB of the driving waveform overlap each other, obtained from the evaluation result of Examples 1, 3 to 7 and Comparative examples 3 to 5. According to this drawing, the distance resolution was more excellent in the case that the standard deviation of the group delays of the driving waveform was equal to or less than 0.025, compared with the case that the standard deviation exceeds 0.025.

Figure 28B:
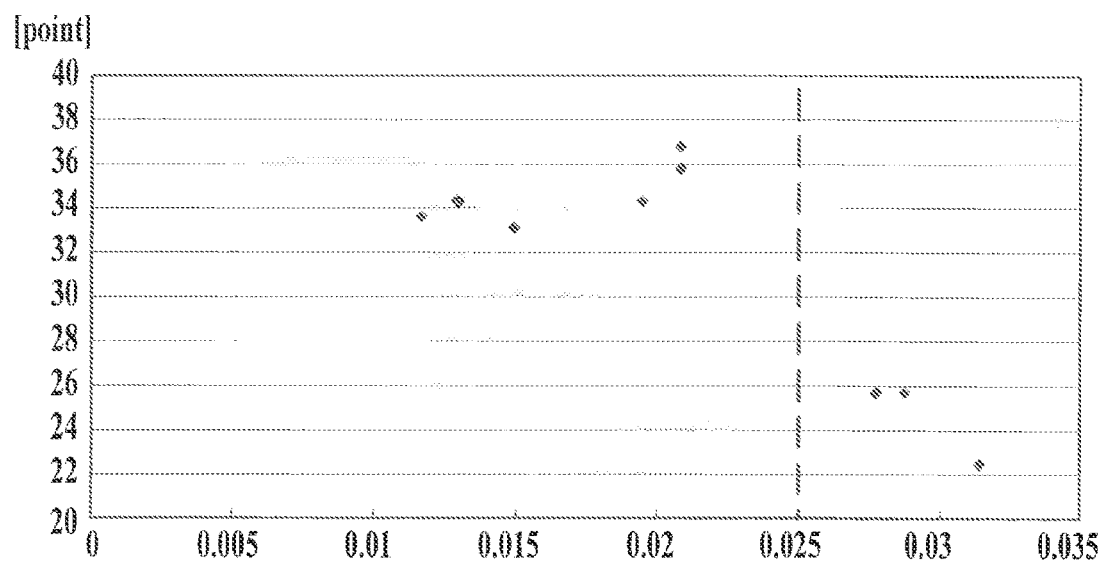

FIG. 28B is a graph illustrating a relationship between the total of the image quality scores and the standard deviation of the group delays of the driving waveform in the frequency band where the frequency band included in the transmission/ reception frequency band at −20 dB of the ultrasound probe A and the frequency band at −20 dB of the driving waveform overlap each other, obtained from the evaluation result of Examples 1, 3 to 7 and Comparative examples 3 to 5. According to this drawing, the total of the image quality scores in the case that the standard deviation of the group delays of the driving waveform was equal to or less than 0.025 was far higher than that in the case that the standard deviation exceeded 0.025.

Figure 29A:
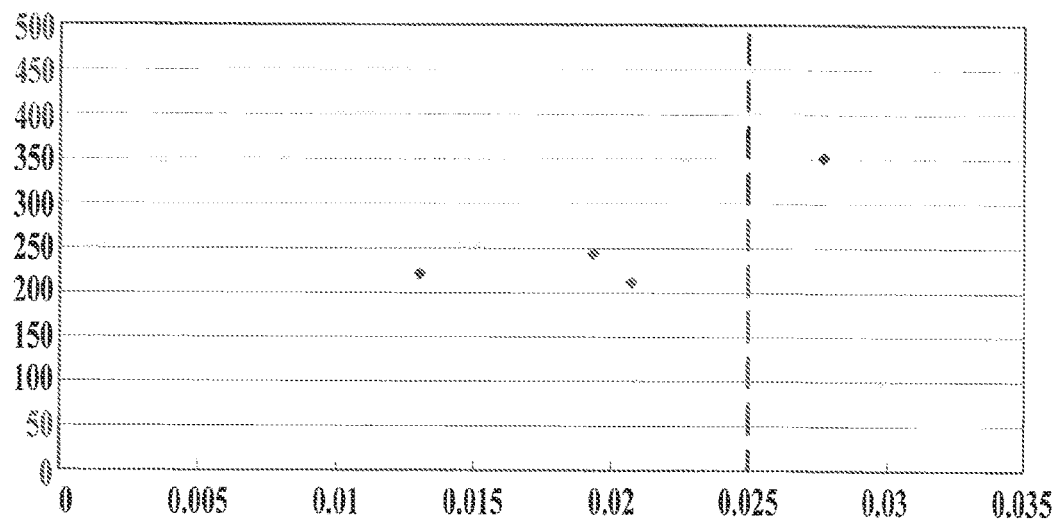
FIGS. 29A and 29B are diagrams each illustrating a relationship between a standard deviation of the group delay of the driving waveform and the evaluation result.

FIG. 29A is a graph illustrating a relationship between the distance resolution and the standard deviation of the group delays of the driving waveform in the frequency band where the frequency band included in the transmission/reception frequency band at −20 dB of the ultrasound probe B and the frequency band at −20 dB of the driving waveform overlap each other, obtained from the evaluation result of Examples 2, 8, 9 and Comparative example 6. According to this drawing, the distance resolution was more excellent in the case that the standard deviation of the group delays of the driving waveform was equal to or less than 0.025, compared with the case that the standard deviation exceeded 0.025.

Figure 29B:
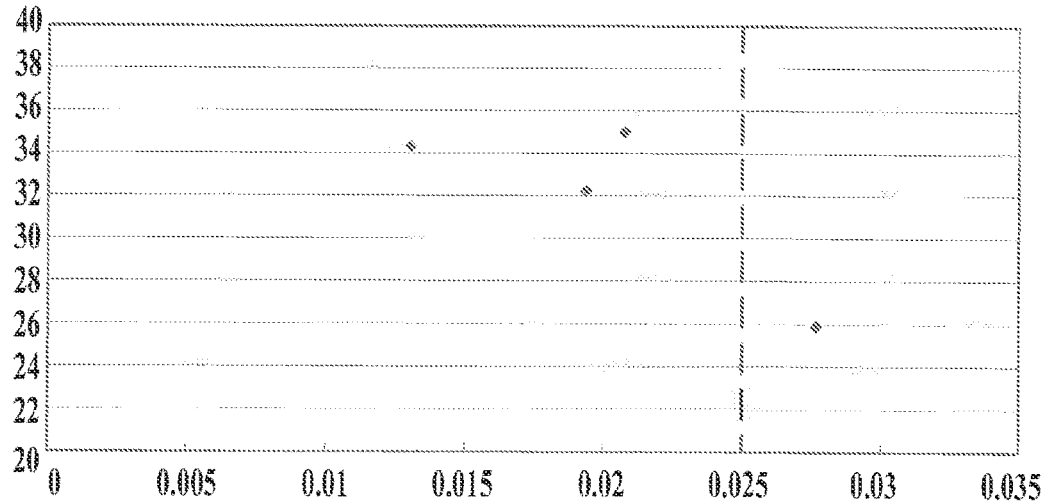

FIG. 29B is a graph illustrating a relationship between the total of the image quality scores and the standard deviation of the group delays of the driving waveform in the frequency band where the frequency band included in the transmission/ reception frequency band at −20 dB of the ultrasound probe B and the frequency band at −20 dB of the driving waveform overlap with each other, obtained from the evaluation result of Examples 2, 8, 9 and Comparative example 6. According to this drawing, the total of the image quality scores in the case that the standard deviation of the group delays of the driving waveform was equal to or less than 0.025 was far higher than that in the case that the standard deviation exceeded 0.025.

Figure 30A:
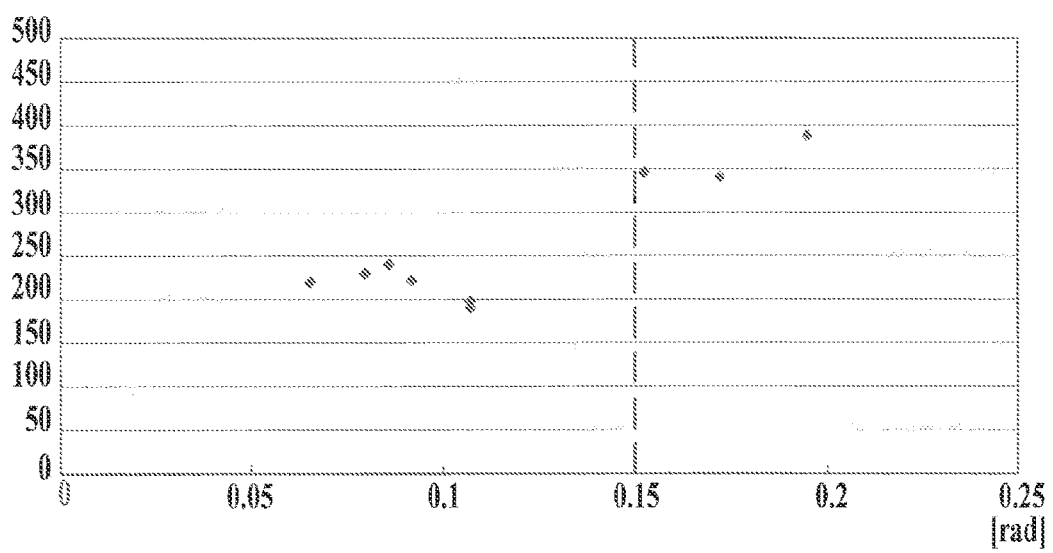
FIGS. 30A and 30B are diagrams each illustrating a relationship between a difference between the maximum value and the minimum value of the group delay of the driving waveform and the evaluation result.

FIG. 30A is a graph illustrating a relationship between the distance resolution and the difference between the maximum value and the minimum value of the group delays of the driving waveform in the frequency band where the frequency band included in the transmission/reception frequency band at −20 dB of the ultrasound probe A and the frequency band at −20 dB of the driving waveform overlap each other, obtained from the evaluation result of Examples 1, 3 to 7 and Comparative examples 3 to 5. According to this drawing, the distance resolution was more excellent in the case that the difference between the maximum value and the minimum value of the group delays of the driving waveform was equal to or less than 0.15 radian, compared with the case that the difference exceeded 0.15 radian.

Figure 30B:
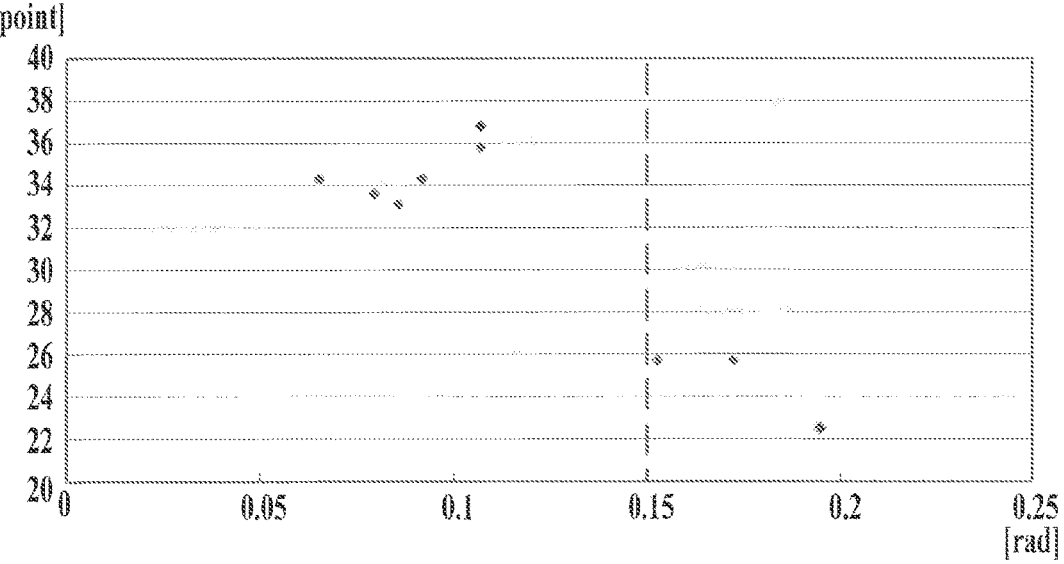

FIG. 30B is a graph illustrating a relationship between the total of the image quality scores and the difference between the maximum value and the minimum value of the group delays of the driving waveform in the frequency band where the frequency band included in the transmission/reception frequency band at −20 dB of the ultrasound probe A and the frequency band −20 dB of the driving waveform overlap each other, obtained from the evaluation result of Examples 1, 3 to 7 and Comparative example 3 to 5. According to this drawing, the total of the image quality scores in the case that the difference between the maximum value and the minimum value of the group delays of the driving waveform was equal to or less than 0.15 radian was far higher than that in the case that the difference exceeded 0.15 radian.

Figure 31A:
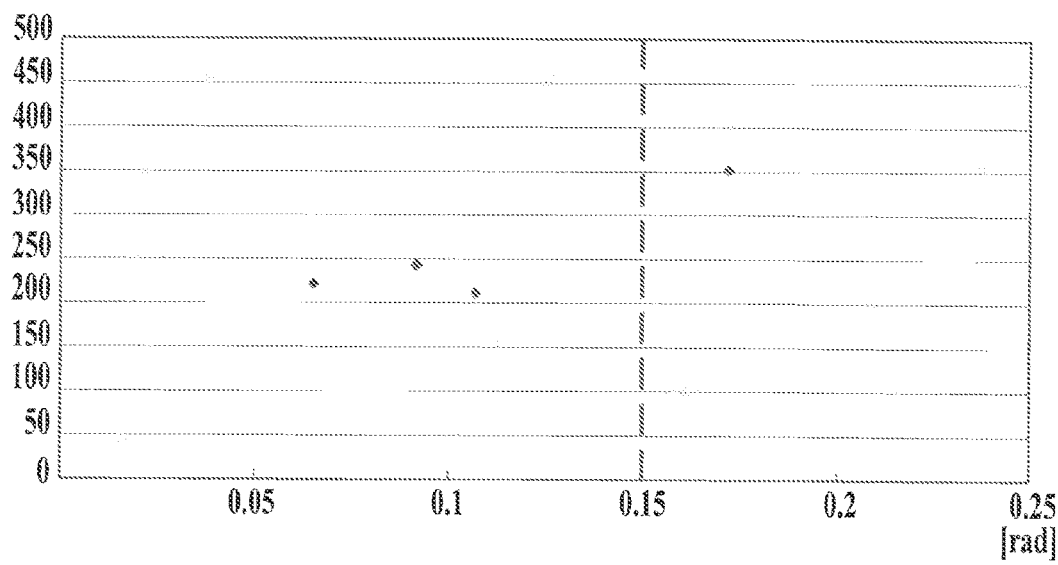
FIGS. 31A and 31B are diagrams each illustrating a relationship between a difference between the maximum value and the minimum value of the group delay of the driving waveform and the evaluation result.

FIG. 31A is a graph illustrating a relationship between the distance solution and the difference between the maximum value and the minimum value of the group delays of the driving waveform in the frequency band where the frequency band included in the transmission/reception frequency band at −20 dB of the ultrasound probe B and the frequency band at −20 dB of the driving waveform overlap each other, obtained from the evaluation result of Examples 2, 8, 9 and Comparative example 6. According to this drawing, the distance resolution was more excellent in the case that the difference between the maximum value and the minimum value of the group delays of the driving waveform was equal to or less than 0.15 radian, compared with the case that the difference exceeded 0.15 radian.

Figure 31B:
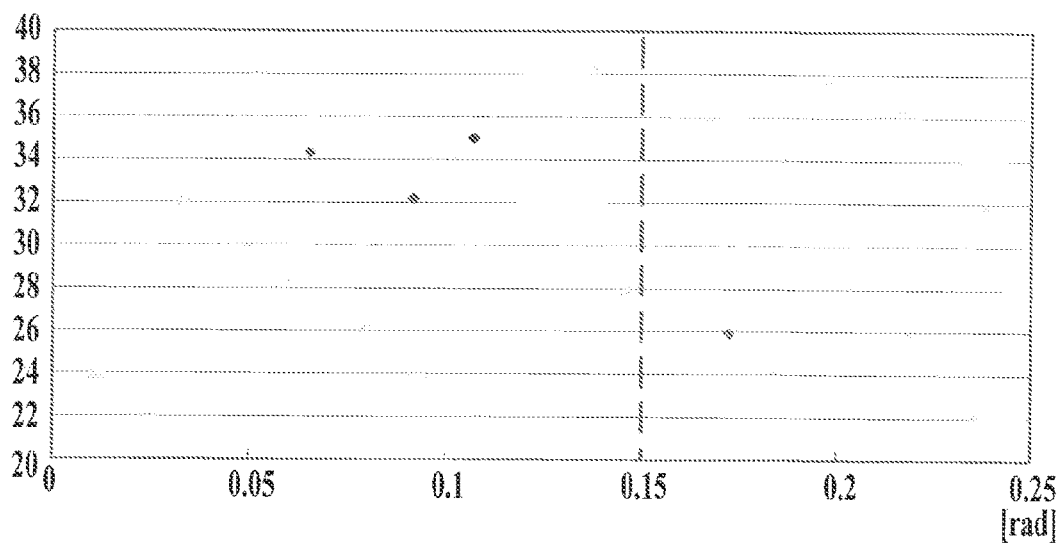

FIG. 31B is a graph illustrating a relationship between the total of the image quality scores and the difference between the maximum value and the minimum value of the group delays of the driving waveform in the frequency band where the frequency band included in the transmission/reception frequency band at −20 dB of the ultrasound probe B and the frequency band at −20 dB of the driving waveform overlap each other, obtained from the evaluation result of Examples 2, 8, 9 and Comparative example 6. According to this drawing, the total of the image quality scores in the case that the difference between the maximum value and the minimum value of the group delays of the driving waveform was equal to or less than 0.15 radian was far higher than that in the case that the difference exceeded 0.15 radian.

As described above, according to this embodiments, the ultrasound probe 2 is set so that the difference between the maximum value and the minimum value of the group delays obtained from the phase difference for each frequency between the input pulse signal and the reception signal obtained from the reflected ultrasound of the transmission ultrasound output based on the pulse signal, in the transmission/reception frequency band −20 dB of the ultrasound probe 2, becomes equal to or less than 0.15 radian, or so that the standard deviation in the transmission/reception frequency band at −20 dB of the ultrasound probe 2 is equal to or less than 0.025. As a result, unevenness of the group delay amounts in the ultrasound probe becomes small in the band in which the ultrasounds are transmitted/received, and accordingly cancellation among the plural kinds of higher harmonic waves is reduced and the ultrasound image having the excellent distance resolution can be obtained.

Because the ultrasound probe 2 of this embodiment has −20 dB fractional bandwidth of 120% or more, further high resolution ultrasound can be transmitted/received.

Moreover, the ultrasound probe 2 of this embodiment outputs the transmission ultrasound to the test object when receiving the input of the pulse signal, and outputs the reception signal when receiving the reflected ultrasound from the test object. The transmission section 12 outputs the pulse signal of the predetermined driving waveform so that the ultrasound probe 2 creates the transmission ultrasound. The transmission section 12 outputs the pulse signal according to which the difference between the maximum value and the minimum value of the group delays obtained from the phase difference for each frequency in the frequency band where the frequency band included in the transmission/reception frequency band at −20 dB of the ultrasound probe 2 and the frequency band at −20 dB of the driving waveform in the pulse signal overlap each other is equal to or less than 0.15 radian, or according to which the standard deviation in the frequency band where the frequency band included in the transmission/reception frequency band at −20 dB of the ultrasound probe and the frequency band at −20 dB of the driving signal in the pulse signal overlap each other is equal to or less than 0.025. As a result, unevenness of the group delay amounts in the driving waveform becomes small in the band where the ultrasounds are transmitted/received, and accordingly cancellation among the multiple kinds of the higher harmonic waves is reduced and the ultrasound image having the excellent distance resolution can be obtained.

Furthermore, the ultrasound probe 2 of this embodiment outputs the transmission ultrasound to a test object when receiving the input of the pulse signal, and outputs the reception signal when receiving the reflected ultrasound from the test object. The transmission section 12 outputs the pulse signal of the predetermined driving waveform so as to cause the ultrasound probe 2 to generate the transmission ultrasound. The ultrasound probe 2 and the driving waveform of the pulse signal output from the transmission section 12 are set so that the difference between the maximum value and the minimum value of the totaling values of the group delay obtained from the phase difference for each frequency between the pulse signal input to the ultrasound probe 2 and the reception signal obtained from the reflected ultrasound of the transmission ultrasound output based on the pulse signal, and the group delay obtained from the phase difference for each frequency of the pulse signal output by the transmission section 12, in the frequency band where the frequency band included in the transmission/reception frequency band at −20 dB of the ultrasound probe 2 and the frequency band at −20 dB of the driving signal in the pulse signal becomes equal to or less than 0.015 radian. As a result, unevenness of the group delay amounts in the reception signal becomes small at the time of transmitting/receiving the ultrasound in the band in which the ultrasound is transmitted/received, and accordingly cancellation among the multiple kinds of the higher harmonic waves is reduced and the ultrasound image having the excellent distance resolution was obtained.

Moreover, the ultrasound probe 2 of this embodiment is set so that the difference between the maximum value and the minimum value of the group delays obtained from the phase difference in each frequency between the input pulse signal and the reception signal obtained from the reflected ultrasound of the transmission ultrasound output based on the pulse signal, in the transmission/reception frequency band at −20 dB of the ultrasound probe 2, is equal to or less than 0.15 radian, or so that the standard deviation in the transmission/reception frequency band at −20 dB of the ultrasound probe 2 is equal to or less than 0.025. The transmission section 12 outputs the pulse signal of the driving waveform according to which the difference of the maximum value and the minimum value of the group delays obtained from the phase difference in each frequency in the frequency band where the frequency band included in the transmission/reception frequency band at −20 dB of the ultrasound probe 2 and the frequency band at −20 dB of the driving waveform in the pulse signal overlap each other is equal to or less than 0.15 radian, or according to which the standard deviation in the frequency band where the frequency band included in the transmission/reception frequency band at −20 dB of the ultrasound probe 2 and the frequency band at −20 dB of the driving waveform in the pulse signal overlap each other is equal to or less than 0.025. As a result, unevenness of the group delay amounts in the ultrasound probe and unevenness of the group delay amounts in the driving waveform become small. Thus, the unevenness of the group delay amounts in the reception signals becomes small. Therefore, designing is facilitated and the ultrasound image having the excellent distance resolution can be obtained.

Furthermore, the transmission section 12 of this embodiment outputs the pulse signal of the driving signal in which the frequency bandwidth where the frequency band included in the transmission/reception frequency band at −20 dB of the ultrasound probe 2 and the frequency band at −20 dB of the driving waveform in the pulse signal overlap each other convers 70% or more of the transmission/reception frequency bandwidth at −20 dB of the ultrasound probe 2. As a result, broadband ultrasounds can be transmitted/received.

Moreover, the transmission section 12 of this embodiment outputs the pulse signal whose period is equal to or more than 1.5. As a result, the maximum output voltage at the time of outputting the pulse signal can be suppressed, and the costs can be reduced.

Furthermore, the transmission section 12 of this embodiment outputs the pulse signal of the driving waveform whose pulse duration is equal to or more than the time corresponding to two periods at the center frequency of the transmission/reception frequency band at −20 dB of the ultrasound probe 2. As a result, the maximum output voltage at the time of outputting the pulse signal can be suppressed, and the costs can be reduced.

Moreover, the transmission section 12 of this embodiment outputs the pulse signal by the control signal of five values or less. As a result, the distance resolution can be improved at low costs.

Furthermore, the transmission section 12 of this embodiment outputs the pulse signals of difference driving waveforms to the same scanning line with a predetermined time interval, for plural times. The image generating section 14 combines the reception signals obtained from the reflected ultrasounds of the transmission ultrasounds generated by the pulse signals of plural times to generate the ultrasound image data based on the combined reception signals. As a result, the broadband reception of higher harmonic waves can be achieved in the pulse inversion method, and the ultrasound image having further-improved distance resolution can be obtained at low costs.

Moreover, the transmission section 12 of this embodiment outputs the pulse signals of the driving waveforms having the asymmetric relationship with each other to the same scanning line with a predetermined time interval for plural times. As a result, the penetration can be improved while maintaining the resolution without providing a transmission driving device having an advanced positive/negative driving symmetric property.

Furthermore, the transmission section 12 outputs the pulse signal which includes the intensity peaks of the frequency power spectrum on the low frequency side and the high frequency side with respect to the center frequency of the transmission/reception frequency band at −20 dB of the ultrasound probe 2. As a result, broadband wave transmission becomes possible. Thus, not only high-order higher harmonic components but also difference tone components can be utilized, and broadband higher harmonic waves can be received. Accordingly, the distance resolution is improved.

Moreover, the transmission section 12 of this embodiment outputs the pulse signal including two or more of the intensity peaks of the frequency power spectrum on the high frequency side with respect to the center frequency of the transmission/reception frequency band at −20 dB of the ultrasound probe 2. As a result, higher harmonic wave with a wider band can be received, and the distance resolution is further improved.

Incidentally, the descriptions of the embodiments of the present invention are mere examples of the ultrasound image diagnosis apparatus of the present invention, and the present invention is not limited to those. The detailed configurations and operations of the respective functional sections constituting the ultrasound image diagnosis apparatus can be arbitrary changed.

The present U.S. patent application claims a priority under the Paris Convention of Japanese patent application No. 2014-082675 filed on Apr. 14, 2014, in which all contents of this application are disclosed, and which shall be a basis of correction of an incorrect translation.

What is claimed is:

1. An ultrasound probe comprising:
   a lamination including a backing layer, a piezoelectric layer including oscillators, and an acoustic matching layer;
   an ultrasound input and output unit to output a transmission ultrasound to a test object in response to an input of a pulse signal; and
   a signal input and output unit to output a reception signal when the ultrasound input and output unit receives a reflected ultrasound from the test object,
   wherein the ultrasound probe is configured so that a difference between a maximum value and a minimum value of a group delay in a transmission and reception frequency band at −20 dB of the ultrasonic probe is equal to or less than 0.15 radian, the group delay being obtained from a phase difference for each frequency between the input pulse signal and the reception signal obtained from the reflected ultrasound of the transmission ultrasound output by the pulse signal, or so that a standard deviation of the group delay in the transmission and reception frequency band at −20 dB of the ultrasonic probe is equal to or less than 0.025, by at least one of the setting characteristics of piezoelectric material applied to the oscillators, setting damping performance and/or acoustic reflection performance of backing material composing the backing layer, setting the number of sheets of the acoustic matching material composing the acoustic matching layer, or setting acoustic impedance and thickness of the acoustic matching material.

2. The ultrasound probe of claim 1, wherein a fractional bandwidth at −20 dB is 120% or more.

3. A method of producing the ultrasound probe recited in claim 1, including the steps of:
laminating a backing layer, a piezoelectric layer, and acoustic matching layer, and an acoustic lens, wherein the piezoelectric layer includes oscillators; and
adjusting frequency characteristics and group delay characteristics of the ultrasound probe by at least one of the setting characteristics of piezoelectric material applied to the oscillators, setting damping performance and/or acoustic reflection performance of backing material composing the backing layer, setting the number of sheets of the acoustic matching material composing the acoustic matching layer, or setting acoustic impedance and thickness of the acoustic matching material so that at least one of:
a difference between a maximum value and a minimum value of a group delay in the transmission and reception frequency band at −20 dB of the ultrasound probe is equal to or less than 0.15 radian, the group delay being obtained from a phase difference in each frequency between the input pulse signal and the reception signal obtained from the reflected ultrasound of the transmission ultrasound output by the pulse signal, or so that a standard deviation of the group delay in the transmission and reception frequency band at −20 dB of the ultrasound probe is equal to or less than 0.025, or
a difference between a maximum value and a minimum value of a group delay obtained from a phase difference in each frequency in the frequency band where the transmission and reception frequency band at −20 dB of the ultrasound probe and the frequency band at −20 dB of the driving waveform in a pulse signal overlap each other is equal to or less than 0.15 radian, or a standard deviation of the group delay in the frequency band where the transmission and reception frequency band at −20 dB of the ultrasound probe and the frequency band at −20 dB of the driving waveform in the pulse signal overlap each other is equal to or less than 0.025.

4. The ultrasound probe of claim 1, wherein a frequency bandwidth where the frequency band of the ultrasound probe and a frequency band of the pulse signal overlap each other is at least 70% of the transmission and reception frequency bandwidth at −20 dB of the ultrasound probe.

5. An ultrasound image diagnosis apparatus comprising:
an ultrasound probe which outputs at least one transmission ultrasound to a test object in response to an input of at least one pulse signal, and outputs at least one reception signal when at least one reflected ultrasound from the test object is received; and
a transmission section which outputs a pulse signal of a predetermined driving waveform so as to cause the ultrasound probe to generate the transmission ultrasound,
wherein the ultrasound probe has a transmission and reception frequency band at −20 dB and the driving waveform has a frequency band at −20 dB,
wherein the transmission section outputs the pulse signal of the driving waveform according to which a difference between a maximum value and a minimum value of a group delay obtained from a phase difference in each frequency in a frequency band where the transmission and reception frequency band at −20 dB of the ultrasound probe and the frequency band at −20 dB of the driving waveform in the pulse signal overlap each other is equal to or less than 0.15 radian, or according to which a standard deviation of the group delay in the frequency band where the transmission and reception frequency band at −20 dB of the ultrasound probe and the frequency band at −20 dB of the driving waveform in the pulse signal overlap each other is equal to or less than 0.025.

6. The ultrasound image diagnosis apparatus of claim 5, wherein the transmission section outputs the pulse signal of the driving waveform in which the frequency band where the transmission and reception frequency band at −20 dB of the ultrasound probe and the frequency band at −20 dB of the driving waveform in the pulse signal overlap each other covers 70% or more of the transmission and reception frequency bandwidth at −20 dB of the ultrasound probe.

7. The ultrasound image diagnosis apparatus of claim 5, wherein the transmission section outputs the pulse signal of the driving waveform whose period is equal to or more than 1.5.

8. The ultrasound image diagnosis apparatus of claim 5, wherein the transmission section outputs the pulse signal of the driving waveform whose pulse duration is equal to or more than a time corresponding to two periods at a center frequency of the transmission and reception frequency band at −20 dB of the ultrasound probe.

9. The ultrasound image diagnosis apparatus of claim 5, wherein the transmission section outputs the pulse signal according to a control signal of five values or less.

10. The ultrasound image diagnosis apparatus of claim 5, wherein the transmission section outputs the pulse signals of different driving waveforms to a same scanning line with a predetermined time interval for plural times, and
wherein the ultrasound image diagnosis further includes an image generating section to combine the reception signals obtained from the reflected ultrasounds of the transmission ultrasounds generated by the plural pulse signals to generate an ultrasound image data based on the combined reception signals.

11. The ultrasound image diagnosis apparatus of claim 10, wherein the transmission section outputs the pulse signals whose driving waveforms have an asymmetric relationship with each other to the same scanning line with the predetermined time interval for plural times.

12. The ultrasound image diagnosis apparatus of claim 5, wherein the transmission section outputs the pulse signal including intensity peaks of a frequency power spectrum on a low frequency side and on a high frequency side with respect to a center frequency of the transmission and reception frequency band at −20 dB of the ultrasonic probe.

13. The ultrasound image diagnosis apparatus of claim 12, wherein the transmission section outputs the pulse signal including two or more of intensity peaks of a frequency power spectrum on the high frequency side with respect to the center frequency of the transmission and reception frequency band at −20 dB of the ultrasound probe.

14. The ultrasound image diagnosis apparatus of claim 5, wherein a fractional bandwidth at −20 dB of the ultrasound probe is 120% or more.

15. An ultrasound image diagnosis apparatus comprising:

an ultrasound probe which outputs a transmission ultrasound to a test object in response to an input of a pulse signal, and outputs a reception signal when a reflected ultrasound from the test object is received, the ultrasound probe comprising a lamination including a backing layer, a piezoelectric layer including oscillators, and an acoustic matching layer; and a transmission section which outputs a pulse signal of a predetermined driving waveform so as to cause the ultrasound probe to generate the transmission ultrasound, wherein the ultrasound probe has a transmission and reception frequency band at −20 dB and the driving waveform has a frequency band at −20 dB, wherein the ultrasound probe and the driving waveform of the pulse signal output from the transmission section are set so that a difference between a maximum value and a minimum value of a totaling value in a frequency band where the transmission and reception frequency band at −20 dB of the ultrasound probe and the frequency band at −20 dB of the driving waveform in the pulse signal overlap each other is equal to or less than 0.15 radian, the totaling value being obtained by totalizing a group delay obtained from a phase difference in each frequency between the pulse signal input to the ultrasound probe and the reception signal obtained from the reflected ultrasound of the transmission ultrasound output by the pulse signal and a group delay obtained from a phase difference in each frequency of the pulse signal output by the transmission section, the ultrasound probe being set by at least one of the setting characteristics of piezoelectric material applied to the oscillators, setting damping performance and/or acoustic reflection performance of backing material composing the backing layer, setting the number of sheets of the acoustic matching material composing the acoustic matching layer, or setting acoustic impedance and thickness of the acoustic matching material.

16. The ultrasound image diagnosis apparatus of claim 15, wherein the ultrasound probe is set so that a difference between a maximum value and a minimum value of a group delay in the transmission and reception frequency band at −20 dB of the ultrasound probe is equal to or less than 0.15 radian, the group delay being obtained from a phase difference in each frequency between the input pulse signal and the reception signal obtained from the reflected ultrasound of the transmission ultrasound output by the pulse signal, or so that a standard deviation of the group delay in the transmission and reception frequency band at −20 dB of the ultrasound probe is equal to or less than 0.025, and wherein the transmission section outputs the pulse signal of the driving waveform according to which a difference between a maximum value and a minimum value of a group delay obtained from a phase difference in each frequency in the frequency band where the transmission and reception frequency band at −20 dB of the ultrasound probe and the frequency band at −20 dB of the driving waveform in the pulse signal overlap each other is equal to or less than 0.15 radian, or a standard deviation of the group delay in the frequency band where the transmission and reception frequency band at −20 dB of the ultrasound probe and the frequency band at −20 dB of the driving waveform in the pulse signal overlap each other is equal to or less than 0.025.

17. The ultrasound image diagnosis apparatus of claim 15, wherein a frequency bandwidth where the frequency band of the ultrasound probe and the frequency band of the pulse signal overlap each other is at least 70% of the transmission and reception frequency bandwidth at −20 dB of the ultrasound probe.

18. The ultrasound image diagnosis apparatus of claim 15, wherein a fractional bandwidth at −20 dB of the ultrasound probe is 120% or more.

\* \* \* \* \*